United States Patent
Kamrud et al.

(10) Patent No.: US 12,083,223 B2
(45) Date of Patent: Sep. 10, 2024

(54) NANOLIPOPROTEIN PARTICLES AND RELATED COMPOSITIONS METHODS AND SYSTEMS FOR LOADING RNA

(71) Applicant: LAWRENCE LIVERMORE NATIONAL SECURITY, LLC, Livermore, CA (US)

(72) Inventors: Kurt I. Kamrud, San Diego, CA (US); Nathaniel S. Wang, San Diego, CA (US); Martina Felderman, La Jolla, CA (US); Bolyn Hubby, Redwood City, CA (US); Heather D. Gouvis, San Diego, CA (US); Nicholas O. Fischer, Livermore, CA (US); Matthew A. Coleman, Oakland, CA (US); Angela Clare Evans, Livermore, CA (US); Wei He, Davis, CA (US); Amy Rasley, Livermore, CA (US); Craig D. Blanchette, San Leandro, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 1555 days.

(21) Appl. No.: 15/969,311

(22) Filed: May 2, 2018

(65) Prior Publication Data
US 2018/0318218 A1  Nov. 8, 2018

Related U.S. Application Data

(60) Provisional application No. 62/500,433, filed on May 2, 2017.

(51) Int. Cl.
*A61K 9/127* (2006.01)
*A61K 47/69* (2017.01)
(Continued)

(52) U.S. Cl.
CPC .......... *A61K 9/1272* (2013.01); *A61K 9/1274* (2013.01); *A61K 47/6917* (2017.08); *C12N 15/88* (2013.01); *A61K 48/0008* (2013.01)

(58) Field of Classification Search
CPC ................ A61K 9/1272; A61K 9/1274; A61K 47/6917; A61K 48/0008; C12N 15/88
See application file for complete search history.

(56) References Cited

U.S. PATENT DOCUMENTS

| 4,317,771 A | 3/1982 | Shiba et al. |
| 5,374,715 A | 12/1994 | Kanno et al. |

(Continued)

FOREIGN PATENT DOCUMENTS

| EP | 3426304 A1 | 1/2019 |
| JP | 2008516605 A | 5/2008 |

(Continued)

OTHER PUBLICATIONS

Adams, M.W.W., et al., "Hydrogenase," 1981, Biochimica et Biophysica Acta 594, 105-176.
(Continued)

*Primary Examiner* — Gollamudi S Kishore
(74) *Attorney, Agent, or Firm* — Steinfl + Bruno LLP

(57) ABSTRACT

Nanolipoprotein particles comprising at least a scaffold protein component and a membrane lipid component and related complexes, compositions, methods and systems are described, in which the membrane lipid component comprises at least one or more membrane forming lipids and one or more cationic lipids.

52 Claims, 22 Drawing Sheets

(51) Int. Cl.
*A61K 48/00* (2006.01)
*C12N 15/88* (2006.01)

(56) References Cited

U.S. PATENT DOCUMENTS

| | | | |
|---|---|---|---|
| 5,393,530 A | 2/1995 | Schneider et al. | |
| 5,679,559 A * | 10/1997 | Kim | C12N 15/87 |
| | | | 530/359 |
| 6,270,649 B1 | 8/2001 | Zeikus et al. | |
| 6,365,191 B1 | 4/2002 | Burman et al. | |
| 6,599,527 B1 | 7/2003 | Leigh et al. | |
| 7,015,471 B2 | 3/2006 | Franzen et al. | |
| 7,048,949 B2 | 5/2006 | Sligar et al. | |
| 7,083,958 B2 | 8/2006 | Sligar et al. | |
| 7,375,234 B2 | 5/2008 | Sharpless et al. | |
| 7,575,763 B2 | 8/2009 | Sligar et al. | |
| 7,592,008 B2 | 9/2009 | Sligar et al. | |
| 7,622,437 B2 | 11/2009 | Morrissey et al. | |
| 7,662,410 B2 | 2/2010 | Sligar et al. | |
| 7,691,414 B2 | 4/2010 | Sligar et al. | |
| 7,824,709 B2 | 11/2010 | Ryan et al. | |
| 8,183,010 B2 | 5/2012 | Swartz et al. | |
| 8,268,796 B2 | 9/2012 | Ryan | |
| 8,883,729 B2 | 11/2014 | Hoeprich et al. | |
| 8,889,623 B2 | 11/2014 | Hoeprich et al. | |
| 8,895,055 B2 | 11/2014 | Lam et al. | |
| 8,907,061 B2 | 12/2014 | Chromy et al. | |
| 9,303,273 B2 | 4/2016 | Hoeprich et al. | |
| 9,388,232 B2 | 7/2016 | Dasseux et al. | |
| 9,458,191 B2 | 10/2016 | Chromy et al. | |
| 9,644,038 B2 | 5/2017 | Luo et al. | |
| 9,688,718 B2 | 6/2017 | Baker et al. | |
| 10,151,037 B2 | 12/2018 | Hoeprich, Jr. et al. | |
| 10,934,628 B2 | 3/2021 | Hoeprich, Jr. et al. | |
| 11,053,322 B2 | 7/2021 | Luo et al. | |
| 11,207,422 B2 | 12/2021 | Coleman et al. | |
| 11,279,749 B2 | 3/2022 | Hoeprich, Jr. et al. | |
| 11,300,572 B2 | 4/2022 | Coleman et al. | |
| 11,713,359 B2 | 8/2023 | Luo et al. | |
| 2001/0051131 A1 | 12/2001 | Unger | |
| 2002/0041898 A1 | 4/2002 | Unger et al. | |
| 2003/0008014 A1 | 1/2003 | Shelness | |
| 2004/0101741 A1 | 5/2004 | Minteer et al. | |
| 2004/0180369 A1 | 9/2004 | Franzen et al. | |
| 2004/0204354 A1* | 10/2004 | Nelson | A61P 31/12 |
| | | | 424/450 |
| 2005/0182243 A1 | 8/2005 | Sligar et al. | |
| 2005/0244414 A1 | 11/2005 | Mundy et al. | |
| 2006/0013885 A1 | 1/2006 | Nah et al. | |
| 2006/0088524 A1 | 4/2006 | Morrissey et al. | |
| 2006/0127310 A1 | 6/2006 | Russell-Jones et al. | |
| 2006/0127467 A1 | 6/2006 | Watkin | |
| 2006/0189554 A1 | 8/2006 | Mumper et al. | |
| 2006/0211092 A1 | 9/2006 | Sligar et al. | |
| 2007/0101448 A1 | 5/2007 | Anantharamiah et al. | |
| 2007/0117179 A1 | 5/2007 | Kudlicki et al. | |
| 2007/0287034 A1 | 12/2007 | Minteer et al. | |
| 2008/0124350 A1 | 5/2008 | Mumper et al. | |
| 2008/0188399 A1 | 8/2008 | Sinko et al. | |
| 2008/0248565 A1 | 10/2008 | Katzen et al. | |
| 2009/0136937 A1 | 5/2009 | Coleman et al. | |
| 2009/0186393 A1 | 7/2009 | Baker et al. | |
| 2009/0192299 A1 | 7/2009 | Chromy et al. | |
| 2009/0203549 A1 | 8/2009 | Hoeprich, Jr. et al. | |
| 2009/0203706 A1 | 8/2009 | Zhao et al. | |
| 2009/0270331 A1 | 10/2009 | Remaley et al. | |
| 2009/0311276 A1 | 12/2009 | Hoeprich et al. | |
| 2009/0324706 A1 | 12/2009 | Mirkin et al. | |
| 2010/0092567 A1 | 4/2010 | Hoeprich et al. | |
| 2010/0158994 A1 | 6/2010 | Watkin | |
| 2010/0203609 A1 | 8/2010 | Yacoby et al. | |
| 2011/0059549 A1 | 3/2011 | Coleman et al. | |
| 2011/0178029 A1 | 7/2011 | Knudsen et al. | |
| 2011/0178164 A1 | 7/2011 | Cunha et al. | |
| 2011/0195450 A1 | 8/2011 | Kudlicki et al. | |
| 2011/0286915 A1 | 11/2011 | Lam et al. | |
| 2012/0148642 A1 | 6/2012 | Remaley et al. | |
| 2012/0245101 A1 | 9/2012 | Anantharamaiah et al. | |
| 2013/0164369 A1 | 6/2013 | Lam et al. | |
| 2013/0165636 A1 | 6/2013 | Luo et al. | |
| 2014/0273142 A1 | 9/2014 | Hoeprich | |
| 2014/0300341 A1 | 10/2014 | Davis et al. | |
| 2014/0308341 A1 | 10/2014 | Fujii et al. | |
| 2015/0140108 A1 | 5/2015 | Peer et al. | |
| 2016/0083858 A1 | 3/2016 | Hoeprich, Jr. et al. | |
| 2016/0235671 A1 | 8/2016 | Li et al. | |
| 2016/0324923 A1 | 11/2016 | Dasseux et al. | |
| 2018/0079829 A1 | 3/2018 | Luo et al. | |
| 2018/0186860 A1 | 7/2018 | Hoeprich, Jr. et al. | |
| 2019/0055658 A1 | 2/2019 | Hoeprich, Jr. et al. | |
| 2019/0094230 A1 | 3/2019 | Coleman et al. | |
| 2019/0142752 A1 | 5/2019 | Blanchette et al. | |
| 2019/0307692 A1 | 10/2019 | Blanchette et al. | |
| 2020/0046848 A1 | 2/2020 | Coleman et al. | |
| 2021/0317234 A1 | 10/2021 | Luo | |
| 2022/0211866 A1 | 7/2022 | Coleman et al. | |
| 2022/0283171 A1 | 9/2022 | Coleman et al. | |

FOREIGN PATENT DOCUMENTS

| | | | |
|---|---|---|---|
| JP | 2015110677 A | | 6/2015 |
| WO | 99/59550 A1 | | 11/1999 |
| WO | 00/65099 A1 | | 11/2000 |
| WO | 02/40501 A2 | | 5/2002 |
| WO | 2004/090165 | * | 10/2004 |
| WO | 2004/094651 A2 | | 11/2004 |
| WO | 2004/112214 A2 | | 12/2004 |
| WO | 2005/070400 A1 | | 8/2005 |
| WO | 2006/073419 A2 | | 7/2006 |
| WO | 2007/038755 A1 | | 4/2007 |
| WO | 2007/050501 A2 | | 5/2007 |
| WO | 2007/053655 A2 | | 5/2007 |
| WO | 2008/028206 A2 | | 3/2008 |
| WO | 2008/106660 A2 | | 9/2008 |
| WO | 2009/100201 A2 | | 8/2009 |
| WO | 2010/039496 A2 | | 4/2010 |
| WO | 2010/040897 A1 | | 4/2010 |
| WO | 2014/063097 A1 | | 4/2014 |
| WO | 2017/044899 A1 | | 3/2017 |
| WO | WO 2017/035326 A1 | | 3/2017 |
| WO | 2017/155837 A1 | | 9/2017 |
| WO | 2018/204421 A2 | | 11/2018 |

OTHER PUBLICATIONS

Advisory Action for U.S. Appl. No. 12/118,530. dated Jun. 6, 2012, 5 pages.
Aranyi T., et al., "Predictable Difficulty or Difficulty to Predict," *Protein Science*, Jan. 2011, vol. 20 (1), 3 pages.
Bacher G., et al., "Negative and Positive Ion Matrix-Assited Laser Desorption/Ionization Time-of- Flight Mass Spectrometry of Peptidoglycan Fragments Isolated from Various *Bacillus* Species," *Journal of Mass Spectrometry*, FEb. 2011, vol. 36 (2), 16 pages.
Bay et al., "Small multidrug resistance proteins: A multidrug transporter family that continues to grow," Biochimica et Biophysica Acta 1778 (2008) 1814-1838.
Bayburt T.H., et al., "Self-Assembly of Discoidal Phospholipid Bilayer Nanoparticles with Membrane Scaffold Protiens," Nano Letters, 2002, vol. 2, (8), 4 pages.
Beja O., et al., "Bacterial Rhodospin: Evidence for a New Type of Phototrophy in the Sea," *Science*, Sep. 2000, vol. 289 (5486), 6 pages.
Bockaert J., et al., "Do Recombinant Receptor Assays Provide Affinity and Potency Estimates?,"*In Receptor Classification: The Integration of Operational, Structural, and Transductional Information*, 1997, vol. 812, New York, New York Academy of Sciences, 16 pages.
Boldog T., et al., "Nanodiscs Separate Chemoreceptor Oligomeric States and Reveal Their Signalling Properties," *Proceedings of the National Academy of Sciences of the United States of America*, Aug. 2006, vol. 103 (31), 11509-11514. 6 pages.

(56) References Cited

OTHER PUBLICATIONS

Boldog T., et al., "Using Nanodiscs to Create Water-soluble Transmembrane Chemoreceptors Inserted in Lipid Bilayer," *Methods in Enzymology*,2007, vol. 423, 317-335. 19 pages.
Brodie E.L., et al., "Urban Aerosols Harbor Diverse and Dynamic Bacterial Populations," Proceedings of the National Academy of Sciences of the United States of America, Jan. 2007, vol. 104 (1), 299-304. 6 pages.
Burgdorf T., et al., "The Soluble NAD+-Reducing [NiFe]-Hydrogenase from Ralstonia eutropha H16 Consists of Six Subunits and can be Specifically Activated by NADPH," Journal of Bacteriology, May 2005, vol. 187 (9), 3122-3132. 11 pages.
Cappucchio J., et al., "Cell-free Co-expression of Functional Membrane Proteins and Apolipoprotein, Forming Soluble Nanolipoprotein Particles," Molecular and Cellular Proteomics, Nov. 2008, vol. 7 (11), 8 pages.
Casey P.J., et al., "Protein Prenyltransferases," *Journal of Biological Chemistry*, Mar. 1996, vol. 271 (10), 5289-5292. 5 pages.
Chefson A., et al., "Progress Towards the Easier Use of P450 Enzymes," *Molecular Biosystems*,Oct. 2006, vol. 2 (10), 462-469. 8 pages.
Cornish K., et al., "Characterization of Cis-Prenyl Transferase Activity Localised in a Buoyant Fraction of Rubber Particles From Ficus Elastica Latex," *Plant Physiology and Biochemistry*,May/Jun. 1996, vol. 34 (3), 377-384. 10 pages.
Cornish K., et al., "Natural Rubber biosynthesis in Plants: Rubber Transferase," Methods in Enzymology, 2012, vol. 515, 63-82. 20 pages.
Cornish K., et al., "Rubber Biosynthesis in Plants," American Oil Chemist Society, *The Lipid Library*, Nov. 2011, 10 pages.
Cullis P.R., et al., "Physical Properties and Functional Roles of Lipids in Membranes," *New Comprehensive Biochemistry*, 1991, vol. 20, 41 pages.
Das D., et al., "Role of Fe-hydrogenase in Biological Hydrogen Production," Current Science, Jun. 2006, vol. 90 (12), 1627-1637. 11 pages.
Denisov, I.G., et al., "Cytochromes P450 in Nanodiscs," Biochimica et Biophysica Act, 2010, 7 pages.
Dong, C., et al., "Regulation of G protein-coupled receptor export trafficking," Biochimica et Biophysica Acta 1768 (2006) 853-870.
Donninger C., et al., "An Improved Synthesis of Isopentenyl Pyrophosphate," The Biochemical Journal, Nov. 1967, vol. 105 (2), 545-547. 3 pages.
Dubey R., et al., "Microencapsulation Technology and Applications," Defence Science Journal, Jan. 2009, vol. 59 (1), 82-95. 14 pages.
Elgren T. E. et al., "Immobilization of Active Hydrogenases by Encapsulation in Polymeric Porous Gels," *Nano Letters*,Oct. 2005, vol. 5 (10), 2085-2087. 3 pages.
Final Office Action for U.S. Appl. No. 12/118,530. dated Jan. 25, 2012, 37 pages.
Final Office Action for U.S. Appl. No. 12/118,530. dated Mar. 6, 2015, 51 pages.
Final Office Action for U.S. Appl. No. 12/352,472. dated Jun. 7, 2012, 25 pages.
Final Office Action for U.S. Appl. No. 12/352,472. dated Jun. 29, 2015, 18 pages.
Friedrich T. et al., "The respiratory complex I of bacteria, archaea and eukarya and its module common with membrane-bound multisubunit hydrogenases." FEBS Lett. Aug. 2000 11;479(1-2):1-5.
G Protein-coupled Receptor[online], Retrieved from the Internet: URL: Wikipedia 2008, https://web.archive.org/web/20080224232212/:///en.wikipedia.org/wiki/G.protein-coupled.receptor, 2008, 7 pages.
Gan L., et al., "Role of NADPH-Cytochrome P450 Reductase and Cytochrome-b-5/NADH-b5 Reductase in Variability of CYP3A Activity in Human Liver Microsomes," *Drug Metabolism and Disposition*, Jan. 2009, vol. 37 (1), 90-96. 7 pages
Gilbert L., "Insect Development: Morphognesis, molting and Metamorphosis," *Academic Press*,Sep. 18, 2009, 573-574. 2 pages.
Gorrod J.W., et al., "Some Observations on Type I and Type II Microsomal Binding Spectra," *Xenobiotica*, Jul.-Oct. 1971, vol. 1 (4), 521-522. 2 pages.
Greve, H-H., "Rubber, 2. Natural" in *Ullmann's Encyclopedia of Industrial Chemistry*vol 31 (2012) 583-596. Wiley-VCH Verlag Gmbh & Co. KGaA, Weinheim, 14 pages.
Grinkova, Y.V., et al., "Engineering extended membrane scaffold proteins for self-assembly of soluble nanoscale lipid bilayers," Protein Engineering, Design and Selection, 2010, vol. 23, No. 11, pp. 843-848.
Gronover C.S., et al., "Natural Rubber Biosynthesis and Physics-Chemical Studies on Plant Derived Latex," *Biotechnology of Biopolymers*,Jul. 2011, 75-88. 15 pages.
Hallenbeck P.C. et al., "Biological Hydrogen Production: Fundamentals and Limiting Processes," *International Journal of Hydrogen Energy*,Nov. 2002, vol. 27 (11-12), 1185-1193. 9 pages.
Hasemann C.A., et al., "Structure and Function of Cytochromes P450: a Comparative Analysis of Three Crystal Structures," *Structure*, Jan. 1995, vol. 3 (1), 22 pages.
Hiraishi T., et al., "Enzyme-catalyzed Synthesis and Degradation of Biopolymers," *Mini-Reviews in Organic Chemistry*, Bentham Science Publishers, Feb. 2009, vol. 6 (1), 11 pages.
Ho D., et al., "Fabrication of Biomolecule-copolymer Hybrid Nanovesicles as Energy Conversion Systems," *Nanotechnology*,Nov. 2005, vol. 16 (12), 13 pages.
International Preliminary Report on Patentability for Application No. PCT/US2008/063307, dated Nov. 10, 2009, 7 pages.
International Search Report for Application No. PCT/US2008/063307, dated Oct. 29, 2008, 5 pages.
"Ion channel", Wikipedia, accessed Dec. 22, 2014, pp. 1-8, 8 pages.
Katzen F., et al., "Insertion of Membrane Proteins Into Discoidal Membranes Using a Cell-free Protein Expression Approach," Journal of Proteome Research, Aug. 2008, vol. 7 (8), 8 pages.
Kurkin S., et al., "The Membrane-bound [NiFe]-hydrogenase (Ech) From Methanosarcina Barkeri: Unusual Properties of the Iron-sulphur Clusters," *European Journal of Biochemistry*,Dec. 2002, vol. 269 (24), 6101-6111. 11 pages.
Lechene C., et al., "High-resolution Quantitative Imaging of Mammalian and Bacterial Cells Using Stable Isotope Mass Spectrometry," *Journal of Biology*,2006, vol. 5 (6), article 20, 30 pages.
Leitz A.J., et al., "Functional Reconstitution of Beta2-adrenergic Receptors Utilizing Self-assembling Nanodisc Technology," *Biotechniques*,May 2006, vol. 40 (5), 6 pages.
Long M., et al., "Characterization of a HoxEFUYH type of [NiFe] Hydrogenase from Allochromatium Vinosum and Some EPR and IR Properties of the Hydrogenase Module," *Journal of Biological Inorganic Chemistry*, Jan. 2007, vol. 12 (1), 18 pages.
McIntosh C.L., et al., "The [NiFe]-Hydrogenase of the *Cyanobacterium synechocystis* sp. PCC 6803 Works Bidirectionally with a Bias to H2 Production, "*Journal of the American Chemical Society*, Jun. 2011, vol. 133 (29), 12 pages.
McTernan P.M., et al., "Intact Functional Fourteen-Subunit Respiratory Membrane-Bound [NiFe]-Hydrogenase Complex of the Hyperthermophilic Archaeon Pyrococcus Furiosus," *Journal of Biological Chemistry*,Jul. 2014, vol. 289 (28), 10 pages.
Meuer J., et al., "Purification and Catalytic Properties of Ech Hydrogenase From Methanosarcina Barkeri," *European Journal of Biochemistry*, Oct. 1999, vol. 265 (1), 11 pages.
Meyer J., "[Fe/Fe] Hydrogenases and Their Evolution: A Genomic Perspective," *Cellular and Molecular Life Sciences*,May 2007, vol. 64 (9), 1063-1084. 22 pages.
Nath A et al., "Applications of Phospholipid Bilayer Nanodiscs in the Study of Membranes and Membrane Proteins," Biochemistry, Feb. 2007, vol. 46 (8), 11 pages.
Non-Final Office Action for U.S. Appl. No. 12/118,530. dated Aug. 30, 2011, 28 pages.
Non-Final Office Action for U.S. Appl. No. 12/118,530. dated Jul. 24, 2014, 33 pages.
Non-Final Office Action for U.S. Appl. No. 12/352,472. dated Aug. 12, 2016, 31 pages.
Non-Final Office Action for U.S. Appl. No. 12/352,472. dated Dec. 26, 2014, 24 pages.

(56) References Cited

OTHER PUBLICATIONS

Non-Final Office Action for U.S. Appl. No. 12/352,472. dated Oct. 2, 2013, 19 pages.
Non-Final Office Action for U.S. Appl. No. 12/352,472. dated Sep. 22, 2011, 21 pages.
North P., et al., "Alteration of Synaptic Membrane Cholesterol/Phospholipid Ratio Using a Lipid Transfer Protein, Effect on Gamma-aminobutyric Acid Uptake," *The Journal of Biological Chemistry*, Jan. 1983, vol. 258 (2), 12 pages.
Notice of Allowance for U.S. Appl. No. 12/352,472. dated Mar. 17, 2017, 12 pages.
Ohya N., et al., "Biosynthesis of Natural Rubber and Other Natural Polyisoprenoids," Biopolymers Polyisoprenoids, Jan. 2005, 73-81. 9 pages.
Pan Z., et al., "The Major Protein of Guayule Rubber Particles is a Cytochrome P450: Characterization based on cDNA Cloning and Spectroscopic Analysis of the Solubilized Enzyme and Its Reaction Products," The Journal of Biological Chemistry, Apr. 1995, vol. 270 (15), 8487-8494. 8 pages.
Pasini E.M., et al., "In-Depth Analysis of the Membranes and Cytosolic Proteome of Red Blood Cells," Blood, Aug. 2006, vol. 180 (3), 12 pages.
Paterson-Jones J.C., et al., "The Biosynthesis of Natural Rubber," Journal of Plant Physiology, Jun. 1990, vol. 136 (3), 7 pages.
Persson B., et al., "Topology Prediction of Membrane Proteins," Protein Science, Feb. 1996, vol. 5 (2), 9 pages.
Ponciano G., et al., "Transcriptome and Gene Expression Analysis in Cold-Acclimated Guayule (*Parthenium argentum*) Rubber-Producing Tissue," Phytochemistry, Jul. 2012, vol. 79, 12 pages.
Rakhely G., et al., "Cyanobacterial-Type, Heteropentameric, NAD+-Reducing NiFe Hydrogenase in the Purple Sulfur Photosynthetic Bacterium Thiocapsa Roseopersicina," Applied and Environmental Microbiology, Feb. 2004, vol. 70 (2), 7 pages.
Rapp V. et al., "Predicting Fuel Performance for Future HCCI Engines" Combust. Sci. Technol., 185: 735-748, Apr. 20, 2013. 15 pages.
Restriction Requirement for U.S. Appl. No. 12/118,530, filed May 9, 2008. dated Sep. 24, 2010, 14 pages.
Restriction Requirement for U.S. Appl. No. 12/118,530. dated Mar. 30, 2011, 28 pages.
Restriction Requirement for U.S. Appl. No. 12/352,472. dated May 27, 2011, 8 pages.
Sabatini, D.D., et al., "Mechanisms for the Incorporation of Proteins in Membranes and Organelles," Jan. 1, 1982, The Journal of Cell Biology, vol. 92, 1-22.
Sanderson K., "Chemistry: The Photon Trap," Nature, Mar. 27, 2008, vol. 452(7186), 3 pages.
Sapra R., et al., "A Simple Energy-Conserving System: Proton Reduction Coupled to Proton Translocation," Proceedings of the National Academy of Sciences of the United States of America, Jun. 24, 2003, vol. 100(13), 6 pages.
Sapra R., et al., "Purification and Characterization of a Membrane-Bound Hydrogenase from the Hyperthermophilic Archaeon Pyrococcus Furiosus," Journal of Bacteriology, Jun. 2000, vol. 182(12), 6 pages.
Schmidt T., et al., "Characterization of Rubber Particles and Rubber Chain Elongation in Taraxacum Koksaghyz," BMC Biochemistry, Feb. 19, 2010, vol. 11, 11 pages.
Schmitz O., et al., "HoxE—A Subunit Specific for the Pentameric Bidirectional Hydrogenase Complex (HoxEFUYH) of Cyanobacteria," Biochimica et Biophysica Acta, Apr. 22, 2002, vol. 1554(1-2), 9 pages.
Shih A.Y., et al., "Molecular Dynamics Simulations of Discoidal Bilayers Assembled from Truncated Human Lipoproteins," *Biophysical Journal*, Jan. 2005, vol. 88 (1), 9 pages.
Siler D.J., et al., "Composition of Rubber Particles of Hevea Brasiliensis, Parthenium Argentatum, Ficus Elastics and Euphorbia Lactiflua Indicates Unconventional Surface Structure," Plant Physiology and Biochemistry, Jan. 1997, vol. 35 (11), 9 pages.

Silvius J.R., "Thermotropic Phase Transitions of Pure Lipids in Model Membranes and their Modification by Membrane Proteins," Lipid-Protein Interactions, 1982, vol. 2, pp. 239-281, 43 pages.
Singer, S.J., et al., "The Fluid Mosaic Model of the Structure of Cell Membranes," Feb. 1972, Science, vol. 175, 720-731.
Singh A.P., et al., "The Micromorphology and Protein Characterization of Rubber Particles in Ficus Carica, Ficus Benghalensis and Hevea Brasiliensis," Journal of Experimental Botany, Mar. 2003, vol. 54 (384), 8 pages.
Smith D. et al., "Solubilisation of methane monooxygenase from Methylococcus capsulatus (Bath)" Eur. J. Biochem, 182, pp. 667-671, Jan. 17, 1989, 6 pages.
Soboh B., et al., "Purification and Catalytic Properties of a CO-Oxidizing: H2-Evolving Enzyme Complex from Carboxydothermus Hydrogenoformans," European Journal of Biochemistry, Nov. 2002, vol. 269 (22), 10 pages.
Stadermann F.J., et al., "Nanosims: The Next Generation Ion Probe for the Microanalysis of Extra Terrestrial Material," Meteoritics and Planetary Science, 36342, vol. 34 (4), 1999. 2 pages.
Stryer L., et al., "Oxygen Binds to a Heme Prosthetic Group: Biochemistry," 1995, 4th edition, 1 page.
Sun P.D., et al., "Overview of Protein Structural and Functional Folds," *Current Protocols in Protein Science*, May 2004, vol. 35, 3 pages.
Vincent K. A., et al., "Electrocatalytic Hydrogen Oxidation by an Enzyme at High Carbon Monoxide or Oxygen Levels," *Proceedings of the National Academy of Sciences*, Nov. 2005, vol. 102 (47), 4 pages.
Vincent K. A., et al., "Investigating and Exploiting the Electrocatalytic Properties of Hydrogenases, "*Chemical Reviews*,2007, vol. 107 (10), 48 pages.
Whalen M., et al., "Development of Crops to Produce Industrially Useful Natural Rubber," *Isoprenoid Synthesis in Plants and Microorganisms*,Jan. 2013, vol. 23, 17 pages.
White, S., Membrane Protein Insertion: The Biology-Physics Nexus, Apr. 16, 2007, J. Gen. Physiol., vol. 129, No. 5, 363-369.
Wikipedia—Bacteriorhodopsin, 2 pages, (Downloaded from the internet on Jun. 22, 2015).
Wikipedia., Hydrogenase retrieved from en.wikipedia.org/wiki/Hydrogenase on Nov. 6, 2012, 4 pages.
Woodward J., et al., "Enzymatic Production of Biohydrogen," *Nature*, Jun. 2000, vol. 405 (6790), 2 pages.
Woodward J., et al., "In Vitro Hydrogen Production by Glucose Dehydrogenase and Hydrogenase," *Nature Biotechnology*,Jul. 1996, vol. 14 (7), 3 pages.
Written Opinion for Application No. PCT/US2008/063307, dated Oct. 29, 2008, 6 pages.
Wu, L., et al., "Membrane targeting and translocation of bacterial hydrogenases," 2000, Arch Microbiology, 173:319-324.
Xie W., et al., "Initiation of Rubber Biosynthesis: In Vitro Comparisons of Benzophenone-Modified Diphosphate Analogues in Three Rubber-Producing Species," *Phytochemistry*, Oct. 2008, vol. 69 (14), 7 pages.
Zhang Y.H., et al., "High-Yield Hydrogen Production from Starch and Water by a Synthetic Enzymatic Pathway," *PLoS One*, May 2007, vol. 2 (5), e456, 6 pages.
Zhanhua C., et al., "Protein Subunit Interfaces: Heterodimers versus Homodimers," *Bioinformation*,Aug. 2005, vol. 1 (2), 12 pages.
Bezrukov S. M. "Functional consequences of lipid packing stress" Current Opinion Colloid & Interface Science 5, Jan. 2000, pp. 237-243.
Denisov I. G. "Thermotropic Phase Transition in Soluble Nanoscale Lipid Bilayers" J Phys Chem B., Aug. 18, 2005, 109(32), pp. 15580-15588. 23 pages.
"Drug" Wikipedia, the free encyclopedia. Downloaded through the Wayback Machine for Dec. 8, 2011. 5 pages.
Final Office Action for U.S. Appl. No. 15/755,018 filed Feb. 23, 2018 on behalf of Lawrence Livermore National Security, LLC dated Dec. 27, 2021 18 pages.
Final Office Action for U.S. Appl. No. 16/082,924 filed Sep. 6, 2018 on behalf of Lawrence Livermore National Security, LLC dated Jan. 25, 2022 21 pages.

(56) References Cited

OTHER PUBLICATIONS

Martinez D. et al., "Lipid Internal Dynamics Probed in Nanodiscs" ChemPhysChem, Jan. 2017, 18, pp. 2651-2657.
Klevens H. B. "Structure and Aggregation in Dilute Solutions of Surface Active Agents" The Journal of the American Oil Chemists Society, Feb. 1953, pp. 74-80. 7 pages.
Notice of Allowability for U.S. Appl. No. 16/159,189, filed Oct. 12, 2018, on behalf of Lawrence Livermore National Security, LLC. dated Dec. 21, 2021. 4 Pages.
Notice of Allowance for U.S. Appl. No. 15/744,754, filed Jan. 12, 2018 on behalf of Lawrence Livermore National Security, LLC. dated Nov. 22, 2021 11 pages.
Notice of Allowance for U.S. Appl. No. 16/159,189, filed OCt. 12, 2018 on behalf of Lawrence Livermore National Security, LLC. dated Dec. 9, 2021. 10 pages.
Notice of Allowance for U.S. Appl. No. 16/609,420, filed Oct. 29, 2019 on behalf of Lawrence Livermore National Laboratory. dated Nov. 10, 2021. 7 Pages.
Pollock, N.L. et al., "Structure and function of membrane proteins encapsulated in a polymer-bound lipid bilayer", Biochimica et Biophysica Acta (BBA)—Biomembranes (Apr. 2018), vol. 1860, Issue 4, pp. 809-817, 9 pages; Internet: dx.doi.org/10.1016/j.bbamem.2017.08.012.
Schachter T. et al., "Confinement in Nanodiscs Anisotropically Modifies Lipid Bilayer Elastic Properties" J. Phys. Chem. B, Jul. 2020, vol. 124, pp. 7166-7175.
Schuler M. et al., "Nanodiscs as a new tool to examine lipid-protein interactions" *Methods Mol Biol.*, 2013; 974, pp. 415-433.
Shelby M. et al., "Cell-Free Co-Translational Approaches for Producing Mammalian Receptors: Expanding the Cell-Free Expression Toolbox Using Nanolipoproteins" Frontiers in Pharmacology, vol. 10 No. 744, Jul. 2019, pp. 1-12.
Stepien P. et al., "Comparative EPR studies on lipid bilayer properties in nanodiscs and liposomes" *Biochimica et Biophysica Acta*, 1848, Oct. 2014, pp. 60-66.
Tanaka, M. et al. "Preparation and Characterization ofReconstituted Lipid-Synthetic Polymer Discoidal Particles" Langmuir, (2015), vol. 31, Issue 46, 12719-12726. 8 pages. Internet: doi. 10.1021/acs.langmuir.5b03438.
Aina O.H., et al., "From combinatorial chemistry to cancer-targeting peptides" Mol Pharm, vol. 4, No. 5, pp. 631-651 (2007).
Bacher G., et al., "Charge-reduced Nano Electrospray Ionization Combined with Differential Mobility Analysis of Peptides, Proteins, Glycoproteins, Noncovalent Protein Complexes and Viruses," Journal of Mass Spectrometry, Sep. 2001, vol. 36 (9), 1038-1052. 15 pages.
Baker S.E., et al., "Hydrogen Production by a Hyperthermophilic Membrane-Bound Hydrogenase in Water Soluble Nanolipoprotein Particles," Journal of the American Chemical Society, Nov. 18, 2008, vol. 131 (22), 15 pages.
Barros F., et al., "Modulation of Human erg K+ Channel Gating by Activation of a G Protein- Coupled Receptor and Protein Kinase C," The Journal of Physiology, Sep. 1998, vol. 511 (Pt 2), 333-346. 14 pages.
Bayburt T.H., et al., "Self-Assembly of Discoidal Phospholipid Bilayer Nanoparticles with Membrane Scaffold Proteins," Nano Letters, 2002, vol. 2 (8), 853-856. 11 pages (Additional Pages of Accompanying Online Supplementary Information).
Behrens S., et al., "Linking Microbial Phylogeny to Metabolic Activity at the Single-cell Level by Using Enhanced Element Labeling-Catalyzed Reporter Deposition Fluorescence in Situ Hybridization (EL-FISH) and Nanosims," Applied and Environmental Microbiology,May 2008, vol. 74 (10), 3143-3150. 8 pages.
Berthelot K., et al., "Rubber Elongation Factor (REF), a Major Allergen Component in Hevea Brasiliensis Latex Has Amyloid Properties," PLoS One,2012, vol. 7 (10), e48065. 12 pages.
Bijsterbosch M.K., et al., "Specific Targeting of a Lipophilic Prodrug of Iododeoxyuridine to Parenchymal Liver Cells Using Lactosylated Reconstituted High Density Lipoprotein Particles," Biochemical Pharmacology,Jul. 1996, vol. 52 (1), 113-121. 10 pages.

Bischler N., et al., "Specific Interaction and Two-Dimensional Crystallization of Histidine Tagged Yeast RNA Polymerase I on Nickel-Chelating Lipids," Biophysical Journal, Mar. 1998, vol. 74 (3), 1522-1532. 11 pages.
Blanchette C.D., et al., "Kinetic analysis of his-tagged protein binding to nickel-chelating nanolipoprotein particles." Bioconjug Chem, 21, pp. 1321-1330(Jul. 2010).
Blanchette C.D., et al., "Quantifying Size Distributions of Nanolipoprotein Particles With Single-particle Analysis and Molecular Dynamic Simulations," Journal of Lipid Research, Jul. 2008, vol. 49 (7), 11 pages.
Borch J., et al., "Nanodiscs for Immobilization of Lipid Bilayers and Membrane Receptors: Kinetic Analysis of Cholera Toxin Binding to a Glycolipid Receptor," Analytical Chemistry,Aug. 2008, vol. 80 (16), 8 pages.
Boroske E., et al., "Osmotic Shrinkage of Giant Egg-Lecithin Vesicles," Biophysical Journal, Apr. 1981, vol. 34 (1), 95-109. 15 pages.
Boschker H.T.S., et al., "Direct Linking of Microbial Populations to Specific Biogeochemical Processes by 13C-Labelling of Biomarkers," Nature , Apr. 1998, vol. 392, 801-805. 5 pages.
Branden et al., "Introduction to Protein Structure," 2nd edition, Garland Science Publisher, 1999, pp. 3-12. 11 pages.
Brewer S.H., et al., "Formation of Thiolate and Phosphonate Adlayers on Indium-Tin Oxide: Optical and Electronic Characterization," Langmuir,2002, vol. 18 (18), 6857- 6865. 9 pages.
Brodie E.L., et al., "Application of a High-Density Oligonucleotide Microarray Approach To Study Bacterial Population Dynamics during Uranium Reduction and Reoxidation," Applied and Environmental Microbiology, Sep. 2006, vol. 72 (9), 6288-6298. 11 pages.
Brodie E.L., et al., "Profiling Microbial Identity and Activity: Novel Applications of NanoSIMS and High Density Microarrays," Systems Biology Research Strategy & Technology Development, Genomics: GTL Awardee Workshop VI, Department of Energy,2008, 2 pages.
Brodie et al., Systems Biology Research Strategy and Technology Development: Genomic and Proteomic Strategies. Publicly disclosed on Feb. 13, 2008, http://genomicscience.energy.gov/pubs/2008abstracts/2008GTLabstractstech.pdf, 48 pages.
Brown P.O., et al., "Exploring the New World of the Genome with DNA Microarrays," Nature Genetics,Jan. 1999, vol. 21 (1 Suppl), 33-37. 5 pages.
"Catalytic oxygen removal from coal mine methane, "http://www.digitalrefining.com/article/1000623,Catalytic_oxygen_remo-val_from_coal_mine_methane.html# . . . , accessedNov. 27, 2017, 4 pages.
Chaung H.C., et al., "CpG Oligodeoxynucleotides as DNA Adjuvants in Vertebrates and their Applications in Immunotherapy," International Immunopharmacology,Oct. 2006, vol. 6 (10), 1586-1596. 11 pages.
Chikh G.G., et al., "Attaching Histidine-Tagged Peptides and Proteins to Lipid-Based Carriers Through Use of Metal-Ion-Chelating Lipids," Biochimica et Biophysica Acta, Dec. 2002, vol. 1567 (1-2), 204-212. 9 pages.
Claypool et al., An ethanol/ether soluble apoprotein from rat lung surfactant augments liposome uptake by isolated granular pneumocytes. J Clin Invest. Sep. 1984; 74(3): 677-84. (Year: 1984). 8 pages.
Cline M.S., et al., "Integration of Biological Networks and Gene Expression Data Using Cytoscape," Nature Protocols, 2007, vol. 2 (10), 2366-2382. 17 pages.
Cornish K., "Biochemistry of Natural Rubber, a Vital Raw Material, Emphasizing Biosynthetic Rate, Molecular Weight and Compartmentalization, in Evolutionarily Divergent Plant Species," Natural Product Reports, Apr. 2001, vol. 18 (2), 182-189. 8 pages.
Co-Translation of Iintegral Membrane Proteins (MP) with Membrane Scaffoldproteins (MSP), also known as Nanodiscs[online], Jul. 2015 [ retrieved on Jul. 1, 2015]. Retrieved from the Internet: URL: http://technology.sbkb.org/portal/page/329/, 3 pages.
Cracknell J.A., et al., "Enzymatic Oxidation of H2 in Atmospheric O2: The Electrochemistry of Energy Generation from Trace H2 by Aerobic Microorganisms," Journal of the American Chemical Society, Jan. 2008, vol. 130 (2), 424-425. 2 pages.

(56) References Cited

OTHER PUBLICATIONS

Cravatt B.R., et al., "Large-Scale Profiling of Protein Palmitoylation in Mammalian Cells," Nature Methods, Feb. 2009, vol. 6 (2), 135-138. 4 pages.

Cube Biotech, "Assembly of Nanodiscs for use in Cell-Free Expression using MSP1D1 Protein and POPC Phospholipids,"2014, 3 pages.

Cube Biotech, "Nanodisc Assembly Kit MSP1E3D1_POPC, "Dec. 2014, 3 pages.

Dalpke A.H., et al., "Phosphodiester CpG Oligonucleotides as Adjuvants:Polyguanosine Runs Enhance Cellular Uptake and Improve Immunostimulative Activity of Phosphodiester CpG Oligonucleotides in Vitro and in Vivo," Immunology, May 2002, vol. 106 (1), 102-112. 11 pages.

Das D., et al., "Hydrogen Production by Biological Processes: A Survey of Literature," International Journal of Hydrogen Energy,Jan. 2001, vol. 26 (1), 13-28. 16 pages.

Desantis T.Z., et al., "Greengenes, a Chimera-checked 16S rRna Gene Database and Workbench Compatible with ARB," Applied and Environmental Microbiology,Jul. 2006, vol. 72 (7), 5069-5072. 5 pages.

Desantis T.Z., et al., "High-Density Universal 16S rRNA Microarray Analysis Reveals Broader Diversity than Typical Clone Library When Sampling the Environment," Microbial Ecology, Apr. 2007, vol. 53 (3), 371-383. 13 pages.

Disalvo E.A., et al., "Surface Changes Induced by Osmotic Shrinkage on Large Unilamellar Vesicles," Chemistry and Physics of Lipids,Nov. 1996, vol. 84 (1), 35-45. 11 pages.

Duan H., et al., "Co-Incorporationof Heterologously Expressed *Arabidopsis cytochrome* P450 and P450 Reductase into Soluble Nanoscale Lipid Bilayers," Archives of Biochemistry and Biophysics, Apr. 2004, vol. 424 (2), 141-153. 13 pages.

Dumartin B., et al., "Dopamine Tone Regulates D1 Receptor Trafficking and Delivery in Striatal Neurons in Dopamine Transporter-Deficient Mice," Proceedings of the National Academy of Sciences of the United States of America, Feb. 2000, vol. 97 (4), 1879-1884. 6 pages.

Eberly J.O., et al., "Thermotolerant Hydrogenases: Biological Diversity, Properties and Biotechnical Applications," Critical Reviews in Microbiology,Dec. 2008, vol. 34 (3-4), 117-130. 14 pages.

Final Office Action for U.S. Appl. No. 14/861,750dated Feb. 23, 2018, 21 pages.

Fischer N.O., et al., "Conjugation to Nickel-Chelating Nanolipoprotein Particles Increases the Potency and Efficacy of Subunit Vaccines to Prevent West Nile Encephalitis," Bioconjugate Chemistry, Jun. 2010, vol. 21 (6), 1018-1022. 5 pages.

Fischer N.O., et al., "Evaluation of Nanolipoprotein Particles (NLPs) as an In Vivo Delivery Platform," Plos One,Mar. 2014, vol. 9 (3), e93342, 1-17. 17 pages.

Fischer N.O., et al., "Immobilization of His-Tagged Proteins on Nickel-Chelating Nanolipoprotein Particles," Bioconjugate Chemistry,Mar. 2009, vol. 20 (3), 460-465. 6 pages.

Fitzgerald K.A., et al., "The Shape of Things to Come," Science,Jun. 2007, vol. 316 (5831), 1574-1576. 4 pages.

Gantz I., et al., "Molecular Cloning of a Gene Encoding the Histamine H2 Receptor," Proceedings of the National Academy of Sciences of the United States of America, Jan. 1991, vol. 88 (2), 429-433. 6 pages.

Gardner T.J., et al., "Systems for Orthogonal Self-assembly of Electroactive Monolayers on Au and ITO: an Approach to Molecular Electronics," Journal of American Chemical Society, Jul. 1995, vol. 117 (26), 6927-6933. 7 pages.

Giannini S.L., et al., "Enhanced Humoral and Memory B Cellular Immunity Using HPV16/18 L1 VLP Vaccine Formulated With the MPL/aluminium Salt Combination (AS04) Compared to Aluminium Salt Only," Vaccine,Aug. 2006, vol. 24 (33-34), 13 pages.

Goldet G., et al., "Hydrogen Production under Aerobic Conditions by Membrane-Bound Hydrogenases from Ralstonia Species, "Journal of American Chemical Society, Jul. 2008, vol. 130 (33), 9 pages.

Guo H.H., et al., "Protein Tolerance to Random Amino Acid Change,"*Proceedings of the National Academy of Sciences of the United States of America*, Jun. 2004, vol. 101 (25), 6 pages.

Gupta R.K ., et al., "Adjuvants for Human Vaccines—current Status, Problems and Future Prospects," Vaccine, Oct. 1995, vol. 13 (14), 14 pages.

Hamdy S., et al., "Pharmaceutical Analysis of Synthetic Lipid a-based Vaccine Adjuvants in Poly (D, L-lactic-co-glycolic Acid) Nanoparticle Formulations,"*Journal of Pharmaceutical and Biomedical Analysis*, Aug. 2007, vol. 44 (4), 10 pages.

Hedderich R., "Energy-converting [NiFe] Hydrogenases From Archaea and Extremophiles: Ancestors of Complex I,"*Journal of Bioenergetics and Biomembranes*, Feb. 2004, vol. 36 (1), 11 pages.

Hernandez-Caselles T., et al., "Influence of Liposome Charge and Composition on Their Interaction With Human Blood Serum Proteins, "*Molecular and Cellular Biochemistry*, Mar. 1993, vol. 120 (2), 8 pages.

Hill M.A., et al., "Functional Analysis of Conserved Histidines in ADP-glucose Pyrophosphorylase From *Escherichia coli,"Biochemical and Biophysical Research Communications*, Mar. 1998, vol. 244 (2), 5 pages.

Hong Y., et al., "G-protein-coupled Receptor Microarrays for Multiplexed Compound Screening,"*Journal of Biomolecular Screening*, Jun. 2006, vol. 11 (4), 4 pages.

Huleatt J.W., et al., "Potent Immunogenicity and Efficacy of a Universal Influenza Vaccine Candidate Comprising a Recombinant Fusion Protein Linking Influenza M2e to the TLR5 Ligand Flagellin," Vaccine, Jan. 2008, vol. 26 (2), 14 pages.

International Preliminary Report on Patentability for Application No. PCT/US2009/044722, dated Nov. 23, 2010, 7 pages.

International Preliminary Report on Patentability for Application No. PCT/US2015/051516 filed Sep. 22, 2015 on behalf of Lawrence Livermore National Security, LLC.dated Mar. 28, 2017, 10 pages. (English Only).

International Search Report and Written Opinion for Application No. PCT/US2015/051516 filed on Sep. 22, 2015.dated Jan. 25, 2016, 12 pages.

International Search Report for Application No. PCT/US2009/044722, dated Oct. 28, 2010, 4 pages.

Jasanada F., et al., "Indium-111 Labeling of Low Density Lipoproteins With the DTPA-bis(Stearylamide): Evaluation as a Potential Radiopharmaceutical for Tumor Localization,"*Bioconjugate Chemistry*, Jan.-Feb. 1996, vol. 7 (1), 10 pages.

Kapdan I.K., et al., "Bio-hydrogen Production from Waste Materials, "*Enzyme and Microbial Technology*, Mar. 2006, vol. 38 (5), 14 pages.

Keppetipola S, et al., From gene to HSQC in under five hours: high-throughput NMR proteomics: J Am Chem Soc, 128, pp. 4508-4509(Apr. 2006).

Kigawa T, et al., "Cell-free production and stable-isotope labeling of milligram quantities of proteins" FEBS Lett, 442, pp. 15-19(Jan. 1999).

Kolb H.C., et al., "The Growing Impact of Click Chemistryon Drug Discovery, "*Drug Discovery Today*,Dec. 2003, vol. 8 (24), 10 pages.

Konishi E., et al., "Proper Maturation of the Japanese Encephalitis Virus Envelope Glycoprotein Requires Cosynthesis with the Premembrane Protein,"*Journal of Virology*, Mar. 1993, vol. 67 (3), 4 pages.

Kostarelos K., et al., "Steric Stabilization of Phospholipid Vesicles by Block Copolymers Vesicle Flocculation and Osmotic Swelling Caused by Monovalent and Divalent Cations,"*Journal of the Chemical Society*, Faraday Transactions,Aug. 1998, vol. 94, 10 pages.

Kovacs K., et al., "A Novel Approach for Biohydrogen Production," *International Journal of Hydrogen Energy*,Sep. 2006, vol. 31 (11), 9 pages.

Kubalek E.W., et al., "Two-dimensional Crystallization of Histidine-tagged, HIV-1 Reverse Transcriptase Promoted by a Novel Nickel-chelating Lipid,"*Journal of Structural Biology*,Sep.-Oct. 1994, vol. 113 (2), 7 pages.

Langworthy, T.A., "Lipids of Thermoplasma,"1982, Methods in Enzymology, vol. 88, 396-406.

Lasic D.D., "Novel Applications of Liposomes," *Trends in Biotechnology*, Jul. 1998, vol. 16 (7), 15 pages.

(56) References Cited

OTHER PUBLICATIONS

Lazar E., et al., "Transforming Growth Factor Alpha: Mutation of Aspartic Acid 47 and Leucine 48 Results in Different Biological Activities, "*Molecular and Cellular Biology*,Mar. 1988, vol. 8 (3), 6 pages.

Liang X., et al., "Mechanical Properties and Stability Measurement of Cholesterol-containing Liposome on Mica by Atomic Force Microscopy, "*Journal of Colloid and Interface Science*, Oct. 2004, vol. 278 (1), 10 pages.

Lluis M.W., et al., "Protein Engineering Methods Applied to Membrane Protein Targets, "*Protein Engineering, Design & Selection*,Feb. 2013, vol. 26 (2), 10 pages.

Lodish H., et al., "Section 17.5 Insertion of Membrane Proteins into the ER Membrane,"*Molecular Cell Biology*, 4th edition, New York, NY.,2000, 9 pages.

Ludwig W., et al., "ARB: A Software Environment for Sequence Data,"*Nucleic Acids Research*,Feb. 2004, vol. 32 (4), 9 pages.

Luo J, et al., "Well-defined, size-tunable, multifunctional micelles for efficient paclitaxel delivery for cancer treatment." Bioconjug Chem, 21, pp. 1216-1224(Jul. 2010).

Ma, K., et al., "Characterization of Hydrogenase II from the Hyperthermophilic Archaeon Pyrococcus furiosus and Assessment of Its Role in Sulfur Reduction,"Apr. 2000, Journal of Bacteriology, vol. 182, No. 7, 1864-1871.

Manefield M., et al., "RNA Stable Isotope Probing, a Novel Means of Linking Microbial Community Function to Phylogeny, " *Applied and Environmental Microbiology*,Nov. 2002, vol. 68 (11), 7 pages.

Marshall, G.R., et al., "Conformational effects of chiral a,a-dialkyl amino acids, "1988, Int. J. Peptide Protein Res., 32, 544-555.

Masquelier M., et al., "Low-density Lipoprotein as a Carrier of Antitumoral Drugs: in Vivo Fate of Drug-human Low-density Lipoprotein Complexes in Mice," Cancer Research, Aug. 1986, vol. 46 (8), 6 pages.

Mata-Haro V., et al., "The Vaccine Adjuvant Monophosphoryl Lipid A as a TRIF-Biased Agonist of TLR4,"*Science*, Jun. 2007, vol. 316 (5831), 7 pages.

McGall G.H., et al., "The Efficiency of Light-Directed Synthesis of DNA Arrays on Glass Substrates,"*Journal of the American Chemical Society*, Jun. 1997, vol. 119 (22), 10 pages.

Metz J., et al., "ACTH, α-MSH, and Control of Cortisol Release: Cloning, Sequencing, and Functional Expression of the Melanocortin-2 and Melanocortin-5 Receptor in Cyprinus Carpio,"*American Journal of Physiology Regulatory Integrative and Comparative Physiology*,May 2005, vol. 289, 13 pages.

Mori M, et al., "Cell-free synthesis and processing of a putative precursor for mitochondrial carbamyl phosphate synthetase I of rat liver" Proc Natl Acad Sci USA, vol. 76, No. 10, pp. 5071-5075(Oct. 1979).

Moses S., et al., "Detection of DNA Hybridization on Indium Tin Oxide Surfaces,"*Sensors and Actuators* 2007, vol. 125 (2), 7 pages.

Muscarinic Acetylcholine Receptor, Retrieved from the Internet: URL://web.archive.org/web/20071020193657//https://en.wikipedia.org/wiki/Muscarinic_acetylcholine_receptor, Wikipedia2007, 6 pages.

Nanodisc Formation. LIAO Lab, Department of Cellbiology, Harvard Medical School, retrieved onAug. 3, 2015, from the Internet: URL:https://liao.hms.harvard.edu/node/34, 2 pages.

Nanodisc. Kobo eBook Library, Retrieved from the Internet: URL: http://www.kobolibrary.com/articles/nanodisc, retrieved onAug. 4, 2015, 4 pages.

Newpoint Gas "O2 Removal Services", https://www.newpointgas.com/services/oxygen-o2-removal/,2017, 4 pages.

Non-Final Office Action for U.S. Appl. No. 14/199,973.dated May 6, 2015, 34 pages.

Non-Final Office Action for U.S. Appl. No. 14/861,750.dated Aug. 25, 2017, 23 pages.

Notice of Allowance for U.S. Appl. No. 14/199,973.dated Dec. 10, 2015, 11 pages.

Notice of Allowance for U.S. Appl. No. 14/861,750, filed Sep. 22, 2015 on behalf of Lawrence Livermore National Security, LLC. dated Jul. 24, 2018. 15 pages.

Okemoto K., et al., "A Potent Adjuvant Monophosphoryl Lipid a Triggers Various Immune Responses, but Not Secretion of IL-1beta or Activation of Caspase-1," *The Journal of Immunology*,Jan. 2006, vol. 176 (2), 6 pages.

Osada Y., et al., "Polymorphonuclear Leukocyte Activation by a Synthetic Muramyl Dipeptide Analog," *Infection and Immunity*,Dec. 1982, vol. 38 (3), 7 pages.

Ouverney C.C., et al., "Combined Microautoradiography-16S rRNA Probe Technique for Determination of Radioisotope Uptake by Specific Microbial Cell Types in Situ," *Applied and Environmental Microbiology*,Apr. 1999, vol. 65 (4), 8 pages.

Parkin A., et al., "The Difference a Se Makes? Oxygen-tolerant hydrogen production by the [NiFeSe]-hydrogenase from Desulfomicrobium baculatum," Journal of the American Chemical Society,Sep. 2008, vol. 130 (40), 13410-13416. 8 pages.

Persing D.H., et al., "Taking Toll: Lipid a Mimetics as Adjuvants and Immunomodulators," *Trends in Microbiology*,Oct. 2002, vol. 10 (10 Suppl), 6 pages.

Petrakova O., et al., "Noncytopathic Replication of Venezuelan Equine Encephalitis Virus and Eastern Equine Encephalitis Virus Replicons in Mammalian Cells," *Journal of Virology*,Jun. 2005, vol. 79 (12), 12 pages.

Pettibone D.J., et al., "The Effects of Deleting the Mouse Neurotensin Receptor NTR1 on Central and Peripheral Responses to Neurotensin," *The Journal of Pharmacology and Experimental Therapeutics*,Jan. 2002, vol. 300 (1), 9 pages.

Plumere, et al., "Enzyme-catalyzed O2 removal system for electrochemical analysis under ambient air: application in an amperometric nitrate biosensor (Abstract only)", Anal Chem. Mar. 6, 2012;84(5):2141-2146, Epub Feb. 10, 2012. 2 pages.

Protocols for Preparation of Nanodiscs,Mar. 2008, 7 pages.

Radajewski S., et al., "Identification of Active Methylotroph Populations in an Acidic Forest Soil by Stable Isotope Probing," Microbiology,Aug. 2002, vol. 148 (Pt 8), 12 pages.

Radajewski S., et al., "Stable-Isotope Probing as a Tool in Microbial Ecology," *Nature*, Feb. 2000, vol. 403 (6770), 4 pages.

Ratanabanangkoon P., et al., "Two-Dimensional Streptavidin Crystals on Giant Lipid Bilayer Vesicles,"*Langmuir*,2002, vol. 18 (11), 7 pages.

Ren X.R., et al., "Different G Protein-Coupled Receptor Kinases Govern G Protein and Beta-Arrestin-Mediated Signaling of V2 Vasopressin Receptor," *Proceedings of the National Academy of Sciences of the United States of America*,Feb. 1, 2005, vol. 102(5), 6 pages.

Rensen PC, et al., "Human recombinant apolipoprotein E-enriched liposomes can mimic low-density lipoproteins as carriers for the site-specific delivery of antitumor agents." Mol Pharmacol, 52, pp. 445-455(Sep. 1997).

Rensen P.C., et al., "Recombinant Lipoproteins: Lipoprotein-like Lipid Particles for Drug Targeting,"*Advanced Drug Delivery Reviews*,Apr. 25, 2001, vol. 47(2-3), 26 pages.

Restriction Requirement for U.S. Appl. No. 14/199,973.dated Dec. 8, 2014, 7 pages.

Restriction Requirement for U.S. Appl. No. 14/861,750.dated May 19, 2017, 7 pages.

Rüger R., et al., "Generation of Immunoliposomes using Recombinant Single-Chain Fv Fragments Bound to Ni-NTA-Liposomes," *Journal of Drug Targeting*, Aug. 2005, vol. 13(7), 8 pages.

Ryan RO, "Nanobiotechnology applications of reconstituted high density lipoprotein" J Nanobiotechnology, 8:28(Dec. 2010) 10 pages.

Ryan RO, "Nanodisks: hydrophobic drug delivery vehicles" Expert Opin Drug Deliv., 5(3), pp. 343-351 (Mar. 2008).

Schena M., et al., "Quantitative Monitoring of Gene Expression Patterns With a Complementary DNA Microarray," *Scienc*,Oct. 1995, vol. 270 (5235), 4 pages.

Schnell D.J. et al., "Protein Translocons: Multifunctional Mediators of Protein Translocation across Membranes," *Cell*, Feb. 21, 2003, vol. 112(4), 15 pages.

Simon S.R., et al., "Chemical Modification of Hemoglobins: A Study of Conformation Restraint by Internal Bridging," *Proceedings of the National Academy of Sciences of the United States of America*,Aug. 1966, vol. 56 (2), 8 pages.

(56) References Cited

OTHER PUBLICATIONS

Singh-Gasson S., et al., "Maskless Fabrication of Light-directed Oligonucleotide Microarrays Using a Digital Micromirror Array," *Nature Biotechnology*,Oct. 1999, vol. 17 (10), 5 pages.
Soboh B., et al., "A Multisubunit Membrane-Bound [NiFe] Hydrogenase and an NADH-Dependent Fe-only Hydrogenase in the Fermenting Bacterium Thermoanaerobacter tengcongenis," *Microbiology*,2004, vol. 150, 13 pages.
Sun X.L., et al., "Membrane-Mimetic Films of Asymmetric Phosphtidylcholine Lipid Bolaamphiphiles," *Langmuir*,Jan. 2006, vol. 22 (3), 8 pages.
Sunahara H, et al., "Design and synthesis of a library of BODIPY-based environmental polarity sensors utilizing photoinduced electron-transfer-controlled fluorescence ON/OFF switching" J Am Chem Soc., 129, pp. 5597-5604(May 2007).
Tercier-Waeber, et al., "Submersible Online Oxygen Removal System Coupled to an in Situ Voltammetric Probe for Trace Element Monitoring in Freshwater (Abstract only)", Environ. Sci. Technol., 2000, 34 (18), pp. 4018-4024, Publication Date (Web): Aug. 11, 2000. 4 pages.
Terpe K., et al., "Overview of Tag Protein Fusions: From Molecular and Biochemical Fundamentals to Commercial Systems," *Applied Microbiology and Biotechnology*, Jan. 2003, vol. 60 (5), 11 pages.
Ueda H., et al., "Induction of Tumor Necrosis Factor-Alpha in Solid Tumor Region by the Orally Administered Synthetic Muramyl Dipeptide Analogue, Romurtide," *International Immunopharmacology*, Jan. 2001, vol. 1 (1), 8 pages. .
Uhlik O., et al., "DNA-Based Stable Isotope Probing: A Link between Community Structure and Function," *Science of the Total Environment*,Jun. 2009, vol. 407 (12), 9 pages
Ulmer J,B., et al., "Vaccine Manufacturing: Challenges and Solutions," *Nature Biotechnology*,Nov. 2006, vol. 24 (11), 7 pages.
Unger R., et al., "The Genetic Algorithm Approach to Protein Structure Prediction," *Structure and Bonding*,Feb. 2004, vol. 110, 24 pages.
VICI (Valco Instruments Co. Inc.) "Oxygen Removal System", https://www.vici.com/instr/deox.php, pp. 1-2, 2 pages,2018.
Vignais P.M., et al., "Occurrence, Classification, and Biological Function of Hydrogenases: An Overview," *Chemical Reviews*,Oct. 2007, vol. 107 (10), 67 pages.
Vuorilehto K., et al., "Indirect Electrochemical Reduction of Nicotinamide Coenzymes," *Bioelectrochemistry*, Dec. 2004, vol. 65 (1), 7 pages.
Wacey A.I., et al., "Disentangling the Perturbational Effects of Amino Acid Substitutions in the DNA-binding Domain of p53," *Human Genetics*, Jan. 1999, vol. 104 (1), 8 pages.
Weeratna R.D., et al., "CpG DNA Induces Stronger Immune Responses with Less Toxicity than Other Adjuvants," *Vaccine*, Mar. 2000, vol. 18 (17), 8 pages.
White S.H., et al., "How Translocons Select Transmembrane Helices," Annual Review of Biophysics,2008, vol. 37, 23-42. 20 pages.
Widman D.G., et al., "Construction and Characterization of a Second-Generation Pseudoinfectious West Nile Virus Vaccine Propagated Using a New Cultivation System," *Vaccine*, May 2008, vol. 26 (22), 10 pages.
Wikipedia, "5-HT Receptor," Wikipedia2007, Retrieved from the Internet:[URL: http://web.archive.org/web/20071109235348/http://en.wikipedia.org/wiki/5-HT_receptor], 4 pages.
Wikipedia, Adrenergic Receptor, https://web.archive.org/web/20061230132111http//en.wikipedia.org/wiki/Adrenergic_Receptor,2006, 4 pages.
Written Opinion for Application No. PCT/US2009/044722, dated Oct. 28, 2010., 8 pages.
Xiao K, et al., "A self-assembling nanoparticle for paclitaxel delivery in ovarian cancer." Biomaterials, 30 (30), pp. 6006-6016(2009) 24 pages.
Yang JP, et al., "Cell-free synthesis of a functional G protein-coupled receptor complexed with nanometer scale bilayer discs." BMC Biotechnol, 11:57,(May 2011) 8 pages.

Yoon J.C., et al., "Three-Dimensional Graphene Nano-Networks with High Quality and Mass Production Capability via Precursor-Assisted Chemical Vapor Deposition," *Scientific Reports*,2013, vol. 1788, 8 pages.
Zhou, H., et al., Noncovalent Attachment of NAD+ Cofactor onto Carbon Nanotubes for Preparation of Integrated Dehydrogenase-Based Electrochemical Biosensors,:2010, Langmuir Article, 26(8) 6028-6032.
Zimmermann S, et al., "Immunostimulatory DNA as Adjuvant: Efficacy of Phosphodiester CPG Oligonucleotides is Enhanced by 3' Sequence Modifications," *Vaccine*,Feb. 2003, vol. 21 (9-10), 6 pages.
Abdulreda M.H., et al., "Atomic Force Microscope Spectroscopy Reveals a Hemifusion Intermediate during Soluble N-Ethylmaleimide-Sensitive Factor-Attachment Protein Receptors-Mediated Membrane Fusion," Biophysical Journal, Jan. 2008, vol. 94 (2), 648-655. 8 pages.
Abdulreda M.H., et al., "Atomic Force Microscope Studies of the Fusion of Floating Lipid Bilayers," *Biophysical Journal*, Jun. 2007, vol. 92 (12), 4369-4376. 10 pages.
Advisory Action for U.S. Appl. No. 12/118,396, filed MAy 9, 2008. dated Jul. 7, 2015, 8 pages.
Advisory Action for U.S. Appl. No. 12/118,396. dated Jun. 7, 2012, 5 pages.
Advisory Action for U.S. Appl. No. 12/118,530. dated Jul. 23, 2015, 13 pages.
Akkaladevi, N., et al., "Assembly of anthrax toxin pore: Lethal-factor complexes into lipid nanodiscs." *Protein Science*, 2013. 22(4): p. 492-501.
Allen, T.M. et al., "Drug delivery systems: entering the mainstream." *Science*, 2004. 303(5665): p. 1818-22.
Bao P., et al., "High-Sensitivity Detection of DNA Hybridization on Microarrays Using Resonance Light Scattering," *Analytical Chemistry*, Apr. 2002, vol. 74 (8), 1792-1797.
Bayburt T.H., et al., "Assembly of Single Bacteriorhodopsin Trimmers in Bilayer Nanodiscs," Archives of Biochemistry and Biophysics, Jun. 2006, vol. 450 (2), 215-222.
Baybirt T.H., et al., "Reconstitution and Imaging of a Membrane Protein in a Nanometer-size Phospholipid Bilayer," *Journal of Structural Biology*, Sep. 1998, vol. 123 (1), 37-44. 8 pages.
Baylon, J.L., et al., "Characterizing the membrane-bound state of cytochrome P450 3A4: structure, depth of insertion, and orientation." *Journal of the American Chemical Society*, 2013. 135(23):p. 8542-8551.
Bhattacharya, P., et al., "Nanodisc-Incorporated Hemagglutinin Provides Protective Immunity against Influenza Virus Infection." *Journal of Virology*, 2010. 84(1): p. 361-371.
Blanchette C.D., et al., "Characterization and Purification of Polydisperse Reconstituted Lipoproteins and Nanolipoprotein Particles," *International Journal of Molecular Sciences*, Jul. 2009, vol. 10 (7), 2958-2971. 14 pages.
Bolikal, D. et al., "Degree of Polymerization of a Vesicle Membrane." *Macromolecules*, 1984. 17(6): p. 1287-1289.
Boschker H.T.S., et al., "The Contribution of Macrophyte-derived Organic Matter to Microbial Biomass in Salt-marsh Sediments: Stable Carbon Isotope Analysis of Microbial Biomarkers," Limnology and Oceanography, 1999, vol. 44(2), 309-319. 11 pages.
Camarero J.A., et al., "Chemoselective Attachment of Biologically Active Protein to Surfaces by Expressed Protein Ligation and its Application for Protein Chip Fabrication," *Journal of the American Chemical Society*, Nov. 2004, vol. 126 (45), 2 pages.
Cappuccio, J.A., et al., "Cell-free expression for nanolipoprotein particles: building a high-throughput membrane protein solubility platform", in Methods in Molecular Biology: High Throughput Protein Expression and Purification. 2009, vol. 498, Springer. p. 273-295.
Chen J.S., et al., "Amino Acids in SRS1 and SRS6 Are Critical for Furanocoumarin Metabolism by CYP6B1v1, a Cytochrome P450 Monooxygenase," *Insect Molecular Biology*, Apr. 2002, vol. 11 (2), 175-186. 12 pages.
Cho, K., et al., "Therapeutic nanoparticles for drug delivery in cancer." *Clinical cancer research*, 2008. 14(5): p. 1310-1316.

(56) References Cited

OTHER PUBLICATIONS

Chromy B.A., et al., "Different Apolipoproteins Impact Nanolipoprotein Particle Formation," Journal of the American Chemical Society, Nov. 2007, vol. 129 (46), 14348-14354. 7 pages.

Cleveland, T.E. IV, et al., "Small-angle X-ray and neutron scattering demonstrates that cell-free expression produces properly formed disc-shaped nanolipoprotein particles," Protein Science, Dec. 2017, vol. 27, pp. 780-789.

Coleman M., et al., "Asp 46 Can Substitute for Asp 96 as the Schiff Base Proton Donor in Bacteriorhodopsin," *Biochemistry*, Nov. 1995, vol. 34 (47), 15599-15606. 8 pages.

Crankshaw C., Nanodisc Technology: A Revolutionary System for Study of Membrane Proteins, Biofiles, retrieved on Aug. 4, 2015, Retrieved from the Internet: URL: http://www.sigmaaldrich.com/teclmical-documents/articles!biofiles/nanodisc-technology.html, vol. 8, No. 20, 3 pages.

Cuenca, AG et al., "Emerging implications of nanotechnology on cancer diagnostics and therapeutics." *Cancer*, 2006. Vol. 107, No. 3: pp. 459-466. Pages 8.

Definition of "homogeneous", Oxford Dictionaries, retrieved from https://en.oxforddictionaries.com/definition/homogeneous on Apr. 4, 2018, four pages.

Definition of Hydrogenase [online], Nov. 6, 2012 [retrieved on Nov. 6, 2012], Retrieved from Internet: URL: en.wikipedia.org/wiki/Hydrogenase, 4 pages.

Denisov I.G., et al., "Nanodiscs in Membrane Biochemistry and Biophysics", Chemical Reviews, Mar. 2017, vol. 117 (6), 4669-4713. 92 pages.

Ding, Y., et al., "A biomimetic nanovector-mediated targeted cholesterol-conjugated siRNA delivery for tumor gene therapy." *Biomaterials*, 2012. 33(34): p. 8893-8905.

Dong F., et al., " Endothelin-1 Enhances Oxidative Stress, Cell Proliferation and Reduces Apoptosis in Human Umbilical Vein Endothelial Cells: Role of ETB Receptor, NADPH oxidase and caveolin-1" British Journal of Pharmacology, Jun. 2005, vol. 145 (3), 323-333. 11 pages.

Dunn R.J., et al., "Structure-functions Studies on Bacteriorhodopsin," *The Journal of Biological Chemistry*, 1987, vol. 262 (19), 9246-9254. 9 pages.

Final Office Action for U.S. Appl. No. 12/118,396. dated Feb. 4, 2015, 29 pages.

Final Office Action for U.S. Appl. No. 12/118,396. dated Jan. 18, 2012, 17 pages.

Final Office Action for U.S. Appl. No. 12/118,396. dated Oct. 11, 2016, 29 pages.

Final Office Action for U.S. Appl. No. 12/118,396. dated Apr. 12, 2018. 25 pages.

Final Office Action for U.S. Appl. No. 16/082,924, filed Sep. 6, 2018 on behalf of Lawrence Livermore National Security, LLC. dated May 21, 2020. 50 Pages.

Forstner M., et al., "Carboxyl-Terminal Domain of Human Apolipoprotein E: Expression, Purification, and Crystallization," *Protein Expression and Purification*, Nov. 1999, vol. 17 (2), 267-272. 6 pages.

Forte T.M., et al., "Electron Microscope Study on Reassembly of Plasma High Density Apoprotein with Various Lipids," *Biochimica et Biophysica Acta*, Nov. 1971, vol. 248 (2), 381-386. 6 pages.

Gao, T., et al., (2011) "Characterizing diffusion dynamics of a membrane protein associated with nanolipoproteins using fluorescence correlation spectroscopy," Protein Science. 20:437-447.

Gao, T., et al., "Characterization of de novo synthesized GPCRs supported in nanolipoprotein discs," (2012) E.Pub, PloS One. 7(9):44911. 8 pages.

Gursky O., et al., "Compex of Human Apolipoprotein C-1 with Phospholipid: Thermodynamic or Kinetic Stability?," *Biochemistry*, Jun. 2002, vol. 41 (23), 7373-7384. 12 pages.

He, W., "Controlling the Diameter, Monodispersity and Solubility of ApoA1 Nanolipoprotein Particles using Telodendrimer Chemistry," (2013) Protein Science 22, 1078-1086.

Howland M.C. et al., "Model Studies of Membrane Disruption by Photogenerated Oxidative Assault." The Journal of Physical Chemistry B, 2010. 114(19); p. 6377-6385.

International Preliminary Report on Patentability (Chapter 1) for International Application No. PCT/US2017/020827 filed on Mar. 3, 2017 on behalf of Lawrence Livermore National Laboratory dated Sep. 11, 2018 9 pages.

International Search Report for International Application No. PCT/US2017/020827 filed on Mar. 3, 2017 on behalf of Lawrence Livermore National Laboratory dated Jun. 20, 2017 4 pages.

Jayaraman S., et al., "Structural Basis for Thermal Stability of Human Low-density Lipoprotein," *Biochemistry*, Mar. 2005, vol. 44 (10), 3965-3971. 7 pages.

Justesen, B.H., et al., "Isolation of monodisperse nanodisc-reconstituted membrane proteins using free flow electrophoresis." *Analytical chemistry*, 2013. 85(7): p. 3497-3500.

Kalmbach R., et al., "Functional Cell-free Synthesis of a Seven Helix Membrane Protein: In Situ Insertion of Bacteriorhodopsin in Liposomes," *Journal of Molecular Biology*, Aug. 2007, vol. 371 (3), 639-648. 10 pages.

Kim Y.P., et al., "Gold Nanoparticle-enhanced Secondary Ion Mass Spectrometry Imaging of Peptides on Self-assembled Monolayers," *Analytical Chemistry*, Mar. 2006, vol. 78(6), 1913-1920. 8 pages.

Klammt C., et al., "Cell-free Expression as an Emerging Technique for the Large Scale Production of Integral Membrane Protein," *The FEBS Journal*, Sep. 2006, vol. 273 (18), 4141-4153. 13 pages.

Klammt C., et al., "Evaluation of Detergents for the Soluble Expression of Alpha-helical and Beta-barrel-type Integral Membrane Proteins by a Preparative Scale Individual Cell-free Expression System," The FEBS Journal, Dec. 2005, vol. 272 (23), 6024-6038. 15 pages.

Klammt C., et al., "High Level Cell-free Expression and Specific Labeling of Integral Membrane Proteins," *European Journal of Biochemistry*, Feb. 2004, vol. 271 (3), 568-580. 13 pages.

Kreshech G.C. "Surfactants" in Water—A Comprehensive Treatise. 1975: Plenum, New York. 95-167.

Lam K, et al., "A new type of synthetic peptide library for identifying ligand-binding activity" Nature, vol. 354, pp. 82-84 (1991).

Lee J., et al., "Ab Initio Protein Structure Prediction: in From Protein Structure to Function with Bioinformatics," *Springer Science + Business Media B.V.*,2009, 23 pages.

Loll, PJ, "Membrane protein structural biology: the high throughput challenge", J. of Structural Biology, 142:144-153; 2003.

Lu B., et al., "Conformational Reorganization of the Four-helix Bundle of Human Apolipoprotein E in Binding to Phospholipid," The Journal of Biological Chemistry, Jul. 2000, vol. 275 (27), 20775-20781. 7 pages.

Ly, S., et al., (Jan. 2014) "Quantifying interactions of a membrane protein embedded in lipid nanodisc using fluorescence correlation spectroscopy," Biophysical Journal. 106: L05-L08.

Ly, S., et al., "Quantifying membrane protein interactions in solution using fluorescence correlation spectroscopy," Biophysical Journal, (Aug. 15, 2013), LLNL-JRNL-642412. Lawrence Livermore National Laboratory. 11 pages.

Madani S.Y., et al., "A concise review of carbon nanotube's toxicology." Nano Rev., 2013. vol. 4, Issue 1. 15 pages.

Miyazaki, M., et al., "Effect of phospholipid composition on discoidal HDL formation." Biochimica et Biophysica Acta (BBA)-Biomembranes, 2013. 1828(5): p. 1340-1346.

Morrow J.A., et al., "Functional Characterization of Apolipoprotein E Isoforms Overexpressed in *Escherichia coli*," *Protein Expression and Purification*, 1999, vol. 16 (2), 224-230. 7 pages.

Non-Final Office Action for U.S. Appl. No. 12/118,396. dated Aug. 30, 2011, 18 pages.

Non-Final Office Action for U.S. Appl. No. 12/118,396. dated Jan. 8, 2016, 32 pages.

Non-Final Office Action for U.S. Appl. No. 12/118,396. dated Jul. 22, 2014, 28 pages.

Non-Final Office Action for U.S. Appl. No. 12/118,396. dated Sep. 6, 2017, 33 pages.

(56) References Cited

OTHER PUBLICATIONS

Non-Final Office Action for U.S. Appl. No. 16/082,924, filed Sep. 6, 2018 on behalf of Lawrence Livermore National Security, LLC. dated Jan. 31, 2020 25 pages.
Rao R.S., et al., "Comparison of Multiplexed Techniques for Detection of Bacterial and Viral Proteins," *Journal of Proteome Research*, Jul.-Aug. 2004, vol. 3(4), 736-742. 7 pages.
Reinau M.E et al. "The Diversity of FtsY-Lipid Interactions" *Biopolymers*, vol. 3, No. 7, Jan. 2010, pp. 595-606. 12 pages.
Restriction Requirement for U.S. Appl. No. 12/118,396. dated Mar. 4, 2011, 14 pages.
Restriction Requirement for U.S. Appl. No. 16/082,924, filed Sep. 6, 2018 on behalf of Lawrence Livermore National Laboratory dated Oct. 24, 2019 9 pages.
Rusiñol A.E., et al., "In Vitro Reconstitution of Assembly of Apolipoprotein B48-Containing Lipoproteins," *The Journal of Biological Chemistry*, Mar. 21, 1997, vol. 272(12), 8019-8025. 7 pages.
Saito H. et al., "Contributions of domain structure and lipid interaction to the functionality of exchangeable human apolipoproteins" Elsevier, 2004. 43, pp. 350-380.
Segelke B.W., et al., "Laboratory Scale Structural Genomics," *Journal of Structural and Functional Genomics*, 2004, vol. 5(1-2), 147-157. 11 pages.
Shih A.Y., et al., "Disassembly of Nanodiscs with Cholate", *Nano Letters*, Jun. 2007, vol. 7 (6), 1692-1696. 5 pages.
Sonar S., et al., "A Redirected Proton Pathway in the Bacteriorhodopsin Mutant Tyr-57—Asp. Evidence for Proton Translocation Without Schiff Base Deprotonation," *The Journal of Biological Chemistry*, Nov. 1994, vol. 269 (46), 28851-18858. 8 pages.
Sonar S., et al., "Cell-Free Synthesis, Functional Refolding and Spectroscopic Characterization of Bacteriorhodopsin, an Integral Membrane Protein," *Biochemistry*, Dec. 1993, vol. 32 (50), 13777-13781. 5 pages.
Sparreboom, A., et al., "Comparative preclinical and clinical pharmacokinetics of a cremophor-free, nanoparticle albumin-bound paclitaxel (ABI-007) and paclitaxel formulated in Cremophor (Taxol)." *Clin Cancer Res*, 2005. 11(11): p. 4136-43.
Swaney J.B., "Properties of Lipid-Apolipoprotein Association Products. Complexes of Human Apo A-I and Binary Phospholipid Mixtures," *Journal of Biological Chemistry*, Sep. 1980, vol. 255, vol. 18, pp. 8798-8803.
Tieke, B. et al., "Polymerization of diacetylenes in multilayers." *Journal of Polymer Science: Polymer Chemistry Edition*, 1979. 17(6): p. 1631-1644.
Tufteland, M. et al., "Nanodisks derived from amphotericin B lipid complex." Journal of Pharmaceutical Sciences, 2008. 97(10): p. 4425-4432, 14 pages.
Vickers, K.C., et al., "MicroRNAs are transported in plasma and delivered to recipient cells by high-density lipoproteins." Nat Cell Biol, 2011. 13(4): p. 423-33. 20 pages.
Wadsater, M., et al., "Monitoring shifts in the conformation equilibrium of the membrane protein cytochrome P450 reductase (POR) in nanodiscs." *Journal of Biological Chemistry*, 2012. 287(41): p. 34596-34603.
Walter P., et al., "Preparation of Microsomal Membranes for Cotranslational Protein Translocation," *Methods in Enzymology*, 1983, vol. 96, 84-93. 10 pages.
Wang J., et al., "Comparison of the Dynamics of the Primary Events of Bacteriorhodopsin in Its Trimeric and Monomeric States," *Biophysical Journal*, Sep. 2002, vol. 83 (3), 1557-1566. 10 pages.
Wang, J., et al., "Tumor targeting effects of a novel modified paclitaxel-loaded discoidal mimic high-density lipoproteins." *Drug delivery*, 2013. 20(8): p. 356-363.
Wang, S. et al., "The unsolved mystery of apoA-1 recycling in adipocyte." Lipids in Health and Disease, 2016. 15: 35, 8 pages.
Weilhammer, D.R., et al., "The use of nanolipoprotein particles to enhance the immunostimulatory properties of innate immune agonists against lethal influenza challenge." *Biomaterials*, 2013. 34(38): p. 10305-18.
Wetterau J.R., et al., "Effect of Dipalmitoylphosphatidylcholine Vesicle Curvature on the Reaction With Human Apolipoprotein A-I," The Journal of Biological Chemistry, Sep. 1982, vol. 257 (18), 10961-10966. 7 pages.
Wientzek M., et al., "Binding of Insect Apolipophorin III to Dimyristoylphosphatidylcholine Vesicles. Evidence for a Conformational Change," *Journal of Biological Chemistry*, Feb. 1994, vol. 269 (6), 4605-4612. 8 pages.
Written Opinion for International Application No. PCT/US2018/030648 filed on May 2, 2018 on behalf of Synthetic Genomics dated Aug. 30, 2018 6 pages.
Written Opinion for International Application No. PCT/US2017/020827 filed on Mar. 3, 2017 on behalf of Lawrence Livermore National Laboratory dated Jun. 20, 2017 8 pages.
Wuu J.J., et al., "High Yield Cell-Free Production of Integral Membrane Proteins without Refolding or Detergents," *Biochimica et Biophysica Acta*, May 2008, vol. 1778 (5), 1237-1250. 14 pages.
Yavlovich, A., et al., "A novel class of photo-triggerable liposomes containing DPPC:DC8,9PC as vehicles for delivery of doxorubcin to cells." *Biochimica Biophysica Acta-Biomembranes*, 2011. 1808(1): p. 117-126. 22 pages.
Yuan, Y., et al., "Delivery of hydrophilic drug doxorubicin hydrochloride-targeted liver using apoAI as carrier." *J Drug Target*, 2013. 21(4): p. 367-374.
Advisory Action for U.S. Appl. No. 15/744,754, filed Jan. 12, 2018 on behalf of Lawrence Livermore National Security, LLC dated Mar. 16, 2021 13 pages.
Alpha Helix—Wikipedia, the free encyclopedia,Nov. 7, 2014, 15 pages. https://web.archive.org/web/20141107095336/https://en.wikipedia.org/wiki/Alpha_helix.
Amar M. et al., "A Novel Apolipoprotein C-II Mimetic Peptide That Activates Lipoprotein Lipase and Decreases Serum Triglycerides in Apolipoprotein E-Knockout Mice" *The Journal of Pharmacology and Experimental Therapeutics*, 352, pp. 227-235,Feb. 2015.
Bloedon L.T. et al., "Safety, pharmacokinetics, and pharmacodynamics of oral apoA-I mimetic peptide D-4F in high-risk cardiovascular patients" Journal of Lipid Research, vol. 49,Mar. 2008, pp. 1344-1352.
Borhani D. W. et al., "Crystal structure of truncated human apooliprotien A-I suggests a lipid-bound conformation" Proc. Natl. Acad. Sci. USA, vol. 94,Nov. 1997, pp. 12291-12296.
Cysteine—Wikipedia, the free encyclopedia,Sep. 20, 2015,8 pages. https://web.archive.org/web/20150920101331/https://en.wikipedia.org/wiki/Cysteine.
Donia M. et al., "Small Molocules from the Human Microbiota"*Science*, vol. 249, Jul. 24, 2015, pp. 1-25.
Elson E. L. "Fluorescence Correlation Spectroscopy: Past, Present, Future" Biophysical Journal, vol. 101, Dec. 2011, pp. 2855-2870.
Final Office Action for U.S. Appl. No. 15/744,754, filed Jan. 12, 2018, on behalf of Lawrence Livermore National Laboratory.dated Oct. 14, 2020. 21 Pages.
Final office Action for U.S. Appl. No. 15/755,018, filed Feb. 23, 2018 on behalf of Lawrence Livermore National Laboratory.dated Aug. 7, 2020. 14 pages.
Gilmore S. F. et al., "Lipid composition dictates serum stability of reconstituted high-density lipoproteins: implications for in vivo applications" Royal Society of Chemistry, Nanoscale, Mar. 2018, 10, 7420-7430. 12 pages.
Gilmore S. F. et al., "Lipid cross-linking of nanolipoprotein particles substantially enhances serum stability and cellular uptake" Applied Materials and Interfaces, Jul. 2016, 8, 20549-20557. 9 pages.
Hafner, et al., "Development status and future prospects for a vaccine against Chlamydia trachomatis infection," Vaccine, 32, (2014), pp. 1563-1571.Published online: Aug. 22, 2013. 9 Pages.
He Y. et al., "Apolipoprotein A1 Forms 5/5 and 5/4 Antiparallel Dimers in Human High-density Lipoprotein"*Molecular & Cellular Proteomics*, 18, pp. 854-864, Jul. 2019.
Kuai R. et al., "Designer vaccine nanodiscs for personalized cancer immunotherapy" *Nature Materials*, Dec. 201610 pages. DOI:10.1038/NMAT4822.
Kuai R et al., "Designer vaccine nanodiscs for personalized cancer immunotherapy (Supplementary Information)" *Nature Materials*, December 201618 pages. DOI:10.1038/NMAT4822.

(56) References Cited

OTHER PUBLICATIONS

Leman L.J. et al., "Molecules that Mimic Apolipoprotein A-I: Potential Agents for Treating Atherosclerosis" J Med Chem, 57(6), Mar. 2014, 2169-2196. 56 pages.
Li J. et al., "Synthesis of many different types of organic small molecules using one automated process" Science Mag, vol. 347 is. 6227, Mar. 13, 2015, pp. 1221-1226.
Li L. et al., "Double Belt Structure of Discoidal High Density Lipoproteins: Molecular Basis for Size Heterogeneity" J. Mol. Biol, vol. 343,2004, pp. 1293-1311.
Liposome—Wikipedia, the free encyclopedia.Dated: Jul. 5, 2016,7 pages, https://en.wikipedia.org/wiki/Liposome.
Marsh D. "Equation of State for Phospholipid Self-Assembly" Biophysical Journal, vol. 110, Jan. 2016, pp. 188-196.
Mendez A.J. "Synthetic Amphipathic Helical Peptides That Mimic Apolipoprotein A-I in Clearing Cellular Cholesterol"J Clin. Invest, vol. 94, Oct. 1994, pp. 1698-1705.
Micelle—Wikipedia, the free encyclopedia,Dated: Dec. 1, 2020, 7 pages https://en.wikipedia.org/wiki/Micelle.
Nanodisc—Wikipedia, the free encyclopedia.Dated: Jul. 5, 2016, 3 pages, https://en.wikipedia.org/wiki/Nanodisc.
Nanodisc Inc. Company Profile—ZoomInfo.com, Dated: May 25, 2015, 2 pages, https://www.zoominfo.com/c/nanodisc/65701329.
Non-Final Office Action for U.S. Appl. No. 15/755,018, filed Feb. 23, 2018, on behalf of Lawrence Livermore National Laboratory. dated Jul. 16, 2021. 22 Pages.
Non-Final Office Action for U.S. Appl. No. 16/082,924, filed Sep. 6, 2018 on behalf of Lawrence Livermore National Security, LLCdated May 25, 202125 pages.
Non-Final Office Action for U.S. Appl. No. 16/159, 189, filed Oct. 12, 2018 on behalf of Lawrence Livermore National Security, LLC. dated Jun. 24, 2021. 32 Pages.
Non-Final Office Action for U.S. Appl. No. 16/609,420, filed Oct. 29, 2019 on behalf of Lawrence Livermore National Laboratory. dated Dec. 28, 2020. 53 Pages.
Notice of Allowance for U.S. Appl. No. 15/499,855, filed Apr. 27, 2017 on behalf of Lawrence Livermore National Laboratory. dated Oct. 15, 2020. 9 pages.
Notice of Allowance for U.S. Appl. No. 15/499,855, filed Apr. 27, 2017 on behalf of Lawrence Livermore National Security LLCdated Jan. 25, 20219 pages.
Notice of Allowance for U.S. Appl. No. 15/499,855, filed Apr. 27, 2017 on behalf of Lawrence Livermore National Security, LLC ..dated May 14, 2021.10 Pages.
Notice of Allowance for U.S. Appl. No. 15/499,855, filed Apr. 27, 2017 on behalf of Lawrence Livermore National Security, LLC. dated Jun. 25, 2020. 9 pages.
Notice of Allowance for U.S. Appl. No. 15/744,754, filed Jan. 12, 2018, on behalf of Lawrence Livermore National Laboratory. dated Jul. 14, 2021. 11 pages.
Notice of Allowance for U.S. Appl. No. 16/609,420, filed Oct. 29, 2019 on behalf of Lawrence Livermore National Laboratory. dated Jul. 28, 2021. 7 Pages.
Notice of Allowance for U.S. Appl. No. 16/609,420, filed Oct. 29, 2019 on behalf of Lawrence Livermore National Laboratory. dated May 6, 2021. 10 Pages.
Plotkin, et al., Vaccines, WB Saunders Company, p. 571. Year:1988. 2 Pages.
Popot J.L. "Alternatives to Detergents for Handling Membrane Proteins in Aqueous Solutions" Membrane Proteins in Aqueous Solutions, Jun. 2018, pp. 97-149. 134 p.
Popovic K. et al., "Structure of saposin A lipoprotein discs" PNAS, vol. 109 No. 8, Feb. 2012, pp. 2908-2912.
Restriction Requirement for U.S. Application No. 16/159,189, filed Oct. 12, 2018 on behalf of Lawrence Livermore National Security, LLC. dated Jan. 29, 2021. 6 Pages.
Segrest J. P. "Amphipathic Helix Motif: Classes and Properties" Proteins: Structure, Function, and Genetics, vol. 8,1990, pp. 103-117.
Segrest J.P. et al., "Pathogenesis of atherosclerosis" Current Opinion in Cardiology, vol. 9,1994, pp. 404-410.
Small molecule—Wikipedia, the free encyclopedia, May 12, 2015, 4 pages. https://web.archive.org/web/20150512235530/https://en.wikipedia.org/wiki/Small_molecule.
Small Molecules in Metabolomics: An Introduction. Retrieved fromthe web on Aug. 4, 2020.https://www.ebi.ac.uk/training-beta/online/courses/metabolomics-introduction/what-is/small-molecules/ 2 Pages.
Spuhler P. et al., "Binding of Apolipoprotein A-I Model Peptides to Lipid Bilayers" The Journal of Biological Chemistry, vol. 269 No. 39,Sep. 1994, pp. 23904-23910.
Swainsbury D.J.K et al., "The effectiveness of styrene-maleic acid (SMA) copolymers for solubilisation of integral membrane proteins from SMA-accessible and SMA-resistant membranes" BBA-Biomembranes, 1859, Jul. 2017, pp. 2133-2143.
Troutt J.S. et al., "An apolipoprotein A-I mimetic dose-dependently increases the formation of preB1 HDL in human plasma" Journal of Lipid Research, vol. 49, Mar. 2008, pp. 581-587.
Watson C.E. et al., "Treatment of patients with cardiovascular disease with L-4F, an apo-A1 mimetic, did not improve select biomarkers of HDL function" Journal of Lipid Research, vol. 52, Feb. 2011, pp. 361-373.
Wool G.D. "Apolipoprotein A-I mimetic peptide helix number and helix linker influence potentially anti-atherogenic properties" Journal of Lipid Research, vol. 49,2008, pp. 1268-1283.
Zhao Y. et al., "Self-Assembling Cyclic D,L-a-Peptides as Modulators of Plasma HDL Function. A Supramolecular Approach toward Antiatherosclerotic Agents" ACS Central Science, vol. 3, Jun. 2017, pp. 639-646.
Advisory Action for U.S. Appl. No. 15/499,855, filed Apr. 27, 2017 on behalf of Lawrence Livermore National Security, LLC. dated Dec. 31, 2019. 3 pages.
Anantharamaiah, G.M., et al., "Studies of Synthetic Peptide Analogs of the Amphipathic Helix / Structures of Complexes with Dimyristoyl Phosphatidycholine ," 1985, The Journal of Biological Chemistry, vol. 260, No. 18, 10248-10255.
Baas B.J., et al., "HOmotropic Cooperativity of Monomeric Cytochrome P450 3A4 in a Nanoscale Native Bilayer Environment," Archives of Biochemistry and Biophysics, Oct. 2004, vol. 439 (2), 218-223, 11 pages.
Baughman, R.H. "Solid-state polymerization of diacetylenes." Journal of applied Physics43(11), 4362-4370,(Nov. 1972). 10 pages.
Bayburth T.H., et al., "Self-Assembly of Single Integral Membrane Proteins into Soluble Nanoscale Phospholipid Bilayers," Protien Science, Nov. 2003, vol. 12, (11), 2476-2481. 6 pages, XP002498218, ISSN: 0961-8368.
Bayburth T.H., et al., "Single-Molecule Height Measruements on Microsomal Cytochrome P450 in Nanometer-Scale Phospholipid Bilayer Disks," Proceedings of the National Academy of Sciences of the United States of America, May 2002, vol. 99, (10), 6725-6730. 6 pages.
Bayburt T.H., et al., "Membrane Protein Assembly into Nanodiscs," FEBS Letters, May 2010, vol. 584 (9), 1721-1727. 7 pages.
Bayburt T.H., et al., "Transducin Activation by Nanoscale Lipid Bilayers Containing Ine and Two Rhodopsins," The Journal of Biological Chemistry, May 2007, vol. 282 (20), 14875-14881. 8 pages.
Chung, B.H., et al., "Studies of Synthetic Peptide Analogs of the Amphipathic Helix / Correlation of Structure with Function," 1985, The Journal of Biological Chemistry, vol. 260, No. 18, 10256-10262.
Civjan N., et al., "Direct Solubilization of Heterologously Expressed Membrane Proteins by Incorporation Into Nanoscale Lipid Bilayer," Biotechniques, Sep. 2003, vol. 35 (3), 6 pages.
Cruz F., et al., "Kinetic Properties of Recombinant MAO-A on Incorporation into Phospholipid Nanodisks," Journal of Neural Transmission, 2007, vol. 114 (6), 699-702. 4 pages.
Das A. et al., "Screening of Type I and II Drug Binding to Human Cytochrome P450-3A4 in Nanodiscs by Localized Surface Plasmon Resonance Spectroscopy." Analytical Chemistry, 2009. 81(10): p. 3754-3759.

(56) References Cited

OTHER PUBLICATIONS

Dawson P.E., et al., "Synthesis of Native Proteins by Chemical Ligation," *Annual Review of Biochemistry*,2000, vol. 69, 923-960. 39 pages.
De Filippis et al., "Enhanced Protein Thermostability by Ala → Aib Replacement," *Biochemistry*1998, 37, 1686-1696. 11 Pages.
Dengue Fever Climbs the Social Ladder, Special Report, *Nature*, Aug. 2007, vol. 448, 734-735. 2 pages.
Final Office Action for U.S. Appl. No. 12/469,533. dated Dec. 4, 2012, 7 pages.
Final Office Action for U.S. Appl. No. 12/469,533. dated Oct. 24, 2011, 11 pages.
Final Office Action for U.S. Appl. No. 12/604,362. dated Dec. 4, 2012, 8 pages.
Fischer, N.O., et al. "Colocalized Delivery of Adjuvant and Antigen Using Nanolipoprotein Particles Enhances the Immune Response to Recombinant Antigens." *Journal of the American Chemical Society*135(6), 2044-2047, (Jan. 2013). 4 pages.
Fischer N.O. et al., "Isolation, characterization, and stability of discretely-sized nanolipoprotein particles assembled with Apolipophorin-III" PLoS One, 2010, vol. 5, No. 7, e11643.
Frias, J.C., et al. "Properties of a Versatile Nanoparticle Platform Contrast Agent to Image and Characterize Atherosclerotic Plaques by Magnetic Resonance Imaging." *Nano Letters*6(10), 2220-2224, (Jul. 2006). 5 pages.
Frydman J., et al., "Principles of Chaperone-assisted Protein Folding: Differences Between in Vitro and in Vivo Mechanisms," Science, Jun. 1996, vol. 272 (5267), 1497-1502. 6 pages.
Georger, J.H., et al. "Helical and Tubular Microstructures Formed by Polymerizable Phosphatidylcholines."*Journal of American Chemical Society*109(20), 6169-6175, (Sep. 1987). 7 pages.
Hauger R.L., et al., "Corticotropin Releasing Factor (CRF) Receptor Signaling in the Central Nervous System: New Molecular Targets," *CNS & Neurological Disorders Drug Targets*, Aug. 2006, vol. 5 (4), 49 pages.
Hayward, J.A., et al. "Biomembrane surfaces as models for polymer design: the potential for haemocompatibility." *Biomaterials*5(3), 135-142, (May 1984). 8 pages.
Imura, T., et al., "Minimum Amino Acid Residues of an a-Helical Peptide Leading to Lipid Nanodisc Formation," 2014, J. Oleo Sci. 63, (11) 1203-1208.
Imura, T., et al., "Surfactant-like Properties of an Amphilic a-Helical Peptide Leading to Lipid Nanodisc Formation," 2014, Langmuir, 30, 4752-4759.
"Individual" from Merriam-Webster, Jan. 13, 2015, accessed via WayBackMachine.com (2 pages).
International Preliminary Report on Patentability (Chapter 1) for International Application No. PCT/US2016/048632 filed on Aug. 25, 2016 on behalf of Lawrence Livermore National Laboratory dated Feb. 27, 2018 11 pages.
International Preliminary Report on Patentability for Application No. PCT/US2015/051172 filed Sep. 9, 2016 on behalf of Lawrence Livermore National Security, LLC. dated Mar. 13, 2018. 8 pages. (English Only).
International Search Report for Application No. PCT/US2016/051172, filed on Sep. 9, 2016 on behalf of Lawrence Livermore National Laboratory. dated Dec. 13, 2016. 6 pages.
International Search Report for International Application No. PCT/US2016/048632 filed on Aug. 25, 2016 on behalf of Lawrence Livermore National Laboratory dated Feb. 6, 2017 5 pages.
Ishihara G., et al., "Expression of G Protein Coupled Receptors in a Cell-free Translational System Using Detergents and Thioredoxin-fusion Vectors," *Protein Expression and Purification*, May 2005, vol. 41 (1), 11 pages.
Jia, J., et al. "Preparation, Characterizations, and In Vitro Metabolic Processes of Paclitaxel-Loaded Discoidal Recombinant High-Density Lipoproteins." *Journal of Pharmaceutical Sciences*101(8), 2900-2908, (Aug. 2012). 9 pages.
Johnston, D.S., et al. "Phospholipid Polymers—Synthesis and Spectral Characteristics." *Biochimica et Biophysica Acta*602(1), 57-69, (Oct. 1980). 13 pages.
Jonas A., "Defined Apolipoprotein A-I Conformations in Reconstituted High Density Lipoprotein Discs," The Journal of Biological Chemistry, Mar. 1989, vol. 264 (9), 4818-4824. 7 pages.
Jonas A., "Reconstitution of High-density Lipoproteins," Methods in Enzymology, 1986, vol. 128, 553-582.
Jones M.K., et al., "Computer Programs to Identify and Classify Amphipathic alpha Helical Domains," Journal of Lipid Research, Feb. 1992, vol. 33 (2), 287-296. 10 pages.
Jonsson, M.P., et al. "Supported Lipid Bilayer Formation and Lipid-Membrane-Mediated Biorecognition Reactions Studied with a New Nanoplasmonic Sensor Template." *Nano Letters*7(11), 3462-3468, (Sep. 2007). 7 pages.
Kim, J-M., et al. "Immobilized Polydiacetylene Vesicles on Solid Substrates for Use as Chemosensors." *Advanced Materials*15(13), 1118-1121, (Jul. 2003). 4 pages.
Klammt C., et al., "Cell-free Production of G Protein-coupled Receptors for Functional and Structural Studies," Journal of Structural Biology, Jul. 2007, vol. 158, 482-493. 13 pages.
Lam K.S., et al., "Application of Combinatorial Library Methods in Cancer Research and Drug Discovery," Anti-cancer Drug Design, Apr. 1997, vol. 12 (3), 145-167. 24 pages.
Lamparski, H., et al. "Two-Dimensional Polymerization of Lipid Bilayers Degree of Polymerization of Sorbyl Lipids." *Macromolecules*28(6), 1786-1794, (Mar. 1995). 9 pages.
Lei, J., et al. "Two-Dimensional Polymerization of Lipid Bilayers: Rate of Polymerization of Acryloyl and Methacryloyl Lipids." *Macromolecules*27(6), 1381-1388, (Mar. 1994). 8 pages.
Lieser, G., et al. "Structure, Phase Transitions and Polymerizability of Multilayers of Some Diacetylene Monocarboxylic Acids." Thin Solid Films 68(1), 77-90, (May 1980). 14 pages.
Mao H.B. et al., "Design and characterization of immobilized enzymes in microfluidic systems." Analytical Chemistry, 2002. 74(2): p. 379-385.
"Microsome" from Wikipedia, Mar. 3, 2008, accessed via WayBackMachine.com (1 page).
Midtgaard, S.R., et al., "Self-assembling peptides form nanodiscs that stabilize membrane proteins," 2014, Soft Matter, 10, 738-752.
Morigaki, K., et al. "Surface Functionalization of a Polymeric Lipid Bilayer for Coupling a Model Biological Membrane with Molecules, Cells, and Microstructures." *Langmuir*29(8), 2722-2730, (Jan. 2013). 9 pages.
Nanodisc Trademark #78166119, Owner: Sligar, Stephen G., Retrieved from the Internet: [URL:https://inventively.com/search/trademarks/78166119], retrieved on Aug. 4, 2015, 2 pages.
Non-Final Office Action for U.S. Appl. No. 15/755,018, filed Feb. 23, 2018 on behalf of Lawrence Livermore National Laboratory. dated Apr. 22, 2020. 57 Pages.
Non-Final Office Action for U.S. Appl. No. 12/469,533. dated May 23, 2012, 15 pages.
Non-Final Office Action for U.S. Appl. No. 12/604,362. dated May 7, 2012, 12 pages.
Non-Final Office Action for U.S. Appl. No. 15/744,754, filed Jan. 12, 2018 on behalf of Lawrence Livermore National Laboratory. dated Mar. 4, 2020. 53 pages.
Notice of Allowance for U.S. Appl. No. 12/469,533. dated Jul. 3, 2014, 13 pages.
Notice of Allowance for U.S. Appl. No. 12/604,362. dated Jul. 30, 2014, 13 pages.
Ohno, H., et al. "Polymerization of Liposomes Composed of Diene-Containing Lipids by UV and Radical Initiators: Evidence for the Different Chemical Environment of Diene Groups on 1- and 2-Acyl Chains." *Macromolecules*20(5), 929-933, (May 1987). 5 pages.
Okahata Y et al., "Polymerizable lipid-corked capsule membranes. Polymerization at different positions of corking lipid bilayers on the capsule and effect of polymerization on permeation behavior." *Journal of the American Chemical Society*,1988, vol. 110, No. 8, pp. 2495-2500.

(56) References Cited

OTHER PUBLICATIONS

Okazaki, T., et al. "Phase Separation of Lipid Microdomains Controlled by Polymerized Lipid Bilayer Matrices." *Langmuir* 26(6), 4126-4129, (Dec. 2009). 4 pages.
Okazaki T. et al., "Polymerized lipid bilayers on a solid substrate: Morphologies and obstruction of lateral diffusion." Langmuir, 2009. 25(1): p. 345-351.
Patel J.D., et al., "Preparation and Characterization of Nickel Nanoparticles for Binding to His-Tag Proteins and Antigens," *Pharmaceutical Research*,Feb. 2007, vol. 24 (2), 343-352. 10 pages.
Pavlidou M. et al., "Nanodiscs Allow Phage Display Selection for Ligands to Non-Linear Epitopes on Membrane Proteins." PLoS One, 2013. 8(9).
PDB database search for oxysterol binding protein, retrieved from the Internet: <http://www.rcsb.org/pdb/results/results.do?tabtoshow=Current&qrid=37B93383>, retrieved on Feb. 20, 2020. 7 Pages.
Peters-Libeau C.A., et al., "Model of Biologically Active Apolipoprotein E Bound to Dipalmitoylphosphatidylcholine," The Journal of Biological Chemistry, Jan. 2006, vol. 281 (2), 1073-1079.8 pages.
Portet T. et al., "A new method for measuring edge tensions and stability of lipid bilayers: effect of membrane composition." Biophysical Journal, 2010. 99(10): p. 3264-3273.
Rabinovich, A.L., et al. "On the conformational, physical properties and functions of polyunsaturated acyl chains." *Biochimica et Biophysica Acta* 1085(1), 53-62, (Aug. 1991). 10 pages.
Rawicz W. et al., "Effect of Chain Length and Unsaturation on Elasticity of Lipid Bilayers." Biophysical Journal. 2000, 79(1): p. 328-339.
Regen, S.L., et al. "Polymerized Phophatidyl Choline Vesicles. Stabilized and Controllable Time-Release Carriers." *Biochemical and Biophysical Research Communications* 101(1), 131-136, (Jul. 1981). 6 pages.
Restriction Requirement for U.S. Appl. No. 15/755,018, filed Feb. 23, 2018 on behalf of Lawrence Livermore National Laboratory. dated Oct. 2, 2019. 10 Pages.
Restriction Requirement for U.S. Appl. No. 12/469,533. dated Jun. 7, 2011, 8 pages.
Restriction Requirement for U.S. Appl. No. 12/604,362. dated Jan. 11, 2012, 8 pages.
Restriction Requirement for U.S. Appl. No. 15/744,754, filed Jan. 12, 2018 on behalf of Lawrence Livermore National Laboratory dated Aug. 7, 2019 9 pages.
Ruger R., et al., "In Vitro Characterization of Binding and Stability of Single-Chain Fv Ni-NTA-Liposomes," *Journal of Drug Targeting*,Sep. 2006, vol. 14(8), 576-582. 7 pages.
Ruchala et al., "Oxpholipin 11D: An Anti-Inflammatory Peptide That Binds Cholesterol and Oxidized Phospholipids," PloS One, Apr. 2010, vol. 5, Issue 4, e10181. 13 pages.
Sadownik, A., et al. "Polymerized Liposomes Formed under Extremely Mild Conditions." *Journal of American Chemical Society* 108(24), 7789-7791, (Nov. 1986). 3 pages.
Sawasaki T., et al., "A Bilayer Cell-Free Protein Synthesis System for High-Throughput Screening of Gene Products," *FEBS Letters*, Mar. 6, 2002, vol. 514(1), 102-105. 4 pages.
Schmitt L., et al., "Synthesis and Characterization of Chelator-Lipids for Reversible Immobilization of Engineered Proteins at Self-Assembled Lipid Interfaces, "*Journal of the American Chemical Society*, 1994, vol. 116 (19), 8485-8491. 7 pages.
Segota S., et al., "Spontaneous Formation of Vesicles," *Advances in Colloid and Interface Science*,Sep. 2006, vol. 121, pp. 51-75, 25 pages.
Sells, T.D., et al. "Two-Dimensional Polymerization of Lipid Bilayers: Degree of Polymerization of Acryloyl Lipids." *Macromolecules* 27(1), 226-233, (Jan. 1994). 8 pages.
Serrano, J., et al. "Polymerized Surfactant Vesicles. Determinations of Rates and Degrees of Polymerization in Vesicles Prepared from Styrene-Containing Surfactants." *Macromolecules* 18(10), 1999-2005, (Oct. 1985). 7 pages.

Shaw A.W., et al., "Phospholipid Phase Transitions in Homogeneous Nanometer Scale Bilayer Discs," *FEBS letters*, Jan. 2004, vol. 556 (1-3), 260-264. 5 pages.
Sligar, S., "Overview of Nanodisc Technology" from Sligar Lab, accessed Nov. 21, 2014 (1 page).
Sligar webpage http://sligarlab.life.uiuc.edu/nanodisc.html, accessed Feb. 28, 2018. "Nanodisc Technology: Soluble Lipid Bilayer Systems for Structural and Functional Studies of Membrane Proteins" (3 pages).
Sparks D.L. et al., "Effect of cholesterol on the charge and structure of apolipoprotein A-I in recombinant high density lipoprotein particles." Journal of Biological Chemistry, 1993. 268(31): p. 23250-7.
Sperling R.A., et al., "Surface Modification, Functionalization and Bioconjugation of Colloidal Inorganic Nanoparticles," Philosophical Transactions of the Royal Society A, Mar. 2010, vol. 368, 1333-1383, 51 pages.
STRYER., "Lipid Vesicles (Liposomes) and Planar Bilayer Membranes are Valuable Model Systems," Biochemistry, 1995, 1 page.
Svetina S., et al., "Shape Behavior of Lipid Vesicles as the Basis of Some Cellular Processes," The Anatomical Record, Nov. 2002, vol. 268 (3), 215-225. 11 pages.
Tark S.H. et al., "Nanomechanical detection of cholera toxin using microcantilevers functionalized with ganglioside nanodiscs." Nanotechnology, 2010. 21(43).
Toniolo C. et al., "Lipopeptaibols, a novel family of membrane active, antimicrobial peptides" *Cellular and Molecular Life Sciences*, vol. 58,2001, pp. 1179-1188, 10 pages.
Tsuchida, E., et al. "Polymerization of Unsaturated Phospholipids as Large Unilamellar Liposomes at Low Temperature." *Macromolecules* 25(1) 207-212, (Jan. 1992). 6 pages.
Tufteland M., et al., "Peptide Stabilized Amphotericin B Nanodisks," *Peptides*,Apr. 2007, vol. 28 (4), 741-746. 6 pages.
"Vesicle" from Wikipedia, Dec. 16, 2008, accessed via WayBackMachine.com (5 pages).
Wallin E., et al., "Genome-Wide Analysis of Integral Membrane Proteins from Eubacterial, Archaean, and Eukaryotic Organisms," *Protein Science*,Apr. 1998, vol. 7 (4), 1029-1038. 10 pages.
Whorton M.R., et al., "A Monomeric G Protein-Coupled Receptor Isolated in a High-Density Lipoprotein Particle Efficiently Activates its G Protein," Proceedings of the National Academy of Sciences, May 2007, vol. 104 (18), 7682-7687. 6 pages.
Written Opinion for Application No. PCT/US2015/051172, filed on Sep. 9, 2016 on behalf of Lawrence Livermore National Laboratory, dated Dec. 13, 2016, 7 pages.
Written Opinion for International Application No. PCT/US2016/048632 filed on Aug. 25, 2016 on behalf of Lawrence Livermore National Laboratory dated Feb. 6, 2017 10 pages.
Yang T. et al., "Identification and cellular localization of human PFTAIRE1" Gene, 2001. 267(2): p. 165-172.
Yang T.L. et al., "Investigations of bivalent antibody binding on fluid-support phospholipid membranes: The effect of hapten density." Journal of the American Chemical Society, 2003. 125(16): p. 4779-4784.
International Search Report dated Aug. 30, 2018, regarding PCT/US2018/030648.
Zidovska, A. et al.: "*Block Liposome and Nanotube Formation is a General Phenomenon of Two-Component Membranes Containing Multivalent Lipids*"; Soft Matter; Jan. 1, 2011, vol. 7, No. 18, pp. 8363-8369.
Adamczyk J., et al., "The Isotope Array, a New Tool That Employs Substrate-Mediated Labeling of rRNA for Determination of Microbial Community Structure and Function," *Applied and enviromental microbiology*, Nov. 2003, vol. 69 (11), 13 pages.
Addison S.L., et al., "Stable Isotope Probing: Technical Considerations When Resolving (15)N-labeled RNA in Gradients," *Journal of Micorbiological Methods*, Jan. 2010, vol. 80(1), 6 pages.
Badamchi-Zadeh A, et al., "A multi-component prime-boost vaccination regimen with a consensus MOMP antigen enhances chlamydia trachomatis clearance." Frontiers in Immunology, vol. 7, Article 162, pp. 1-11 (Apr. 2016).

(56) References Cited

OTHER PUBLICATIONS

Baehr W, et al., "Mapping antigenic domains expressed by Chlamydia trachomatis major outer membrane proteinm gens." Proceeding of the National Academy of Sciences, vol. 85, pp. 4000-4004 (1998).

Blanchette C.D., et al., "Atomic Force Microscopy Differntiates Discrete Size Distributions Between Membrane Proteing Containing and Empty Nanolipoprotein Particles," Biochimica et Biophysica Acta, 2009, vol. 1788 (3), 724-731. 8 pages.

Carmichael J.R. et al., "Induction of protection against vaginal shedding and infertility by recombinant Chlamydia vaccine" Vaccine, 29,pp. 5276-5283(2011).

Chen et al., "Fluorescence Study of Inclusion Complexes between Star-Shaped Cholic Acid Derivatives and Polycyclic Aromatic Fluorescent Probes and the Size Effecs of Host and Guest Molecules" Journal of Physical Chemistry B. vol. 112, No. 11, p. 3402-3409 (2008).

Choquet C.G., et al., "Stability of Pressure-extruded Liposomes Made From Archaeobacterial Ether Lipids," *Applied Microbiology and Biotechnology*, Nov. 1994, vol. 42 (2-3), 10 pages.

Coleman M.A, et al., "Expression and Association of the Yersinia oestis Translocon Proteins, YopB and YopD, Are Facilitated by Nanolipoprotein Particles." *PLoS One*p.e0150166 (2016). 16 pages.

Conlan J, et al., "Isolation of recombinant fragments of the major outer-membrane protein of Chlamydia trachomatis: their potential as subunit vaccines" Journal of General Microbiology, 136, pp. 2013-2020 (1990).

Corrected Notice of Allowance for U.S. Appl. No. 13/719,785, filed Dec. 19, 2012 on behalf of Lawrence Livermore National Laboratory dated May 23, 2016 5 pages.

Dalkara et al., "Intracytoplasmic Delivery of Anionic Proteins" Molecular Therapy, Jun. 2004, vol. 9, No. 6, pp. 964-969.

Davidson E, et al., "A high-throughput shotgun mutagenesis approach to mapping B-cell antibody epitopes" Immunology, 143, pp. 13-20 (2014).

Duncan R., "Dawning Era of Polymer Therapeutics" Nature Review Drug Discovery vol. 2, No. 5 p. 347-360 (2003).

Farris C.M. et al., "CD4+ T cells and antibody are required for optimal major outer membrane protein vaccine-induced immunity to Chlamydia muridarum genital infection" Infection and Immunity, vol. 78, No. 10, pp. 4374-4383 (2010).

Feher V.A. et al., "A 3-dimensional trimeric B-barrel model for Chlamydia MOMP contains conserved and novel elements of Gram-negative bacterial porins." PloS one p.e68934, vol. 8, Issue 7 (2013). 11 pages.

Ferrara L.G.M. et al., "MOMP from Campylobacter jejuni Is a Trimer of 18-Stranded beta-Barrel Monomers with a Ca(2+) Ion Bound at the Constriction Zone." J Mol Biol (2016), 428(22), pp. 4528-4543. 16 pages.

Final Office Action for U.S. Appl. No. 15/499,855, filed Apr. 27, 2017 on behalf of Lawrence Livermore National Laboratory dated Aug. 8, 2019 11 pages.

Findlay H.E, et al., "Surface expression, single-channel analysis and membrane topology of recombinant Chlamydia trachomatis Major Outer Membrane Protein" BMC Microbiol, 5:5 (2005). 15 pages.

Ghosh M, et al., "Cationic lipid Nanodisks as an siRNA delivery vehicle" Biochem Cell Biol (2014), 92(3): 200-205. 14 pages.

Gref et al., "Biodegradable Long-Circulating Polymeric Nanospheres" Science American Association for the Advancement of Science vol. 263 No. 5153, p. 1600-1603 (1994).

Haque F, et al., "Incorporation of a viral DNA-packaging motor channel in lipid bilayers for real-time, single-molecule sensing of chemicals and double-stranded DNA." Nat Protoc, vol. 8, No. 2, pp. 373-392 (2013).

He W, et al., "Cell-free expression of functional receptor tyrosine kinases" Sci Rep, 5:12896 (2015), 8 pages.

He W, et al., "Producing Membrane Bound Proteins as Countermeasures to infectious Diseases" Synthetic Genomics Vaccines (2016), 1 page.

Hein C.D., et al., "Click Chemistry, A Powerful Tool for Pharmaceutical Sciences," Pharmaceutical Research, Oct. 2008, vol. 25 (10), 30 pages.

Inic-Kanada A, et al., "A Probiotic Adjuvant Lactobacillus rhamnosus Enhances Specific Immune Responses after Ocular Mucosal Immunization with Chlamydial Polymorphic Membrane Protein C." PloS One p. e015785 (2016) 14 pages.

International Preliminary Report on Patentability for International Application No. PCT/US2018/030537 filed on May 1, 2018 on behalf of Lawrence Livermore National Security. dated Nov. 14, 2019. 11 pages.

International Search Report and Written Opinion for PCT/US2009/057852, 19 pages, dated May 6, 2010.

International Search Report and Written Opinion for PCT/US2012/070508, 9 pages, dated Feb. 27, 2013.

International Search Report for International Application No. PCT/US2018/030537 filed on May 1, 2018 on behalf of Lawrence Livermore National Security dated Jan. 17, 2019 5 pages.

Johnson R.M et al., "PmpG 303-311, a protective vaccine epitope that elicits persistent cellular immune responses in Chlamydia muridarum-immune mice." Infect Immun, vol. 80, No. 6, p. 2204-2211 (2012).

Karunakaran K.P. et al., "Immunoproteomic discovery of novel T cell antigens from the obligate intracellular pathogen Chlamydia" J Immunol p. 2459-65 (2008).

Karunakaran K.P. et al., "Outer membrane proteins preferentially load MHC class II peptides: implications for a Chlamydia trachomatis T cell vaccine." Vaccine, 33, p. 2159-2166 (2015).

Klussman S, et al., "The Aptamer Handbook: Functional Oligonucleotides and Their Applications" Wiley-VCH (2006) 509 pages.

Koren E, et al., "Clinical validation of the "in silico" prediction of immunogenicity of a human recombinant therapeutic protein" Clinical Immunology, 124, pp. 26-32 (2007).

Levy-Nissenbaum E et al., "Nanotechnology and aptamers: applications in drug delivery" Trends in Biotechnology26(8):442-449 (2008).

Li et al., "Antimicrobial Activities of Amine-and Guanidine-Functionalized Cholic Acid Derivatives" Antimicrobial Agents and Chemotherapy vol. 43 (6) p. 1347-1349 (Jun. 1999).

Luo et al., "Asymmetric Poly(ethylene glycol) Star Polymers with a Cholic Acid Core and Their Aggregation Properties" Biomacromolecules vol. 10 No. 4 p. 900-906 (2009).

Manning D.S. et al., "Expression of the major outer membrane protein of Chlamydia trachomatis in *Escherichia coli*." Infection and Immunity, vol. 61, No. 10, pp. 4093-4098 (1993).

Non-Final Office Action for U.S. Appl. No. 12/352,548. dated Sep. 13, 2011, 19 pages.

Non-Final Office Action for U.S. Appl. No. 13/719,785, filed Dec. 19, 2012 on behalf of Lawrence Livermore National Laboratory dated Jun. 4, 2015 8 pages.

Non-Final Office Action for U.S. Appl. No. 14/536,513. dated Mar. 24, 2016, 19 pages.

Non-Final Office Action for U.S. Appl. No. 15/499,855, filed Apr. 27, 2017, on behalf of Lawrence Livermore National Security LLC. dated Jan. 11, 2019. 7 pages.

Notice of Allowance for U.S. Appl. No. 12/352,548. dated Apr. 25, 2014, 9 pages.

Notice of Allowance for U.S. Appl. No. 12/352,548. dated Aug. 5, 2014, 8 pages.

Notice of Allowance for U.S. Appl. No. 12/352,548. dated Mar. 12, 2012, 10 pages.

Notice of Allowance for U.S. Appl. No. 13/719,785, filed Dec. 19, 2012 on behalf of Lawrence Livermore National Laboratory dated Feb. 17, 2016 7 pages.

Notice of Allowance for U.S. Appl. No. 14/536,513. dated Jul. 14, 2016, 5 pages.

Notice of Allowance for U.S. Appl. No. 15/499,855, filed Apr. 27, 2017 on behalf of Lawrence Livermore National Security, LLC. dated Mar. 5, 2020. 43 Pages.

Pal S, et al., "Comparison of the nine polymorphic membrane proteins of Chlamydia trachomatis for their ability to induce protective immune responses in mice against a C. muridarum challenge." Vaccine, 35, p. 2543-2549 (2017).

(56) References Cited

OTHER PUBLICATIONS

Pal S, et al., "Immunization with an acellular vaccine consisting of the outer membrane complex of Chlamydia trachomatis induces protection against a genital challenge" Infection and Immunity, vol. 65, No. 8, pp. 3361-3369 (1997).
Pal S, et al., "Immunization with the Chlamydia trachomatis mouse pneumonitis major outer membrane protein can elicit a protective immune response against a genital challenge" Infection and immunity, vol. 69, No. 10, pp. 6240-6247 (2001).
Pal S, et al., "Vaccination with the Chlamydia trachomatis major outer membrane protein can elicit an immune response as protective as that resulting from inoculation with live bacteria" Infection and Immunity, vol. 73, No. 12, pp. 8153-8160 (2005).
Ralli-Jain P, et al., "Enhancement of the protective efficacy of a Chlamydia trachomatis recombinant vaccine by combining systemic and mucosal routes for immunization." Vaccine, 28, pp. 7659-7666 (2010).
Restriction Requirement for U.S. Appl. No. 12/352,548. dated Apr. 25, 2011, 6 pages.
Rodriguez-Maranon M.J. et al., "Prediction of the membrane-spanning Beta-strands of the major outer membrane protein of Chlamydia" Protein Science, 11, pp. 1854-1861 (2002).
Semple et al., "Rational design of cationic lipids for siRNA delivery" Nature Biotechnology Feb. 2010, vol. 28, No. 2, pp. 172-176 + 2 additional pages.
Su H, et al., "Immunogenicity of a chimeric peptide corresponding to T helper and B cell epitopes of the Chlamydia trachomatis major outer membrane protein" Journal of Experimental Medicine, vol. 175, pp. 227-235 (1992).
Sun G, et al., "Protection against an intranasal challenge by vaccines formulated with native and recombinant preparations of the Chlamydia trachomatis major outer membrane protein" Vaccine, 27, pp. 5020-5025 (2009).
Sun G, et al., "Structural and functional analyses of the major outer membrane protein of Chlamydia trachomatis" J Bacteriol, vol. 189, No. 17, pp. 6222-6235 (2007).
Tang G, et al., "EMAN2: an extensible image processing suite for electron microscopy" J Struct Biol, 157, pp. 38-46 (2007).
Tifrea D.F. et al., "Amphipols stabilize the Chlamydia major outer membrane protein and enhance its protective ability as a vaccine" Vaccine, 29, pp. 4623-4631 (2011).
Tifrea D.F. et al., "Increased immunoaccessibility of MOMP epitopes in a vaccine formulated with amphipols may account for the very robust protection elicited against a vaginal challenge with Chlamydia muridarum" The Journal of Immunology, 192, pp. 5201-5213 (2014).
Tu J, et al., "A multi-epitope vaccine based on Chlamydia trachomatis major outer membrane protein induces specific immunity in mice." Acta biochimica et biophysica Sinica, vol. 46, Issue 5, pp. 401-408 (2014).
Vijayalakshmi et al., "A Simple Construction of a Bile Acid Based Dendritic Light Harvesting System" Organic Letters vol. 7 No. 13 p. 2727-2730 (2005).
Wang Y, et al., "Identification of surface-exposed components of MOMP of Chlamydia trachomatis serovar F." Protein Science, 15 pp. 122-134 (2006).
Written Opinion for International Application No. PCT/US2018/030537 filed on May 1, 2018 on behalf of Lawrence Livermore National Security dated Jan. 17, 2019 9 pages.
Xiao et al., "PEG oligocholic acid Telodendrimer micelles for the targeted delivery of doxorubicin to B cell lymphoma" Journal of Controlled Release vol. 155 p. 272-281 (2011).
Xiao K, et al., "Telodendrimer-based nanocarriers for the treatment of ovarian cancer." Ther Deliv, 4(10), pp. 1279-1292 (2013) 24 pages.
Zuris J, et al., "Cationic lipid-mediated delivery of proteins enables efficient protein-based genome editing in vitro and in vivo" Nature Biotechnology, vol. 33, No. 1, p. 73-80 (2015) 8 pages.

European Examination Report for EP Application No. 17763807.9 filed on Mar. 3, 2017 on behalf of Lawrence Livermore National Security, LLC dated Aug. 17, 2022 6 pages.
Extended European Search Report for EP Application No. 17763807.9 filed on Oct. 4, 2018 on behalf of Lawrence Livermore National Security LLC dated Oct. 30, 2019 8 pages.
Frankel D. et al., "Phtoinduced destabilization of bilayer vesicles" J. Am. Chem. Soc. vol. 111 No. 26, 1989, pp. 9262-9263.
Geall A. J. et al., "Nonviral delivery of self-amplifying RNA vaccines" PKAS, vol. 109, No. 36, Sep. 2012, pp. 14604-14609.
Houseley J. et al., "The Many Pathways of RNA Degradation" Cell, vol. 136, Feb. 2009, pp. 763-776.
Kauffman K. J. et al., "Materials for non-viral intracellular delivery of messenger RNA therapeutics" Journal of Controlled Release, vol. 240, 2016, pp. 227-234.
Lamparski H. et al., "Photoinduced destabilization of liposomes" Biochemistry, vol. 31 No. 3, 1992, pp. 685-694.
Midoux P. et al. "Lipid-based mRNA vaccine delivery systems" Expert Rev. Vaccines, 2014, pp. 1-14.
Mueller A. et al., "Supramolecular materials via polymerization of mesophases of hydrated amphiphiles" Chem. Rev. 102(3), 2002, pp. 727-757.
Pardi N. et al., "Expression kinetics of nucleoside-modified mRNA delivered in lipid nanoparticles to mice by various routes." J. Control Release, Nov. 2015, pp. 1-18.
Pardi N. et al., "mRNA vaccines—a new area in vaccinology" Nature Reviews, vol. 17, Apr. 2018, pp. 261-279.
Ramachandran S. et al., "Delivery Strategies for mRNA Vaccines" Pharmaceutical Medicine, vol. 36, Jan. 2022, pp. 11-20.
Reichmuth A. M. et al., "mRNA vaccine delivery using lipid nanoparticles" Ther. Deliv., vol. 7, No. 5, Apr. 2016, pp. 319-334.
Schmidt S.T. et al., "Liposome-Based Adjuvants for Subunit Vaccines: Formulation Strategies for Subunit Antigens and Immunostimilators" Pharmaceutics, Mar. 2016, vol. 8, No. 7, pp. 1-22.
Sligar, "Protocols for Preparation of Nanodiscs", (Mar. 4, 2008), 7 pages.
Tyminski P. N. et al., "Rhodopsin in polymerized bilayer membranes" J. Am. Chem. Soc. vol. 107 No. 25, 1985, pp. 7769-7770.
Tyminski P.N. et al., "Reconstitution of Rhodopsin and the cGMP cascade in polymerized bilayer membranes" Biochemistry, vol. 27 No. 8, 1988, pp. 2696-2705.
Weissman D. et al., "mRNA transcript therapy" Expert Rev. Vaccines, 2014, pp. 1-17.
He, W. et al. "Cationic HDL mimetics enhance in vivo delivery of self-replicating mRNA", Nanomedicine, Feb. 24, 2020: 102154. 20 pages. Doi:10.1016/j.nano.2020.102154.
"Technical Bulletin: pSV-β Galactosidase Control Vector Instructions for Use of Product E1081", Promega, Revised Sep. 2006. 9 pages. Website: www.promega.com.
Notice of Allowance for U.S. Appl. No. 17/308,921, filed May 5, 2021 in the name of Lawrence Livermore National Security, LLC. dated Mar. 9, 2023. 10 pages.
Final Office Action for U.S. Appl. No. 15/755,018, filed Feb. 23, 2018 on behalf of Lawrence Livermore National Security, LLC dated Nov. 17, 2022 20 pages.
Non-Final Office Action for U.S. Appl. No. 17/308,921, filed May 5, 2021 in the name of Lawrence Livermore National Security, LLC. dated Nov. 10, 2022. 12 pages.
Non-Final Office Action for U.S. Appl. No. 16/082,924, filed Sep. 6, 2018 in the name of Lawrence Livermore National Security, LLC, et al. dated Dec. 2, 2022. 25 pages.
Final Office Action for U.S. Appl. No. 16/082,924, filed Sep. 6, 2018 on behalf of Lawrence Livermore National Security, LLC dated Sep. 25, 2023 25 pages.
Non-Final Office Action for U.S. Appl. No. 17/561,625, filed Dec. 23, 2021 on behalf of Lawrence Livermore National Security, LLC dated Oct. 5, 2023, 8 pages.
Cai L. et al., "A facile surfactant critical micelle concentration determination"Chem Commun, vol. 47 No. 19,May 21, 2011, pp. 5527-5529.
Castro M. J. L. et al., "A simplified Method for the Determication of Critical Micelle Concentration" Journal of Chemical Education, vol. 78, No. 3, Mar. 2001, pp. 347-348.

(56) References Cited

OTHER PUBLICATIONS

Heerklotz H. et al., "The Enthalpy of Acyl Chain Packing and the Apparent Water-Accessible Apolar Surface Area of Phospholipids" *Biophysical Journal*, vol. 80, Jan. 2001, pp. 271-290.

Held P. "Rapid Critical Micelle Concentration (CMC) Determination Using Fluorescence Polarization" *Bio Tek Instruments. Inc.*, Sep. 1, 2021, 9 pages.

Huibers P.D.T. et al., "Predicition of Critical Micelle Concentration Using a Quantitative Structure—Property Relationship Approach. 1. Nonionic Surfactants" *Langmuir*, vol. 12 No. 6, 1996, pp. 1462-1470.

Mukerjee P. et al., "Critical Micelle Concentrations of Aqueous Surfactant Systems" *United States Department of Commerce, National Bureau of Standards*, Feb. 1971, 242 pages.

Qin S. et al., "Predicting Critical Micelle Concentrations for Surfactants Using Graph Convolutional Neural Networks" *J. Phys. Chem. B*, 2021, vol. 125, pp. 10610-10620.

Wielandt A. G. et al., "Specific Activation of the Plant P-type Plasma Membrane $H^+$-ATPase by Lysophospholipids Depends on the Autoinhibitory N- and C-terminal Domains" *Journal of Biological Chemistry*, vol 290 No. 26, Jun. 26, 2015, pp. 16281-16291.

Yu. D et al., "Determination of Critical Concentrations by Synchronous Fluorescence Spectrometry" Electronic Supplementary Information, *The Royal Society of Chemistry*, 2011, pp. S1-S18.

Final Office Action for U.S. Appl. No. 15/755,018, filed Feb. 23, 2018 on behalf of Lawrence Livermore National Security, LLC Mail Date: Nov. 17, 2022 20 pages.

Non-Final Office Action for U.S. Appl. No. 17/308,921, filed May 5, 2021 in the name of Lawrence Livermore National Security, LLC. Mailed on Nov. 10, 2022. 12 pages.

Non-Final Office Action for U.S. Appl. No. 16/082,924, filed Sep. 6, 2018 in the name of Lawrence Livermore National Security, LLC, et al. Mailed on Dec. 2, 2022. 25 pages.

\* cited by examiner

| NLP composition | NLP:RNA | Size (nm) | Stdev (nm) |
|---|---|---|---|
| Replicon alone | | 93.7 | 29.3 |
| 2% MVL5_E4 | | 36.4 | 5.9 |
| 2% MVL5_E4 | 50:1 | 103.6 | 63.2 |
| 2% MVL5_E4 | 250:1 | 118.0 | 59.1 |
| 2% MVL5_E4 | 500:1 | 140.8 | 12.2 |
| 5% MVL5_E4 | | 30.4 | 6.9 |
| 5% MVL5_E4 | 50:1 | 57.3 | 14.3 |
| 5% MVL5_E4 | 250:1 | 74.3 | 42.9 |
| 5% MVL5_E4 | 500:1 | 46.7 | 10.1 |
| 10% DDAB_E4 | | 35.9 | 14.9 |
| 10% DDAB_E4 | 50:1 | 89.1 | 41.6 |
| 10% DDAB_E4 | 250:1 | 151.8 | 70.3 |
| 10% DDAB_E4 | 500:1 | 26.8 | 2.5 |

| NLP composition | NLP:RNA | Size (nm) | Stdev (nm) |
|---|---|---|---|
| Replicon alone | | 93.7 | 29.3 |
| 20% DMTAP_A1 | | 18.8 | 9.3 |
| 20% DMTAP_A1 | 50:1 | 210.3 | 14.3 |
| 20% DMTAP_A1 | 250:1 | 156.9 | 26.7 |
| 20% DMTAP_A1 | 500:1 | 216.5 | 27.1 |
| 10% DDAB_A1 | | 22.83 | 3.5 |
| 10% DDAB_A1 | 50:1 | 62.65 | 25.7 |
| 10% DDAB_A1 | 250:1 | 494.4 | 364.8 |
| 10% DDAB_A1 | 500:1 | 275.8 | 146.3 |

FIGURE 12

NANOLIPOPROTEIN PARTICLES AND RELATED COMPOSITIONS METHODS AND SYSTEMS FOR LOADING RNA

CROSS-REFERENCE TO RELATED APPLICATIONS

This application claims priority under 35 USC § 119(e) to U.S. Application Ser. No. 62/500,433 filed May 2, 2017. The disclosure of the prior application is considered part of and is incorporated by reference in the disclosure of this application in its entirety.

STATEMENT OF GOVERNMENT GRANT

The invention was made with Government support under Contract No. DE-AC52-07NA27344 between the U.S. Department of Energy and Lawrence Livermore National Security, LLC, for the operation of Lawrence Livermore National Security. The Government has certain rights to the invention.

FIELD

The present disclosure relates to nanolipoprotein particles (NLPs) and, in particular, nanolipoprotein particles incorporated with cationic lipid compounds and related compositions methods and systems.

BACKGROUND

Nanolipoprotein particles are nanometer-sized particles usually comprised of an amphipathic lipid bilayer and an apolipoprotein. NLPs have been used for various biotechnology applications, such as membrane protein stabilization/solubilization, drug delivery, and in particular vaccine delivery, and diagnostic imaging.

In some instances, NLPs can self-assemble under appropriate conditions into nano-scale amphipathic apolipoprotein-stabilized lipid bilayer particles possibly comprising additional lipid or protein molecules inserted into or attached to the amphipathic component of the NLP. The self-assembled particles are typically formed by an apolipoprotein encircling a nanometer scale lipid bilayer defining a nanolipoprotein particle.

Despite the advancement of this technology, providing NLPs including desired functionalities and/or with a desired stability can be challenging.

SUMMARY

Provided herein are nanolipoprotein particles, and related compositions, methods and systems, which comprise one or more membrane forming lipids, one or more cationic lipids and a scaffold protein. In several embodiments, nanolipoprotein particles herein described can be used as a delivery vehicle to deliver in vitro or in vivo large nucleic acids complex with improved transfection efficiency.

According to a first aspect, a cationic nanolipoprotein particle is described. The cationic nanolipoprotein particle comprises one or more membrane forming lipids, one or more cationic lipids and one or more scaffold proteins, the membrane forming lipid and the cationic lipids arranged in a discoidal membrane lipid bilayer stabilized by the scaffold protein.

According to a second aspect, a cationic-NLPs-polynucleotide complex is described. The cationic-NLPs-polynucleotide complex comprises a polynucleotide molecule attached to one or more cationic NLPs wherein each cationic NLP comprising one or more cationic lipids and a membrane forming lipid arranged in a discoidal membrane lipid bilayer stabilized by a scaffold protein. In particular, in some embodiments, cationic-NLPs-polynucleotide complex polynucleotides and NLPs are included in a ratios polynucleotide:NLPs of 2:1 or higher.

According to a third aspect, a cationic-NLPs-polynucleotide complex is described. The cationic-NLPs-polynucleotide complex comprises a polynucleotide molecule, in particular a polynucleotide having at least 200 bases, from 200 to 5000 bases, at least 5,000 bases, from 5,000 to 15,000 bases and higher than 15,000 bases attached to a plurality of cationic NLPs each cationic NLP comprising one or more cationic lipids and a membrane forming lipid arranged in a discoidal membrane lipid bilayer stabilized by a scaffold protein.

According to a fourth aspect, a method and system to provide a polynucleotide-nanolipoprotein complex is described. The method comprises contacting the polynucleotide with a plurality of cationic nanolipoprotein particles each comprising a membrane lipid bilayer stabilized by a scaffold protein in a discoidal configuration with the membrane lipid bilayer comprising one or more cationic lipids, to provide a polynucleotide cationic-nanolipoprotein-complex comprising the polynucleotide attached to the plurality of cationic nanolipoprotein particles.

The system comprises one or more polynucleotide molecules, one or more cationic nanolipoprotein particles comprising one or more cationic lipids and one or more membrane forming lipids within a membrane lipid bilayer stabilized by a scaffold protein. In the system, the one or more polynucleotide and the one or more cationic nanolipoprotein particles provides are for simultaneous combined or sequential use in the method to provide a polynucleotide nanolipoprotein complex herein described.

According to a fifth aspect, a method and system to provide a cationic nanolipoprotein particle, are described. The method comprises contacting a membrane forming lipid and one or more cationic lipids with a scaffold protein to provide a discoidal lipid bilayer comprising the membrane forming lipid and the one or more cationic lipids stabilized by the scaffold protein.

The system comprises one or more membrane-forming lipids, one or more cationic lipids, and a scaffold protein. In the system, assembly of the one or more membrane forming lipids and the scaffold protein provides a nanolipoprotein particle in which the one or more cationic lipids are comprised within a membrane lipid bilayer stabilized by the scaffold protein.

According to a sixth aspect, a composition is described comprising one or more cationic nanolipoprotein particles and/or one or more cationic-NLPs-polynucleotide complexes, together with an acceptable vehicle. In some embodiments, the composition can be a pharmaceutical composition and the acceptable vehicle can be a pharmaceutically acceptable vehicle. In some of those embodiments, the composition can be a vaccine.

According to a seventh aspect, a method and system to deliver one or more polynucleotide molecules to target environment is described. The method comprises contacting the target environment with one or more cationic-NLPs-polynucleotide complexes herein described comprising the one or more polynucleotide molecules.

The system comprises one or more cationic nanolipoprotein particles herein described and one or more polynucleotide molecules for combined use in the method to deliver one or more polynucleotide molecules herein described.

According to additional aspects, methods and systems, comprising forming and using the cationic nanolipoprotein particles herein described are also provided in the present disclosure. Methods and systems to perform an assay on nucleotide molecules loaded in the cationic-NLP-nucleotide complexes of the present disclosure are also described.

Cationic nanolipoprotein particles and related complexes, compositions, methods and systems, in several embodiments provide an efficient, versatile and reproducible delivery of RNA replicon molecules. In particular, the cationic NLP-replicon complex formulations are stable, easily prepared and do not fully encapsulate the replicon while they can provide protection against RNase degradation, shielding access to outside molecules as well as increasing the replicon's in vivo transfection efficiency.

Cationic nanolipoprotein particles and related complexes, compositions, methods and systems, in several embodiments show in several embodiments an ability to load RNA replicon molecules having a 10,000 bp or higher.

Cationic nanolipoprotein particles and related complexes, compositions, methods and systems, in several embodiments allow increased transfection of an RNA replicon with respect to unformulated replicon through in vivo gene expression in a mouse model.

Cationic nanolipoprotein particles and related complexes, compositions, methods and systems, in several embodiments can be used to deliver the RNA with a ratio between the number of nitrogen atoms in the cationic NLPs and the number of phosphate groups in the RNA, 10-fold lower compared to conventional approaches.

The nanolipoprotein particles and related compositions, methods and systems herein described can be used in connection with various applications wherein highly efficient in vivo nucleic acids delivery and transfection is desired. For example, the nanolipoprotein particles herein described and related compositions methods and systems can be used as a vehicle for delivery of compounds such as therapeutics to a specific target destination, as a platform for immunostimulating agents, vaccine development and use, and/or to contain cell-targeting moieties. Additional exemplary applications include uses of nanolipoprotein particles in several fields including basic biology research, applied biology, bio-engineering, bio-energy, molecular biology, medical research, medical diagnostics, therapeutics, biofuels, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 12 shows a Table of results of the average size of replicon RNA alone, NLP alone with ApoE4 or ApoA1 scaffold proteins, and NLP:RNA complexes at the ratios indicated, assessed using Dynamic Light Scattering (DLS) analysis.

FIG. 20A shows the result of a SEC screen of NLP formation with ApoAI, DMPC, DDAB (10%). FIG. 20B shows the result of a SEC screen of NLP formation with apoE4, DMPC, MVL5 (2%). FIG. 20C shows the result of a SEC screen of NLP formation with apoAI, DMPC, DMEPC (40%). These telodendrimers were tested with cationic NLPs binned into high efficacy (FIG. 20A), medium efficacy (FIG. 20B), or low efficacy (FIG. 20C), based on previous in vivo assessments of luciferase intensity. SEC traces (plotting absorbance intensity as a function of retention time) were used to identify those formulations that formed the most homogeneous species of NLPs, based on the presence of a single SEC peak. Formulations chosen for subsequent in vivo testing are indicated with check marks.

DETAILED DESCRIPTION

Figure 1:
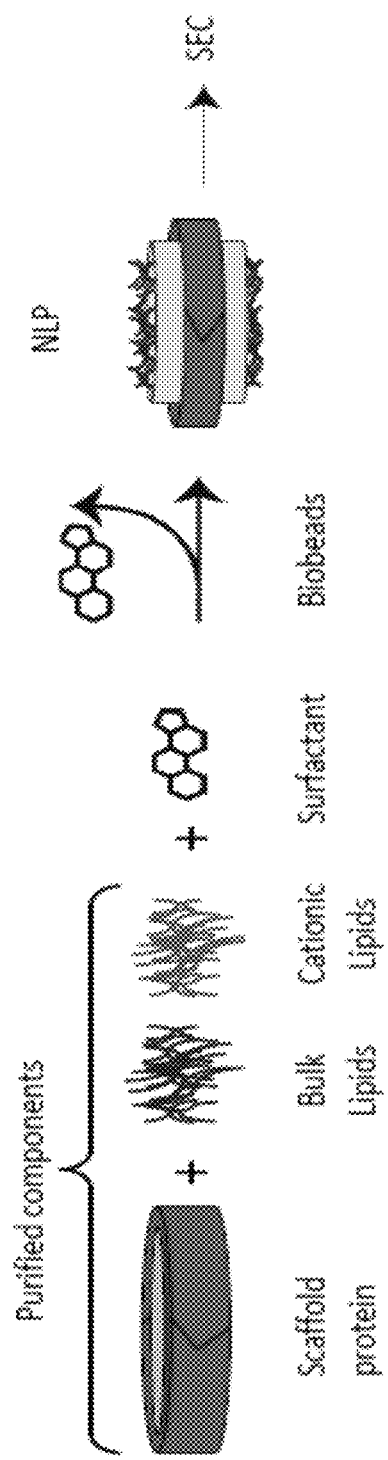
FIG. 1 shows a schematic illustration of exemplary cationic NLP (cationic-NLP) formation, wherein a scaffold protein of interest, bulk lipids, and cationic lipids are mixed with surfactant and incubated with biobeads overnight. The next morning, cationic-NLPs are filtered and tested by size exclusion chromatography (SEC) to check for proper homogeneity, peak distribution, and size of the cationic-NLP peak. The different steps are schematically indicated by arrows.

Provided herein are nanolipoprotein particles and related compositions, methods and systems.

The term "nanolipoprotein particle" "nanodisc" "rHDL" or "NLP" as used herein indicates a supramolecular complex formed by a membrane forming lipid arranged in a lipid bilayer stabilized by a scaffold protein. The membrane forming lipids and scaffold protein are components of the NLP. In particular the membrane forming lipid component is part of a total lipid component, (herein also membrane lipid component or lipid component) of the NLP together with additional lipids such as functionalized lipids and/or lysolipids, that can further be included in the NLPs as will be understood by a skilled person upon reading of the present disclosure. The scaffold protein component is part of a protein component of the NLP together with additional proteins such as membrane proteins, target proteins and other proteins that can be further included as components of the NLPs as will be understood by a skilled person upon reading of the present disclosure. Additional components can be provided as part of the NLP herein described as will be understood by a skilled person. In particular, the membrane lipid bilayer can attach membrane proteins or other amphipathic compounds through interaction of respective hydrophobic regions with the membrane lipid bilayer. The membrane lipid bilayer can also attach proteins or other molecules through anchor compounds or functionalized lipids as will be understood by a skilled person upon reading of the disclosure. In a nanolipoprotein particle, the membrane lipid bilayer can be confined in a discoidal configuration by the scaffold protein. Predominately discoidal in shape, nanolipoprotein particles typically have diameters between 5 to 25 nm, share uniform heights between 3 to 6 nm and can be produced in yields ranging between 30 to 90%. Techniques suitable for detecting the size and dimension of the NLP comprise Transmission Electron Microscopy (TEM), Atomic Force Microscopy (AFM) Dynamic Light Scattering (DLS) and additional techniques identifiable by a skilled person.

In particular, in embodiments herein described, the nanolipoprotein particle can be formed by a lipid bilayer confined in a discoidal configuration by a scaffold protein. In this configuration, the lipid bilayer confined by the scaffold protein can be 4-7 nanometers in thickness, the nanolipoprotein particle can have an overall diameter of 6-30 nanometers, and the scaffold protein on the particle can have a thickness of 1-2 nanometers. In some embodiments, an entire NLP structure can be up to 600 kilodaltons in weight.

The particular membrane forming lipid, scaffold protein, the lipid to protein ratio, and the assembly parameters determine the size and homogeneity of nanolipoprotein particles as will be understood by a skilled person. In the nanolipoprotein particle the membrane forming lipids are typically arranged in a membrane lipid bilayer confined by the scaffold protein in a discoidal configuration as will be understood by a skilled person.

The term "membrane forming lipid" or "amphipathic lipid" as used herein indicates a lipid possessing both hydrophilic and hydrophobic moieties that in an aqueous environment assembles into a lipid bilayer structure that consists of two opposing layers of amphipathic molecules known as polar lipids. Each polar lipid has a hydrophilic moiety, i.e. a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols, alkylphosphocholines and the like. Amphipathic lipids include but are not limited to membrane lipids, i.e. amphipathic lipids that are constituents of a biological membrane, such as phospholipids like dimyristoylphosphatidylcholine (DMPC) or dioleoylphosphoethanolamine (DOPE) or dioleoylphosphatidylcholine (DOPC), or dipalmitoylphosphatidylcholine (DPPC). In a preferred embodiment, the lipid is dimyristoylphosphatidylcholine (DMPC).

The term "scaffold protein" as used herein indicates any amphipathic protein that is capable of self-assembly with amphipathic lipids in an aqueous environment, organizing the amphipathic lipids into a bilayer disc, and comprise apolipoproteins, lipophorins, derivatives thereof (such as truncated and tandemly arrayed sequences) and fragments thereof (e.g. peptides or fragments) which maintains the amphipathic nature and capability of self-assembly, such as apolipoprotein E4 (22 Kd fragment), lipophorin III, apolipoprotein A-1 and the like. In general, scaffold proteins have an alpha helical secondary structure in which a plurality of hydrophobic amino acids form a hydrophobic face and a plurality of hydrophilic amino acids form an opposing hydrophilic face. In some embodiments, rationally designed amphipathic peptides and synthetic apolipoproteins which maintain an amphipathic structure and capability of self-assembly can serve as a scaffold protein of the NLP.

The term "apolipoprotein" as used herein indicates an amphipathic protein that binds lipids to form lipoproteins. The term "amphipathic" pertains to a molecule containing both hydrophilic and hydrophobic properties. Exemplary amphipathic molecules comprise molecules having hydrophobic and hydrophilic regions/portions in its structure. Examples of biomolecules which are amphipathic include but not limited to phospholipids, cholesterol, glycolipids, fatty acids, bile acids, saponins, and additional lipids identifiable by a skilled person. A "lipoprotein" as used herein indicates a biomolecule assembly that contains both proteins and lipids. In particular, in lipoproteins, the protein component surrounds or solubilizes the lipid molecules enabling particle formation. Exemplary lipoproteins include the plasma lipoprotein particles classified under high-density (HDL) and low-density (LDL) lipoproteins, which enable fats and cholesterol to be carried in the blood stream, the transmembrane proteins of the mitochondrion and the chloroplast, and bacterial lipoproteins. In particular, the lipid components of lipoproteins are insoluble in water, but because of their amphipathic properties, apolipoproteins such as certain Apolipoproteins A and Apolipoproteins B and other amphipathic protein molecules can organize the lipids in a bilayer orientation with exposed hydrophilic moieties, creating the lipoprotein particle that is itself water-soluble, and can thus be carried through water-based circulation (e.g. blood, lymph in vivo or in vitro). Apolipoproteins known to provide the protein components of the lipoproteins can be divided into six classes and several sub-classes, based on the different structures and functions. Exemplary apolipoprotein known to be able to form lipoproteins comprise Apolipoproteins A (apo A-I, apo A-II, apo A-IV, and apo A-V), Apolipoproteins B (apo B48 and apo B100), Apolipoproteins C (apo C-I, apo C-II, apo C-III, and apo C-IV), Apolipoproteins D, Apolipoproteins E, and Apolipoproteins H. For example, apolipoproteins B can form low-density lipoprotein particles, and have mostly beta-sheet structure and associate with lipid droplets irreversibly, while Apolipoprotein A1 comprise alpha helices and can associate with lipid droplets reversibly forming high-density lipoprotein particles.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine ($—NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In embodiments herein described, cationic nanolipoprotein particles comprise one or more cationic lipids within the lipid bilayer also comprising one or more membrane forming lipids.

The term "cationic lipids" as used herein refers to a subset of polar lipids that are characterized as having a hydrophobic region to anchor in the bilayer and a polar or positively-charged head group that is presented on the bilayer surface. In some cases, the head groups are ionizable head groups that are uncharged at a pH above their pK but capable of becoming positively charged at a pH below their pK.

In some embodiments, cationic lipids herein described comprise lipids of Formula (I):

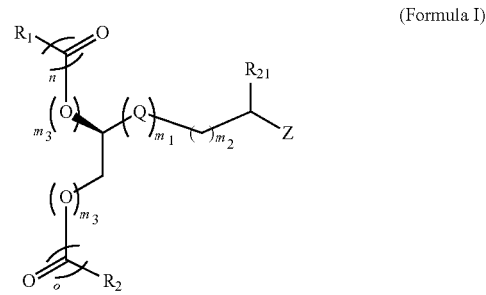

(Formula I)

R1 and R2 are independently selected from H and a $C_7$-$C_{29}$ branched or straight, substituted or unsubstituted aliphatic carbon chain;

$R_{21}$ is H, OH, or a carboxy group;

Q in Formula I is selected from:

(Formula V)

(Formula VI)

(Formula VII)

(Formula VIII)

$m_1$=0-1; $m_2$=0-3; $m_3$=0-1 and n and o are independently 0 and 1;

Z is a moiety of Formula (II) or Formula (III) or Formula (IV), wherein the moiety of Formula (II) is

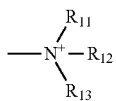

(Formula II)

in which $R_{11}$, $R_{12}$ and $R_{13}$ are independently H or a $C_1$-$C_4$ branched or straight aliphatic carbon chain;

the moiety of Formula (III) is

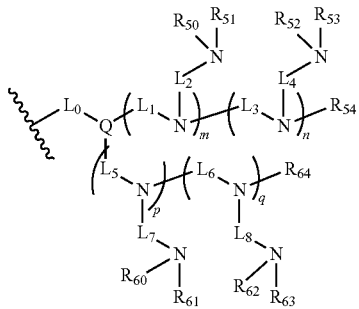

(Formula III)

Wherein

Q in Formula III is N or CH;

m, n, p and q are independently 0-3 and m+n+p+q is equal or greater than 1;

$L_0$-$L_8$ are independently a divalent group selected from $C_{1-6}$ alkylidenyl, $C_{1-6}$ heteroalkylidenyl, $C_{3-6}$ cycloalkylidenyl, and $C_{3-6}$ heterocycloalkylidenyl, wherein each of the alkylidenyl, heteroalkylidenyl, cycloalkylidenyl, and heterocycloalkylidenyl is optionally substituted with one or more substituents independently selected from $C_{1-4}$ alkyl, haloalkyl, $C_{1-4}$ alkoxy, amino, alkylamino, dialkylamino, oxo groups;

$R_{50}$-$R_{54}$, $R_{60}$-$R_{64}$ are independently a monovalent group selected from H, $C_{1-6}$ alkyl, $C_{1-6}$ heteroalkyl, $C_{3-6}$ cycloalkyl, and $C_{3-6}$ heterocycloalkyl, wherein each of the alkyl, heteroalkyl, cycloalkyl, and heterocycloalkyl is optionally substituted with one or more substituents independently selected from $C_{1-4}$ alkyl, haloalkyl, $C_{1-4}$ alkoxy, amino, $C_{1-4}$ alkylamino, $C_{1-4}$ dialkylamino, or a oxo group; and the moiety of Formula (IV) is

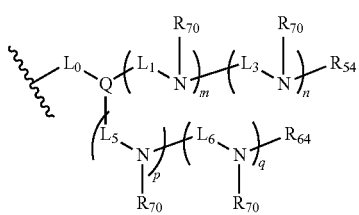

(Formula IV)

in which Q in Formula IV is N or CH;

m, n, p and q are independently 0-3 and m+n+p+q is equal or greater than 1;

$L_0$-$L_1$; $L_3$ and $L_5$-$L_6$ are independently a divalent group selected from $C_{1-6}$ alkylidenyl, $C_{1-6}$ heteroalkylidenyl, $C_{3-6}$ cycloalkylidenyl, and $C_{3-6}$ heterocycloalkylidenyl, wherein each of the alkylidenyl, heteroalkylidenyl, cycloalkylidenyl, and heterocycloalkylidenyl is optionally substituted with one or more substituents independently selected from $C_{1-4}$ alkyl, haloalkyl, $C_{1-4}$ alkoxy, amino, alkylamino, dialkylamino, oxo groups;

$R_{54}$, $R_{64}$ and $R_{70}$ are independently a monovalent group selected from H, $C_{1-6}$ alkyl, $C_{1-6}$ heteroalkyl, $C_{3-6}$ cycloalkyl, and $C_{3-6}$ heterocycloalkyl, wherein each of the alkyl, heteroalkyl, cycloalkyl, and heterocycloalkyl is optionally substituted with one or more substituents independently selected from $C_{1-4}$ alkyl, haloalkyl, $C_{1-4}$ alkoxy, amino, $C_{1-4}$ alkylamino, $C_{1-4}$ dialkylamino, or a oxo group.

As used herein, the term "aliphatic" refers to an alkyl, alkenyl or alkynyl group which can be substituted or unsubstituted, linear, branched or cyclic.

As used herein the term "alkyl" as used herein refers to a linear, branched, or cyclic, saturated hydrocarbon group formed by a carbon chain. As used herein the term "carbon chain" indicates a linear or branched line of connected carbon atoms. An alkyl carbon chain typically although not necessarily containing 1 to about 18 carbon atoms (±1 atom), preferably 1 to about 6 carbon atoms (±1 atom), such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 6 carbon atoms (±1 atom). The term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

As used herein the term "alkenyl" indicates a linear, branched, or cyclic hydrocarbon group that contains at least one carbon-carbon double bond. As used herein the term "alkynyl" indicates a linear, branched, or cyclic hydrocarbon group that contains at least one carbon-carbon triple bond.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 12 carbon atoms, and particularly preferred aryl groups contain 5 to 6 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, such as nitrogen, oxygen or sulfur.

As used herein the terms "heteroatom-containing" or "hetero-" indicated in connection with a group, refers to a hydrocarbon group in which one or more carbon atoms is replaced with an atom other than carbon, e.g., nitrogen, oxygen, sulfur, phosphorus or silicon, typically nitrogen, oxygen or sulfur. Exemplary "heteroatoms" comprise as N, O, S and P, and can be present in a compound by a covalent bond to each of two carbon atoms, thus interrupting the two carbon atoms. Accordingly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, and addition group identifiable by a skilled person.

The term "aralkyl" as used herein refers to an alkyl group with an aryl substituent, and the term "alkaryl" as used herein refers to an aryl group with an alkyl substituent, wherein "aryl" and "alkyl" are as defined above. In some embodiments, alkaryl and aralkyl groups contain 6 to 12 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, and the like. The terms "alkaryloxy" and "aralkyloxy" refer to substituents of the formula —OR wherein R is alkaryl or aralkyl, respectively, as defined.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents. As used herein, a "substituent" is an atom or group of atoms substituted in place of a hydrogen atom on the main chain of a hydrocarbon. Examples of such substituents include, without limitation: functional groups such as, hydroxyl, sulfhydryl, $C_1$-$C_{12}$ alkoxy, $C_2$-$C_{12}$ alkenyloxy, $C_2$-$C_{12}$ alkynyloxy, $C_5$-$C_{12}$ aryloxy, $C_6$-$C_{12}$ aralkyloxy, $C_6$-$C_{12}$ alkaryloxy, acyl (including $C_2$-$C_{12}$ alkylcarbonyl (—CO-alkyl) and $C_6$-$C_{12}$ arylcarbonyl (—CO-aryl)), acyloxy (—O-acyl, including $C_2$-$C_{12}$ alkylcarbonyloxy (—O—CO-alkyl) and $C_6$-$C_{12}$ arylcarbonyloxy (—O—CO-aryl)), $C_2$-$C_{12}$ alkoxycarbonyl (—(CO)—O-alkyl), $C_6$-$C_{12}$ aryloxycarbonyl (—(CO)—O-aryl),$C_2$-$C_{12}$ alkylcarbonato (—O—(CO)—O-alkyl), $C_6$-$C_{12}$ arylcarbonato (—O—(CO)—O-aryl), carboxy (—COOH), carboxylato (—COO$^-$), carbamoyl (—(CO)—NH$_2$), mono-($C_1$-$C_{12}$ alkyl)-substituted carbamoyl (—(CO)—NH($C_1$-$C_{12}$ alkyl)), di-($C_1$-$C_{12}$ alkyl)-substituted carbamoyl (—(CO)—N($C_1$-$C_{12}$ alkyl)$_2$), mono-($C_5$-$C_{12}$ aryl)-substituted carbamoyl (—(CO)—NH-aryl), di-($C_5$-$C_{12}$ aryl)-substituted carbamoyl (—(CO)—N($C_5$-$C_{12}$ aryl)$_2$), di-N—($C_1$-$C_6$ alkyl), N—($C_5$-$C_{12}$ aryl)-substituted carbamoyl, thiocarbamoyl (—(CS)—NH$_2$), mono-($C_1$-$C_{12}$ alkyl)-substituted thiocarbamoyl (—(CO)—NH($C_1$-$C_{12}$ alkyl)), di-($C_1$-$C_{12}$ alkyl)-substituted thiocarbamoyl (—(CO)—N($C_1$-$C_6$ alkyl)$_2$), mono-($C_5$-$C_{12}$ aryl)-substituted thiocarbamoyl (—(CO)—NH-aryl), di-($C_5$-$C_6$ aryl)-substituted thiocarbamoyl (—(CO)—N($C_5$-$C_6$ aryl)$_2$), di-N—($C_1$-$C_6$ alkyl), N—($C_5$-$C_6$ aryl)-substituted thiocarbamoyl, carbamido (—NH—(CO)—NH$_2$), cyano(—C≡N), cyanato (—O—C≡N) thiocyanato (—S—C≡N), formyl (—(CO)—H), thioformyl (—(CS)—H), amino (—NH$_2$), mono-($C_1$-$C_{12}$ alkyl)-substituted amino, di-($C_1$-$C_{12}$ alkyl)-substituted amino, mono-($C_5$-$C_{12}$ aryl)-substituted amino, di-($C_5$-$C_6$ aryl)-substituted amino, $C_2$-$C_{12}$ alkylamido (—NH—(CO)-alkyl), $C_6$-$C_{12}$ arylamido (—NH—(CO)—aryl), imino (—CR=NH where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), $C_2$-$C_{12}$ alkylimino (—CR=N(alkyl), where R=hydrogen, $C_1$-$C_{12}$ alkyl, $C_5$-$C_{12}$ aryl, $C_6$-$C_{12}$ alkaryl, $C_6$-$C_2$ aralkyl, etc.), arylimino (—CR=N(aryl), where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), nitro (—NO$_2$), nitroso (—NO), sulfo (—SO$_2$—OH), sulfonato (—SO$_2$—O$^-$), $C_1$-$C_{12}$ alkylsulfanyl (—S-alkyl; also termed "alkylthio"), $C_5$-$C_{12}$ arylsulfanyl (—S-aryl; also termed "arylthio"), $C_1$-$C_{12}$ alkylsulfinyl (—(SO)-alkyl), $C_5$-$C_{12}$ arylsulfinyl (—(SO)-aryl), $C_1$-$C_{12}$ alkylsulfonyl (—SO$_2$-alkyl), $C_5$-$C_{12}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$), phospho (—PO$_2$), phosphino (—PH$_2$), silyl (—SiR$_3$ wherein R is hydrogen or hydrocarbyl), and silyloxy (—O-silyl); and the hydrocarbyl moieties $C_1$-$C_{12}$ alkyl (preferably $C_1$-$C_{12}$ alkyl, more preferably $C_1$-$C_6$ alkyl), $C_2$-$C_{12}$ alkenyl (preferably $C_2$-$C_{12}$ alkenyl, more preferably $C_2$-$C_6$ alkenyl), $C_2$-$C_{12}$ alkynyl (preferably $C_2$-$C_{12}$ alkynyl, more preferably $C_2$-$C_6$ alkynyl), $C_5$-$C_{12}$ aryl (preferably $C_5$-$C_{12}$ aryl), $C_6$-$C_{12}$ alkaryl (preferably $C_6$-$C_{12}$ alkaryl), and $C_6$-$C_{12}$ aralkyl (preferably $C_6$-$C_{12}$ aralkyl).

In some embodiments, the cationic lipids comprise lipids of Formula (IX):

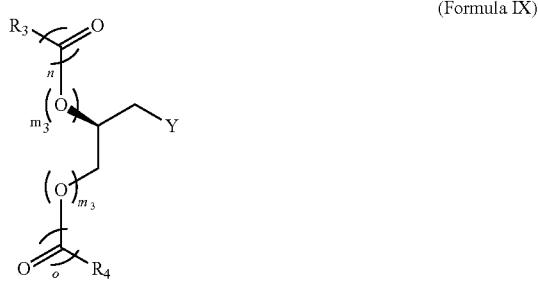

(Formula IX)

wherein
$R_3$, $R_4$ are independently a $C_7$-$C_{29}$ branched or straight, substituted or unsubstituted aliphatic carbon chain;
Y is a moiety of formula (III), (IV) or (X), wherein the moiety of Formula (X) is

(Formula X)

in which $R_{11}$, $R_{12}$ and $R_{13}$ are independently H or a $C_1$-$C_4$ branched or straight aliphatic carbon chain;
n and o are independently 0 and 1; and $m_3$=0 or 1.

In some embodiments, cationic lipids comprise lipids of Formula (XI)

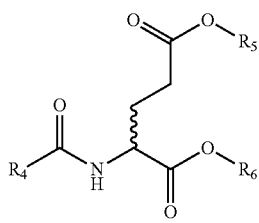

(Formula XI)

wherein $R_4$, $R_5$ and $R_6$ are independently H and $C_7$-$C_{29}$ branched or straight, substituted or unsubstituted aliphatic carbon chain, and at least one of $R_4$, $R_5$ and $R_6$ contains at least one amino nitrogen and wherein at least one of $R_4$, $R_5$ and $R_6$ is H.

In some embodiments, cationic lipids comprise lipids of Formula (XII)

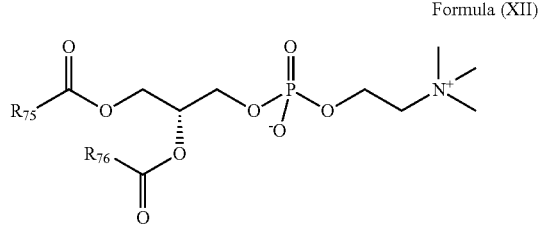

Formula (XII)

wherein $R_{75}$ and $R_{76}$ are independently selected from a $C_7$ to $C_{13}$ alkyl, $C_7$ to $C_{13}$ alkenyl group.

In some embodiments, cationic lipids comprise lipids of Formula (XIII)

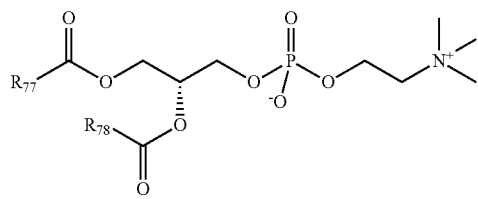

Formula (XIII)

wherein $R_{77}$ and $R_{78}$ are independently selected from a $C_{14}$ to $C_{19}$ alkyl, $C_{14}$ to $C_{19}$ alkenyl group.

In some embodiments, cationic lipids herein described comprise one or more multivalent cationic lipids. The term "multivalent cationic lipid" refers to a subset of cationic lipid having a hydrophobic region and a head group bearing a positive charge varied from +2 to +16. In contrast, the term "monovalent cationic lipid" therefore refers to a subset of cationic lipid having a hydrophobic region and a head group bearing a positive charge of +1.

In some embodiments, the multivalent cationic lipids herein described have a head group of Formula (XIV):

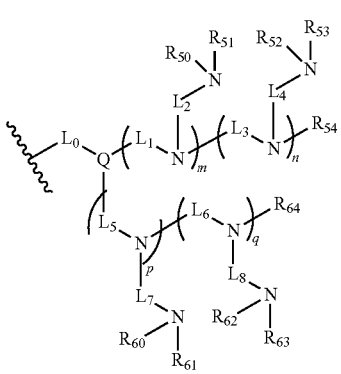

(Formula XIV)

wherein
Q in Formula XIV is N or CH;
m, n, p and q are independently 0-3 and m+n+p+q is equal or greater than 1;
$L_0$-$L_8$ are independently a divalent group selected from $C_{1-6}$ alkylidenyl, $C_{1-6}$ heteroalkylidenyl, $C_{3-6}$ cycloalkylidenyl, and $C_{3-6}$ heterocycloalkylidenyl, wherein each of the alkylidenyl, heteroalkylidenyl, cycloalkylidenyl, and heterocycloalkylidenyl is optionally substituted with one or more substituents independently selected from $C_{1-4}$ alkyl, haloalkyl, $C_{1-4}$ alkoxy, amino, alkylamino, dialkylamino, oxo groups;
$R_{50}$-$R_{54}$, $R_{60}$-$R_{64}$ are independently a monovalent group selected from H, $C_{1-6}$ alkyl, $C_{1-6}$ heteroalkyl, $C_{3-6}$ cycloalkyl, and $C_{3-6}$ heterocycloalkyl, wherein each of the alkyl, heteroalkyl, cycloalkyl, and heterocycloalkyl is optionally substituted with one or more substituents independently selected from $C_{1-4}$ alkyl, haloalkyl, $C_{1-4}$ alkoxy, amino, $C_{1-4}$ alkylamino, $C_{1-4}$ dialkylamino, or a oxo group.

In some embodiments, the head group of the multivalent cationic lipids herein described can have a formula (XV):

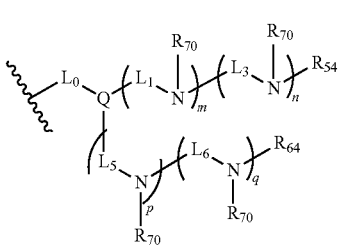

(Formula XV)

Q in Formula XV is N or CH;
m, n, p and q are independently 0-3 and m+n+p+q is equal or greater than 1;
$L_0$-$L_8$ are independently a divalent group selected from $C_{1-6}$ alkylidenyl, $C_{1-6}$ heteroalkylidenyl, $C_{3-6}$ cycloalkylidenyl, and $C_{3-6}$ heterocycloalkylidenyl, wherein each of the alkylidenyl, heteroalkylidenyl, cycloalkylidenyl, and heterocycloalkylidenyl is optionally substituted with one or more substituents independently selected from $C_{1-4}$ alkyl, haloalkyl, $C_{1-4}$ alkoxy, amino, alkylamino, dialkylamino, oxo groups;
$R_{54}$, $R_{64}$ and $R_{70}$ are independently a monovalent group selected from H, $C_{1-6}$ alkyl, $C_{1-6}$ heteroalkyl, $C_{3-6}$ cycloalkyl, and $C_{3-6}$ heterocycloalkyl, wherein each of the alkyl, heteroalkyl, cycloalkyl, and heterocycloalkyl is optionally substituted with one or more substituents independently selected from $C_{1-4}$ alkyl, haloalkyl, $C_{1-4}$ alkoxy, amino, $C_{1-4}$ alkylamino, $C_{1-4}$ dialkylamino, or a oxo group.

In some embodiments, the multivalent cationic lipids herein described comprise lipids of formula (XVI):

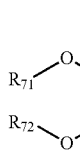

Formula (XVI)

wherein $R_{71}$ and $R_{72}$ are independently $C_6$ to $_{18}$ alkyl or alkenyl group and A is a moiety of Formula (III) or Formula (IV).

In some particular embodiments, the multivalent cationic lipids herein described comprise lipids of MVL5 of formula (XVII):

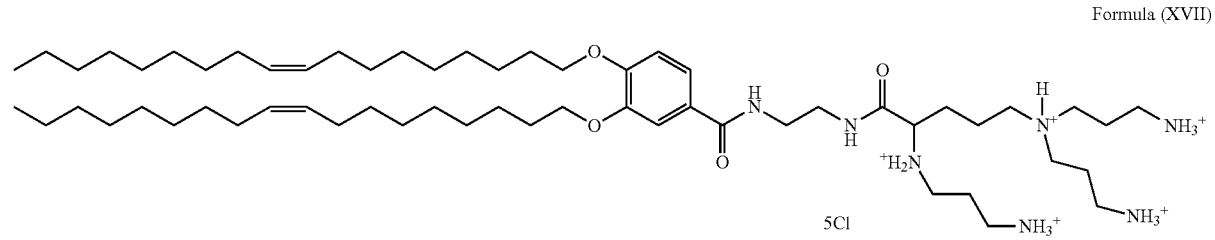 [SMILES: CCCCCCCC/C=C\CCCCCCCCOc1ccc(C(=O)NCCNC(=O)C(CCC[NH+](CCC[NH3+])CCC[NH3+])[NH2+]CCC[NH3+])cc1OCCCCCCCC/C=C\CCCCCCCC]

Formula (XVII)

In some embodiments herein described, the multivalent cationic lipids can have a highly charged dendritic head group wherein the dendritic head group comprises repetitive branch units each branch unit bearing at least one positively charged group. For example, the multivalent cationic lipids can comprise lipids of MVLBG2.

In some embodiments, the multivalent cationic lipids herein described comprise lipids of Formula (XVIII)

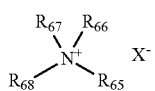

Formula (XVIII)

wherein
$R_{65}$ and $R_{66}$ are independently $C_1$ to $_4$ alkyl or alkenyl group;
$R_{67}$ and $R_{68}$ are independently $C_8$ to $_{19}$ alkyl or alkenyl group; and
X is an ion including $F^-$, $Cl^-$, $Br^-$, $NO_3^-$, and $ClO_4^-$.

In embodiments herein described, cationic NLPs comprise a scaffold protein and a lipid component comprising cationic lipids and membrane forming lipids in ratios and proportions that would be identifiable by a skilled person upon reading of the present disclosure.

In some embodiments, cationic NLPs herein described have a lipid component to scaffold molar ratio ranging from 20:1 to 240:1, preferably from 40:1 to 240:1, depending on the scaffold protein and the lipid component used as will be understood by a skilled person. Within the lipid component of the NLPs, the cationic lipids are comprised in about 1%-60% (±0.5, preferably from 5% to 40% (±0.5%, of the total lipids in the lipid component including the cationic lipids and the membrane forming lipids.

In some particular embodiments, the cationic NLPs herein described have apoE422k or apoA1 as scaffold protein and DMPC, POPC, DOPC as the membrane forming lipid. In cases when DMPC is used as the membrane forming lipids, cationic lipids such as DC-cholesterol, DDAB, DMEPC, DMTAP, DOEPC, DOTAP and MVL5 are in a percentage from 1% up to 40% of the lipid component (see FIG. 6 and Example 2), preferably with DMEPC, DDAB and DMTAP at a percentage from 1% to 20%. In cases when POPC or DOPC is used as the membrane forming lipids, cationic lipids such as DC-cholesterol, DDAB, DMEPC, DMTAP, DOEPC, DOTAP and MVL5 are in a percentage from 1% up to 30% of the lipid component.

In some embodiments, cationic NLPs herein described have a lipid component comprising membrane forming lipids in an amount from 99 to 40 mol % of the lipid component and the cationic lipids in an amount from 1 to 60 mol % of the lipid component. In some particular embodiments, the lipid component comprises membrane forming lipids in an amount from 95 to 60 mol % of the lipid component and the cationic lipids in an amount from 5 to 40 mol % of the lipid component.

In preferred embodiments, the NPLs herein described can have a membrane forming lipid: cationic lipid: scaffold protein ratio range between 19:1:1 and 96:144:1, preferably 136:34:1, with exact molar ratios depending on the optimal lipid:protein ratio for that lipid mixture and scaffold protein identifiable by a skilled person upon reading of the present disclosure.

In some embodiments, the cationic lipids are comprised within an NLP herein described in a molar lipid concentration about 1-60% (±0.5%, preferably about 5-20% (±0.5%. In some embodiments, the cationic lipids can be comprised within an NLP herein described in an amount of 20% of the total lipid content of the NLP and the membrane forming lipids can be comprised within an NLP herein described in an amount of 80% of the total lipid content.

In some embodiments, cationic-NLP herein described can be provided with a concentration of monovalent and/or multivalent cationic lipid selected based on valency of the cationic lipid so that the greater the multivalency, the lower the overall lipid % in the NLP. In particular, in some embodiments, the cationic-NLPs can comprise cationic lipids in concentrations of 1% to 5% such as 1%, 2%, or 5% of multivalent cationic lipids (such as MVL5) with 99, 98, or 95% of membrane forming lipids (such as DMPC). In some embodiments, the cationic-NLPs can comprise cationic lipids in concentrations of at least 5% such as 5%, 10%, and 20% of monovalent cationic lipids (such as DDAB) with 95, 90, or 80% of membrane forming lipids (such as DMPC).

In some embodiments, the membrane forming lipids component of the lipid component lipids such as phospholipids, preferably including at least one phospholipid, typically soy phosphatidylcholine, egg phosphatidylcholine, soy phosphatidylglycerol, egg phosphatidylglycerol, palmitoyl-oleoyl-phosphatidylcholine distearoylphosphatidylcholine, or distearoylphosphatidylglycerol. Other useful phospholipids include, e.g., phosphatidylcholine, phosphatidylglycerol, sphingomyelin, phosphatidylserine, phosphatidic acid, phosphatidylethanolamine, lysolecithin, lysophosphatidylethanolamine, phosphatidylinositol, cephalin, cardiolipin, cerebrosides, dicetylphosphate, dioleoylphosphatidyl choline, dipalmitoylphosphatidylcholine, dipalmitoylphosphatidylglycerol, dioleoylphosphatidylglycerol, stearoyl-palmitoyl-phosphatidylcholine, di-palmitoyl-phosphatidylethanolamine, distearoyl-phosphatidylethanolamine, di-myrstoyl-phosphatidylserine, and dioleyl-phosphatidylcholine.

Additionally exemplary membrane forming lipids that can be comprised in various combinations together with one or more lysolipids comprise 1,2-dipalmitoyl-sn-glycero-3-phosphocholine, 1,2-dimyristoyl-sn-glycero-3-phosphocholine, 1,2-dilauroyl-sn-glycero-3-phosphocholine, 1,2-didecanoyl-sn-glycero-3-phosphocholine, 1,2-dierucoyl-sn-glycero-3-phosphocholine, 1,2-dioleoyl-sn-glycero-3-phosphocholine, 1,2-dipalmitoleoyl-sn-glycero-3-phosphocholine, 1,2-dimyristoleoyl-sn-glycero-3-phosphocholine, 1-stearoyl-2-oleoyl-sn-glycero-3-phosphocholine, 1-stearoyl-2-myristoyl-sn-glycero-3-phosphocholine, 1-palmitoyl-2-oleoyl-sn-glycero-3-phosphocholine, egg phosphatidylcholine extracts, soy phosphatidylcholine extracts, heart phosphatidylcholine extracts, brain phosphatidylcholine extracts, liver phosphatidylcholine extracts, 1,2-distearoyl-sn-glycero-3-phosphate, 1,2-dipalmitoyl-sn-glycero-3-phosphate, 1,2-dimyristoyl-sn-glycero-3-phosphate, 1,2-dilauroyl-sn-glycero-3-phosphate, 1-palmitoyl-2-oleoyl-sn-glycero-3-phosphate, 1-stearoyl-2-oleoyl-sn-glycero-3-phosphate, 1,2-dipalmitoyl-sn-glycero-3-phosphoethanolamine, 1,2-dimyristoyl-sn-glycero-3-phosphoethanolamine, 1,2-dilauroyl-sn-glycero-3-phosphoethanolamine, 1,2-dioleoyl-sn-glycero-3-phosphoethanolamine, 1,2-dipalmitoleoyl-sn-glycero-3-phosphoethanolamine, Egg phosphatidylethanolamine extract, soy phosphatidylethanolamine extract, heart phosphatidylethanolamine extract, brain phosphatidylethanolamine extract, 1,2-distearoyl-sn-glycero-3-phospho-(1'-rac-glycerol), 1,2-dioleoyl-sn-glycero-3-phospho-(1'-rac-glycerol), 1,2-dipalmitoyl-sn-glycero-3-phospho-(1'-rac-glycerol), 1,2-dimyristoyl-sn-glycero-3-phospho-(1'-rac-glycerol), 1,2-dilauroyl-sn-glycero-3-phospho-(1'-rac-glycerol), 1-palmitoyl-2-oleoyl-sn-glycero-3-phospho-(1'-rac-glycerol), egg phosphatidylglycerol extract, soy phosphatidylglycerol extract, 1,2-distearoyl-sn-glycero-3-phospho-L-serine, 1,2-dioleoyl-sn-glycero-3-phospho-L-serine, 1,2-dipalmitoyl-sn-glycero-3-phospho-L-serine, 1,2-dimyristoyl-sn-glycero-3-phospho-L-serine, 1,2-dilauroyl-sn-glycero-3-phospho-L-serine, 1-palmitoyl-2-oleoyl-sn-glycero-3-phospho-L-serine, soy phosphatidylserine extract, brain phosphatidylserine extract, 2-((2,3-bis(oleoyloxy)propyl)dimethylammonio)ethyl hydrogen phosphate, cholesterol, ergosterol, sphingolipids, ceramides, sphingomyelin, gangliosides, glycosphingolipids, 1,2-dioleoyl-3-trimethyl-ammonium-propane, 1,2-di-O-octadecenyl-3-trimethylammonium propane.

In some embodiments, non-phosphorus containing lipids can also be used as membrane forming lipids in the NLPs herein described, e.g. stearylamine, docecylamine, acetyl palmitate, and fatty acid amides. Additional membrane forming lipids suitable for use in providing NLPs are well known to persons of ordinary skill in the art and are cited in a variety of well-known sources, e.g., McCutcheon's Detergents and Emulsifiers and McCutcheon's Functional Materials, Allured Publishing Co., Ridgewood, N.J., both of which are incorporated herein by reference.

In some embodiments, the cationic lipid component comprises lipids such as DC-cholesterol (3β-[N-(N',N'-dimethylaminoethane)-carbamoyl]cholesterol hydrochloride), DDAB (dimethyldioctadecylammonium (Bromide Salt)), DMEPC (1,2-dimyristoleoyl-sn-glycero-3-ethylphosphocholine), DOEPC (1,2-dioleoyl-sn-glycero-3-ethylphosphocholine) (the EPC family further includes 16:0-18:1, 18:0, 16:0, 14:0, 12:0 variants), DMTAP (1,2-dimyristoyl-3-trimethyl ammonium-propane), DOTAP (1,2-dioleoyl-3-trimethylammonium-propane) (the TAP family further includes 18:0, 16:0, 14:0 variants), MVL5 (N1-[2-((1S)-1-[(3-aminopropyl)amino]-4-[di(3-amino-propyl)amino]butylcarboxamido)ethyl]-3,4-di[oleyloxy]-benzamide), DODAP (1,2-dioleoyl-3-dimethylammonium-propane), DMDAP (1,2-dimyristoyl-3-dimethylammonium-propane), DPDAP (1,2-dipalmitoyl-3-dimethylammonium-propane), DSDAP (1,2-distearoyl-3-dimethylammonium-propane), DOTMA (1,2-di-O-octadecenyl-3-trimethylammonium propane), and others identifiable by a person of ordinary skill in the art. Additional cationic lipids are commercially available or identifiable by a skilled person upon reading of the present disclosure (Semple C. S. et. al., Nature Biotechnology, 2010, Vol. 28:172-178).

In some embodiments various combinations and ratios of membrane forming lipids and cationic lipids can be comprised within a cationic NLP herein described, such as DMPC and DMTAP at cationic lipid ratio range of 1 to 40, DMPC and DOTAP at cationic lipid ratio range of 1 to 20, DMPC and DC-cholesterol at cationic lipid ratio range of 1 to 40, DMPC and DDAB at cationic lipid ratio range of 1 to 20, DMPC and DMEPC at cationic lipid ratio range of 1 to 40, DMPC and DODAP at cationic lipid ratio range of 1 to 40, DMPC and DOEPC at cationic lipid ratio range of 1 to 30, DMPC and DOTMA at cationic lipid ratio range of 1 to 20, DMPC and MVL5 at cationic lipid ratio range of 0.2 to 20. In some embodiments, the total amount of cationic lipids is less than 60% of the total amount of lipids used in the NLPs.

The above ratio between membrane forming lipid DMPC and various cationic can be derived for other membrane forming lipids such as DOPC, POPC, DOPE, DPPC and natural lipids extracts such as SoyPC and EggPC and a mixture thereof as will be understood for a skilled person, and cationic lipid ratios can range from 0.2 to 60 with a total cationic lipid which in some instances can amount to less than 60% of the total lipid of the cationic-NLPs herein described In some embodiments, the scaffold proteins can contain amino acid additions, deletions, or substitutions. In other embodiments, the scaffold proteins can be derived from various species and more particularly derived from human, mouse, rat, guinea pig, rabbit, cow, horse, pig, dog, and non-human primates.

In some embodiments various combinations of membrane forming lipids and cationic lipids in accordance with the disclosure can be comprised within an NLP stabilized by scaffold proteins such as human derived apoE4, truncated versions of human derived apoE4 (e.g. apoE422k), human derived apoE3, truncated versions of human derived apoE3 (e.g. apoE322k), human derived apoE2, truncated versions of human derived apoE2 (e.g. apoE222k), human derived apoA1, truncated versions of human derived apoA1 (e.g. Δ49ApoA1, MSP1, MSP1T2, MSP1E3D1), mouse derived apoE4, truncated versions of mouse derived apoE4 (e.g. apoE422k), mouse derived apoE3, truncated versions of mouse derived apoE3 (e.g. apoE322k), mouse derived apoE2, truncated versions of mouse derived apoE2 (e.g. apoE222k), mouse derived apoA1, truncated versions of mouse derived apoA1 (e.g. Δ49ApoA1, MSP1, MSP1T2, MSP1E3D1), rat derived apoE4, truncated versions of rat derived apoE4 (e.g. apoE422k), rat derived apoE3, truncated versions of rat derived apoE3 (e.g. apoE322k), rat derived apoE2, truncated versions of rat derived apoE2 (e.g. apoE222k), rat derived apoA1, truncated versions of rat derived apoA1 (e.g. Δ49ApoA1, MSP1, MSP1T2, MSP1E3D1), lipophorins (e.g. *B. mori, M. sexta*), synthetic linear or cyclic peptides that mimic the function of apolipoproteins. Other apolipoproteins, as will be understood for a skilled person, can be used to form NLP, including but not limited to apoB and apoC.

In some embodiments, the scaffold protein is formed by amphipathic peptides and/or synthetic apolipoproteins which are configured to maintain an amphipathic structure and capability of self-assembly. In particular, in those embodiments, the peptides and/or synthetic apolipoprotein are configured and selected to provide a plurality of helical segments each having a primary structure configured to form an alpha helix secondary structure. In the alpha helix secondary structure of at least one helical segment, the peptides and/or synthetic apolipoprotein comprise a plurality of hydrophobic amino acids and a plurality of hydrophilic amino acids positioned in the primary structure to provide an amphipathic alpha helix secondary structure, with the plurality of hydrophobic amino acids forming an hydrophobic amino acid cluster and the plurality hydrophilic amino acids forming an hydrophilic amino acid cluster. In some of those embodiments, the scaffold proteins can be peptides derived from apolipoproteins, and can contain amino acid additions, deletions, or substitutions. In other embodiments, these peptides have no sequence homology to apolipoproteins but can be structural analogs. In some embodiments, the peptides can be prepared with L- or D-amino acids. In embodiments where the scaffold protein comprises one or more peptides the skilled person would be able to identify the ratios of peptides based on the length and number of peptides and apolipoproteins and on a desired dimension of the nanolipoprotein particles upon reading of the present disclosure. Additional description of scaffold proteins can be found in PCT/US2015/051172 published on Mar. 16, 2017 as WO2017/044899 incorporated herein by reference in its entirety.

In some embodiments various combinations of membrane forming lipids and cationic lipids in accordance with the disclosure can be comprised within an NLP stabilized by different scaffold proteins, DMPC and DMTAP (ratio range of 1 to 40×) with human derived apoE422k (lipid:scaffold protein range 40:1 to 200:1), DMPC and DOTAP (ratio range of 1× to 20×) with human derived apoE422k (lipid:scaffold protein range 40:1 to 200:1), DMPC and DC-cholesterol (ratio range of 1× to 40×) with human derived apoE422k (lipid:scaffold protein range 40:1 to 200:1), DMPC and DDAB (ratio range of 1× to 20×) with human derived apoE422k (lipid:scaffold protein range 40:1 to 200:1), DMPC and DMEPC (ratio range of 1× to 40×) with human derived apoE422k (lipid:scaffold protein range 40:1 to 200:1), DMPC and DODAP (ratio range of 1× to 40×) with human derived apoE422k (lipid:scaffold protein range 40:1 to 200:1), DMPC and DOEPC (ratio range of 1× to 30×) with human derived apoE422k (lipid:scaffold protein range 40:1 to 200:1), DMPC and DOPE (ratio range of 1× to 40×) with human derived apoE422k (lipid:scaffold protein range 40:1 to 200:1), DMPC and DOTMA (ratio range of 1× to 20×) with human derived apoE422k (lipid:scaffold protein range 40:1 to 200:1), DMPC and MVL5 (ratio range of 0.2× to 20×) with human derived apoE422k (lipid:scaffold protein range 40:1 to 200:1).

The above ratios between membrane forming lipid DMPC, various cationic lipids, and human derived apoE422k can be derived for other membrane forming lipids such as DOPC, POPC, DOPE, DPPC and natural lipids extracts such as SoyPC and EggPC and a mixture thereof as will be understood for a skilled person upon the reading of the present disclosure. [1]

The above ratios between lipids (membrane forming and various cationic lipids) and apoE-derived scaffold proteins can be derived for other membrane forming lipids such as DOPC, POPC, DOPE, DPPC and natural lipids extracts such as SoyPC and EggPC and a mixture thereof as will be understood for a skilled person, and can range from 40:1 to 240:1.

In some embodiments, the ratios between lipids (membrane forming and various cationic lipids) and apoA-derived scaffold proteins can be derived for other membrane forming lipids such as DOPC, DMPC, POPC, DOPE, DPPC and natural lipids extracts such as SoyPC and EggPC and a mixture thereof as will be understood for a skilled person, and can range from 20:1 to 180:1.

In some preferred embodiments, the cationic NPLs herein described have apoE422k as the scaffold protein, DMPC as membrane forming lipids and DDAB as the cationic lipid in a molar ratio from 5 to 20. In some preferred embodiments, the cationic NPLs herein described have apoE422k as the scaffold protein, DMPC as membrane forming lipids and DMTAP as the cationic lipid in a molar ratio from 10 to 30.

In other preferred embodiments, the cationic NPLs herein described have apoE422k as the scaffold protein, DMPC as membrane forming lipids and MVL5 as the cationic lipid in a molar ratio from 1 to 10. In other preferred embodiments, the cationic NPLs herein described have apoE422k as the scaffold protein, DMPC as membrane forming lipids and DMEPC as the cationic lipid in a molar ratio from 2 to 20. In other preferred embodiments, the cationic NPLs herein described have apoE422k as the scaffold protein, DMPC as membrane forming lipids and DODAP as the cationic lipid in a molar ratio from 20 to 40.

In some preferred embodiments, the cationic NPLs herein described have apoE422k as the scaffold protein, POPC as membrane forming lipids and DOTAP as the cationic lipid in a molar ratio from 1 to 10. In some preferred embodiments, the cationic NPLs herein described have apoE422k as the scaffold protein, POPC as membrane forming lipids and DMTAP as the cationic lipid in a molar ratio from 1 to 10. In some preferred embodiments, the cationic NPLs herein described have apoE422k as the scaffold protein, POPC as membrane forming lipids and DMEPC as the cationic lipid in a molar ratio from 1 to 10. In some preferred embodiments, the cationic NPLs herein described have apoE422k as the scaffold protein, POPC as membrane forming lipids and DC-cholesterol as the cationic lipid in a molar ratio from 1 to 10. In some preferred embodiments, the cationic NPLs herein described have apoE422k as the scaffold protein, POPC as membrane forming lipids and DOEPC as the cationic lipid in a molar ratio from 1 to 10. In some preferred embodiments, the cationic NPLs herein described have apoE422k as the scaffold protein, POPC as membrane forming lipids and DDAB as the cationic lipid in a molar ratio from 1 to 10.

In some preferred embodiments, the cationic NPLs herein described have apoE422k as the scaffold protein, DOPC as membrane forming lipids and DMTAP as the cationic lipid in a molar ratio from 1 to 10. In some preferred embodiments, the cationic NPLs herein described have apoE422k as the scaffold protein, DOPC as membrane forming lipids and DMEPC as the cationic lipid in a molar ratio from 1 to 10. In some preferred embodiments, the cationic NPLs herein described have apoE422k as the scaffold protein, DOPC as membrane forming lipids and DC-cholesterol as the cationic lipid in a molar ratio from 1 to 10. In some preferred embodiments, the cationic NPLs herein described have apoE422k as the scaffold protein, DOPC as membrane forming lipids and DOTAP as the cationic lipid in a molar ratio from 1 to 10. In some preferred embodiments, the cationic NPLs herein described have apoE422k as the scaffold protein, DOPC as membrane forming lipids and DOEPC as the cationic lipid in a molar ratio from 1 to 10. DOPC as membrane forming lipids and DDAB as the cationic lipid in a molar ratio from 1 to 10.

In some preferred embodiments, the cationic NPLs herein described have apoA1 as the scaffold protein, DMPC as membrane forming lipids and DDAB as the cationic lipid in a molar ratio from 5 to 20. In some preferred embodiments, the cationic NPLs herein described have apoA1 as the scaffold protein, DMPC as membrane forming lipids and DMTAP as the cationic lipid in a molar ratio from 10 to 30. In other preferred embodiments, the cationic NPLs herein described have apoA1 as the scaffold protein, DMPC as membrane forming lipids and MVL5 as the cationic lipid in a molar ratio from 5 to 20. In other preferred embodiments, the cationic NPLs herein described have apoA1 as the scaffold protein, DMPC as membrane forming lipids and DMEPC as the cationic lipid in a molar ratio from 20 to 40. In other preferred embodiments, the cationic NPLs herein described have apoA1 as the scaffold protein, DMPC as membrane forming lipids and DOTMA as the cationic lipid in a molar ratio from 5 to 20.

In some embodiments, the cationic NLPs herein described can comprise a mixture of cationic lipids at ratios and concentrations identifiable by a skilled person upon reading of the present disclosure. For example, in at least one embodiment, cationic NLPs herein described can comprise DMPC:MVL5:DODAP at ratios 3:1:1 with ApoE scaffold protein. In at least one embodiment, cationic NLPs herein described can comprise DMPC:MVL5:DODAP at ratios 2:1:2 with ApoE scaffold protein. In at least one embodiment, cationic NLPs herein described can comprise DMPC:MVL5:DODAP at ratios 3:1:1 and 20% GMO additive with ApoE scaffold protein. In another embodiment, cationic NLPs herein described can comprise DMPC:DDAB:DOPE at ratios 70:10:20.

In embodiments, herein described cationic NLPs can be prepared with various methods resulting in the assembly of the lipid component formed by the membrane forming lipid and the cationic lipids with the scaffold protein.

In particular, in some embodiments the cationic NLP lipid component and scaffold protein component can be contacted to form an admixture for a time and under conditions allowing assembling of the NLP according to methods known or identifiable by a skilled person upon reading of the present disclosure.

For example, in some embodiments, cationic NLPs herein described can be assembled by a dialysis method, which is a self-assembly process involving detergent solubilization of lipids followed by detergent removal as described for example in [2-4] A dialysis method typically involves solubilizing the membrane lipid component in a detergent, such as sodium cholate, at detergent concentrations above the critical micelle concentration. The resulting lipid/detergent solution is then incubated to allow for dissolution of the scaffold protein and sufficient interaction between the scaffold protein and lipid mixture (e.g. for about 30 min ±5 min). After the incubation period, the detergent is removed (e.g. through dialysis or rinsing with detergent binding beads). The appropriate lipid to apolipoprotein ratio that will allow for self-assembly will be understood by a skilled person upon reading of the present disclosure. In particular, the NLP typically self-assemble during the detergent removal process.

For example, in some embodiments, NLPs herein described can be assembled following a detergent-binding bead method, which is a self-assembly process involving detergent solubilization of lipids followed by detergent removal. This method typically involves solubilizing the membrane lipid component in a detergent, such as sodium cholate, at detergent concentrations above the critical micelle concentration. The resulting lipid/detergent solution is then incubated to allow for dissolution of the scaffold protein and sufficient interaction between the scaffold protein and lipid mixture (e.g. for about 30 min—with the term about indicating the time ±5 min). After the incubation period, the detergent is removed by incubating with detergent binding beads. The appropriate lipid to apolipoprotein ratio that will allow for self-assembly will be understood by a skilled person upon reading of the present disclosure. In particular, the NLPs typically self-assemble during the detergent removal process. An example of a detergent commonly used to prepared apolipoprotein-lipid complexes is sodium cholate.

In some embodiments, NLPs herein described can be assembled by temperature cycling method, where an admixture of lipid component and scaffold protein component forming the NLPs is subjected to a temperature transition cycle in presence of a detergent such as the one described in [5-7] In the temperature cycle, the temperature of the admixture is raised above and below the gel crystalline transition temperature of the membrane forming lipids. In particular, in accordance with an exemplary procedure the lipid component including membrane forming lipid and cationic lipids can be added to the scaffold protein at the desired lipid to scaffold protein ratio in buffer. After thoroughly mixing the components, the solution is incubated a particular temperature for a certain amount of time. For example, the solution can be maintained at 23.8° C. for at least 2 hours (see Example 3).

In some embodiments, NLPs herein described can be assembled by an in vitro coupled transcription and translation method, where self-assembly of the NLPs can be achieved while the apolipoprotein or other scaffold protein is being translated from mRNA as described for example in [8-11]. In this process, expression system lysates are mixed with the lipid component of the NLP and plasmid DNA encoding the scaffold protein. The reaction can then be allowed to proceed until assembly occurs during apolipoprotein expression (e.g. for approximately 4-24 hrs). The apolipoprotein typically contains an affinity tag (e.g. His-tag) for subsequent purification of the self-assembled NLP from the lysate.

In general, assembly of cationic NLPs can be accomplished with a wide range of ratios of total lipids to scaffold proteins. Cationic NLPs with lipid to scaffold molar ratios of about 20:1 up to about 240:1 can be synthesized. A typical assembly with apoA1 scaffold protein uses a lipid to protein molar ratio of about 80:1 and a typical assembly with apoE uses a lipid to protein molar ratio of about 170:1 wherein the term about when referred to ratios indicates that the ratio can be ±5%.

In some embodiments, the methods and systems herein described are performed at predefined lipid protein ratio, assembly conditions and/or with the use of preselected protein component and lipid component so as to increase the yield, control the size and composition of the resulting NLP, provide an NLP of pre-determined dimensions, achieve desired functionality of the NLP, such as a certain level of loading capacity for a target drug molecule. In some embodiments, the molar ratio of lipid component to scaffold protein component is 20:1, 30:1, 40:1, 50:1, 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, and 240:1. In NLPs herein described, the lipid to scaffold protein component ratio can be determined on a case by case basis in view of the experimental design as will be understood by a skilled person.

Composition of an NLP can be detected by various techniques known in the art, such as high performance liquid chromatography (HPLC), reverse phase high performance liquid chromatography (RP-HPLC), mass spectrometry, thin layer chromatography, NMR spectroscopy and elemental analysis could be used to define the composition of the particles and additional techniques identifiable by a skilled person.

In several embodiments herein described, cationic NLPs show different size, compositions, and homogeneity (see Examples 1-2). Size and compositions of the resulting NLPs can be characterized by SEC (size exclusion chromatography) traces which are used to separate out molecules in solution by their size and in some cases their molecular weights as will be understood by a skilled person.

Figure 7:
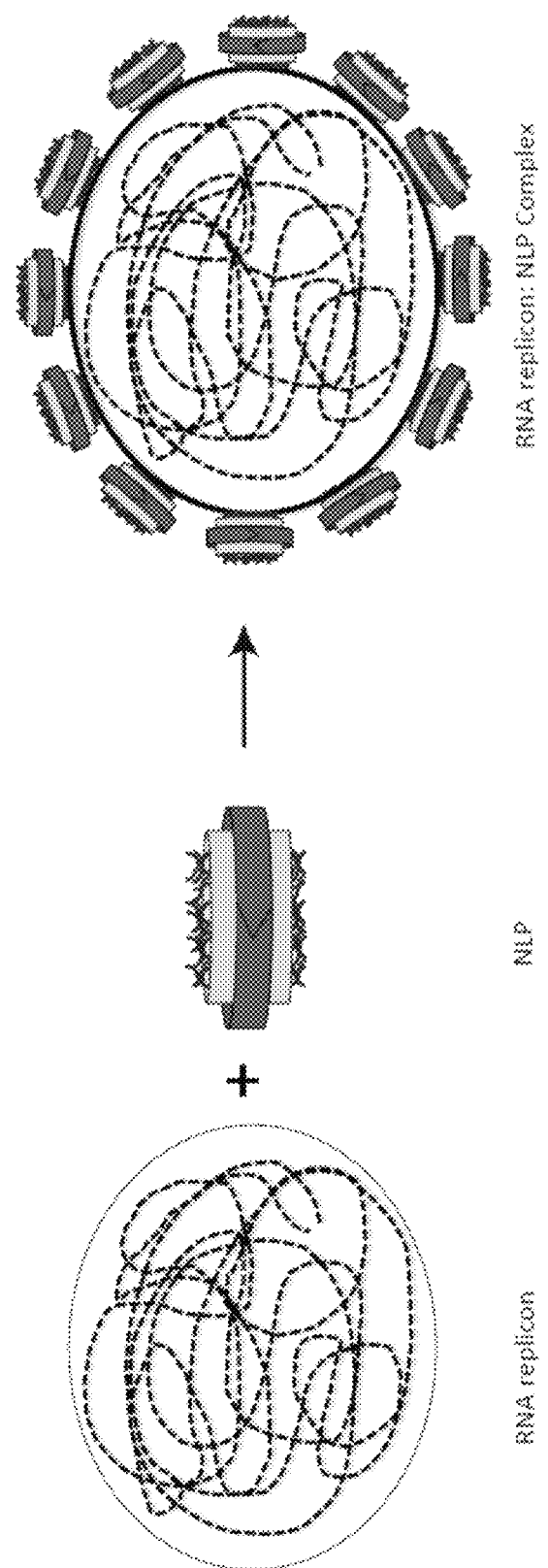
FIG. 7 shows an exemplary illustration of the formation of cationic-NLP:Replicon complexes. NLPs are mixed with RNA Replicon at various NLP:RNA molar ratios. After simple mixing, the cationic lipids within the NLPs are attracted to the negatively charged RNA. Each RNA molecule binds to multiple NLPs to form a NLP:Replicon complex.

In embodiments herein described, NLPs comprising cationic lipids and optionally additional components such as polymerizable lipids, amphipathic compounds and/or target proteins and assembled as herein described, are then contacted with nucleic acids to form cationic NLPs-RNA complex which allow highly efficient in vivo delivery of the nucleic acids (see FIG. 7). Methods to include polymerizable lipids, target proteins and/or functionalized membrane forming lipids are described for example in U.S. Patent Publication No. 2009/0192299, U.S. Patent Publication No. 2009/0136937 and U.S. Pat. No. 8,883,729 issued on Nov. 11, 2014 and in U.S. Pat. No. 8,889,623 issued on Nov. 18, 2014 the content of each of which is incorporated by reference in its entirety in the present disclosure.

In some embodiments herein described cationic—NLPs can be used to form complex with one or more polynucleotides.

The term "polynucleotide" or "polynucleotide molecule" as used herein indicates an organic polymer composed of two or more monomers including nucleotides, or analogs thereof. The isoelectric point of a polynucleotide in the sense of the disclosure is less than 7 as will be understood by a skilled person. The term "nucleotide" refers to any of several compounds that consist of a ribose or deoxyribose sugar joined to a purine or pyrimidine base and to a phosphate group and that is the basic structural unit of nucleic acids. The term "nucleotide analog" refers to a nucleotide in which one or more individual atoms have been replaced with a different atom or with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide." In particular polynucleotides in the sense of the disclosure comprise biological molecules comprising a plurality of nucleotides. Exemplary nucleic acids include deoxyribonucleic acids, ribonucleic acids, and synthetic analogues thereof, including peptide nucleic acids. Polynucleotides can typically be provided in single-stranded form or double-stranded form and in liner or circular form as will be understood by a person of ordinary skill in the art.

In the embodiments herein described, the nucleic acids that can be incorporated into the cationic NLPs include RNA, DNA, or synthetic variants that carry an overall negative charge. More specifically, the cationic NLPs can form a complex with large double-stranded DNA, such as plasmids, short double stranded DNA, short single stranded DNA, such as DNA aptamers, short single-stranded RNA, such as microRNA, short double-stranded RNA such as siRNA, adjuvant molecules such as polyI:C, long single-stranded RNA such as messenger RNA, and replicon RNA.

In some embodiments, the nucleic acids are molecules having a number of bases up to 200 bases, up to 5000 bases up to 15,000 bases, preferably from 200 to 15,000 bases, more preferably from 5,000 to 15,000 bases. In some particular embodiments, the nucleic acids herein described comprise a special type of self-amplifying RNA molecules termed replicons, which are based on alphavirus genomic RNA.

The term "alphavirus" describes enveloped single-stranded positive sense RNA viruses of the family Togaviridae. The genus alphavirus contains approximately 30 members, which can infect humans as well as other animals. Alphavirus particles typically have a 70 nm diameter, tend to be spherical or slightly pleomorphic, and have a 40 nm isometric nucleocapsid. The total genome length of alphaviruses ranges between 11,000 and 12,000 nucleotides, and has a 5'cap and 3' poly-A tail. There are two open reading frames (ORF's) in the genome, non-structural (ns) and structural. The ns ORF encodes proteins (nsP1-nsP4) necessary for transcription and replication of viral RNA. The structural ORF encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion. The four ns protein genes are encoded by genes in the 5' two-thirds of the genome, while the three structural proteins are translated from a subgenomic mRNA colinear with the 3' one-third of the genome.

Alphaviruses can be used in gene therapy and vaccine development. Alphaviruses offers several advantages over DNA vectors in gene therapy. For example, vaccines based on DNA plasmids often contain regulatory sequences and antibiotic resistance genes. The potential integration of such sequences into the host genome by non-homologous recombination may represent an unknown risk. In contrast, replication/transcription of replicons is strictly confined to the host cell cytosol, and does not require any cDNA intermediates, nor is any recombination with or integration into the chromosomal DNA of the host required. Thus, several safety issues associated with DNA vaccines do not arise with RNA-based vaccines. Due to autonomous RNA replication, RNA replicons are also able to drive high level, cytosolic expression of recombinant antigens stimulating both the humoral and the cellular branch of the immune system.

The term "replicon" refers to a virus-based expression system based on replacement of viral structural genes by one or more genes of interest. These modified viral genomes can be synthesized in vitro and delivered into cells either by transfection or in infectious viral particles, which deliver essentially every packaged RNA molecule into the cells both in vivo and in vitro. The term replicon encompasses both DNA and RNA. Both positive- and negative-stranded viruses can be used to construct replicons and delivered as RNA, DNA, or viral replicon particles.

In some embodiments, the cationic NLPs-RNA complexes described herein comprise RNA replicons binding to a plurality of NLPs to form a cationic NLPs-replicon complex (see FIG. 7). RNA replicons herein described are derived from positive-strand RNA viruses, from which at least one gene encoding an essential structural protein has been deleted. RNA replicons can be regarded as disabled viruses unable to produce infectious progeny. Despite such gene deletions, the viral RNA can be replicated and transcribed by the viral RNA polymerase. The genetic information encoded by the replicon will be amplified many times, resulting in high levels of expression.

One or more target RNA molecules can be provided in NLPs according to methods comprising contacting the target RNA molecules with a plurality of cationic nanolipoprotein particles to provide one or more cationic-RNA nanolipoprotein particles, each comprising a target RNA molecule with its surface binding to a plurality of cationic NPLs as shown in FIG. 7. In particular, in some embodiments, to assemble cationic NLPs, a lipid mixture containing cationic lipids and membrane forming lipids can be prepared at the desired ratio. Cationic NLPs containing cationic lipids can be then prepared by using any of the methods described above that are intended for NLP assembly. Once the cationic NLPs are formed, the target RNA molecules (dissolved in a solvent) can then be added to the NLP solution and allowed to mix to allow binding of cationic NPLs (e.g. between 1 minute and 10 hours) to the outer surface of the target RNA molecule. Additional variations and embodiments of methods to incorporate a target RNA molecule in an NLP of the disclosure will be identifiable by a skilled person upon reading of the present disclosure.

In some embodiments, cationic nanolipoprotein particles when formulated with 1 μg RNA replicon demonstrated comparable transfection ability to 30 μg unformulated replicon through in vivo gene expression in mouse model.

In some embodiments, the cationic NLPs-RNA complex used to deliver the loaded RNA have a ratio of 0.05-0.2 between the number of nitrogen atoms in the cationic NLPs and the number of phosphate groups in the RNA, 10-fold lower compared to conventional approaches.

In some embodiments, cationic NLPs herein described can be used in biomedical applications, including gene therapy and vaccine and immunomodulation applications. In particular, cationic NLPs herein described can be used in nucleic acid delivery in order to achieve improved in vivo nucleic acid loading capacity and transfection efficiency. Nanoparticle-mediated RNA delivery performed with cationic NLPs herein described is expected to address several limitations of conventional gene therapy approaches due to their self-amplifying abilities, flexibility in constructing antigens with mutations, highly efficient protein synthesis, and enhanced immune protection from antigens. Additional features can also be implemented, such as adding adjuvants, functional polymers, and membrane-associated proteins for targeted in vivo delivery.

As used herein, "gene therapy" or "gene transfer" refers to the use of a nucleic acid as a drug, and to its delivery into a cell to treat a disease. Gene therapy aims to replace a faulty gene or to add a new gene in an attempt to treat a disease or to improve the subject's ability to fight against said disease. Gene therapy can be useful for treating a wide range of diseases such as genetic diseases and cancer.

According to the invention, the term "vaccine" relates to a pharmaceutical preparation (pharmaceutical composition) or product that upon administration induces an immune response. A vaccine may be used for the prevention or treatment of a disease.

The term "treatment" as used herein refers to both 1) therapeutic treatments or measures that cure, slow down, lessen symptoms of, and/or halt progression of a diagnosed pathologic conditions or disorder, and 2) and prophylactic/preventative measures. Those in need of treatment may include individuals already having a particular medical disorder as well as those who may ultimately acquire the disorder (i.e., those needing preventive measures).

In some embodiments, the cationic-NLP composition can be customized for desired nucleic acids loading capacity and stability by adjusting the molar ratio of the cationic NLPs and the nucleic acids of interest, the molar ratio of the total lipid component and the scaffold protein component, and the molar ratio of the cationic lipids and the membrane forming lipids.

In some embodiments, the cationic NLPs-RNA complex used for delivering nucleic acids have a lipid component to scaffold molar ratio ranging from 20:1 to 240:1, depending on the scaffold protein and the lipid component used as will be understood by a skilled person.

For example, in NLPs herein described having apoE4 and variants as scaffold protein and a lipid component comprising DMPC as the membrane forming lipid and DMTAP, the molar ratios of lipid component: scaffold protein component can range from 40:1 to 240:1, preferably from 100:1 to 240:1, even more preferably at 170:1. In NLPs herein described having apoA1 and variants as scaffold protein and a lipid component comprising DMPC as the membrane forming lipid and DMTAP, the molar ratios of lipid component: scaffold protein component can range from 40:1 to 240:1, preferably from 40:1 to 100:1, even more preferably at 80:1.

In some embodiments herein described, the cationic NLPs formed with apoA1 as the scaffold protein have a smaller diameter than those formed with apoE4 scaffold protein. For example, in one embodiment, the cationic NLP formed with apoA1 has a diameter of 13.6 nm, while the cationic NLP formed with apoE4 has a diameter of 17.6 nm. (Chromy, B. A. et al.) Different apolipoproteins impact nanolipoprotein particle formation. (*Journal of the American Chemical Society* 129, 14348-14354, doi:10.1021/ja074753y (2007)) (Fischer, N. O. et al.) Isolation, characterization, and stability of discretely-sized nanolipoprotein particles assembled with apolipophorin-III. *PloS one* 5, e11643, doi:10.1371/journal.pone.0011643 (2010).) In some embodiments, the cationic NLPs formed with apoA1 have a diameter in a range between 6 and 14 nm. The cationic NLPs formed with ApoE have a diameter in a range between 12 and 30 nm. In both types cationic NLPs, identical lipid components can be used.

In some embodiments, the cationic NLPs used for delivering nucleic acids have a lipid component comprising membrane forming lipids in an amount from 1 to 40 mol % of the lipid component and cationic lipids in an amount from 1 to 60 mol % of the lipid component, depending on the membrane forming lipids and cationic lipids as will be understood by a skilled person. In some embodiments, the NLP herein described comprise membrane forming lipid and cationic lipids in molar ratios ranging from 99:1 to 4:6.

For example, in cationic NLPs herein described having a lipid component comprising DMPC as the membrane forming lipid and DMTAP as cationic lipids, the DMPC can have a mol percentage ranging from 40 mol % to 99 mol %, preferably from 60 mol % to 95 mol % and DMTAP can have a mol percentage ranging from 1 mol % to 60 mol %, preferably from 5 mol % to 40 mol %. In some particular embodiments, DMTAP constitutes 20 mol % of the total lipid content. (see Examples 3-8).

In several embodiments cationic-NLPs herein described can form complexes with polynucleotides of various dimensions. In particular, a cationic-NLP-polynucleotide complex herein described comprises a polynucleotide molecule attached to one or more cationic NLPs each cationic NLP comprising one or more cationic lipids and a membrane forming lipid arranged in a discoidal membrane lipid bilayer stabilized by a scaffold protein.

In particular in some of those embodiments, a cationic-NLPs can comprise 1% to 5% multivalent cationic lipids forming complexes with polynucleotides up to 200 bases, from 200 to 5000 bases, at least 5,000 bases up to 15,000 bases in size in ratios cationic-NLPs:polynucleotide of 1:1 to 1:250 or higher.

In some embodiments, cationic-NLPs comprising monovalent and/or multivalent cationic lipids can form complexes with a polynucleotide of 201 to 15,000 bases in size in various ratios as will be understood by a skilled person upon reading of the present disclosure In some embodiments, the cationic NLPs are complexed with RNA and/or other polynucleotides in molar ratios from 10:1 to 500:1, preferably from 50:1 to 250:1, more preferably from 50:1 to 75:1. In particular, the cationic NLPs-polynucleotide complexes comprise membrane forming lipids, cationic lipids and RNA replicons in a molar ratio from 574:6:1 to 80,000:120,000:1, preferably from 3,960:40:1 to 12,000:18,000:1.

For example, in cationic NLPs-RNA complex herein described having a lipid component comprising DMPC as the membrane forming lipid and DMTAP as cationic lipids and RNA replicon. The molar ratio among DMPC, DMTAP and the RNA replicon ranges from 574:6:1 to 80,000:120,000:1, preferably from 3,960:40:1 to 12,000:18,000:1. In some preferred embodiments, the cationic NLPs-polyucleotide complex herein described comprise DMPC, DMTAP and RNA replicon at a molar ratio of 16,000:4,000:1. In some preferred embodiments, the cationic NLPs-RNA complex herein described comprise DMPC, DMTAP and RNA replicon at a molar ratio of 3,200:800:1.

In some embodiments, the cationic NLPs have a size 13-15 nm and the RNA replicon has a size of 50 nm and the cationic NLPs-RNA complex comprising both the cationic NLPs and the RNA replicon have a size ranging from 90 nm and 558 nm, depending on the type of scaffold proteins, membrane forming lipids, and cationic lipids used in the formation of the cationic NLPs (see FIG. 12).

The cationic NLPs-RNA complex described in several embodiments here demonstrate to stay stable when stored at 4° C. for over 50 days.

In embodiments herein described, the cationic NLPs-polynucleotide complex provide an efficient, versatile and reproducible delivery of RNA replicon molecules. In particular, the cationic NLP-replicon complex formulations are stable, easily prepared and do not fully encapsulate the replicon while capable of protecting against RNase degradation, shielding access to outside molecules as well as increasing the replicon's in vivo transfection efficiency (see Examples 6-8).

In some embodiments, the cationic NLPs-RNA complex used to deliver the loaded RNA have a ratio of 0.05-0.2 between the number of nitrogen atoms in the cationic NLPs and the number of phosphate groups in the RNA, 10-fold lower compared to conventional approaches. The cationic nanolipoprotein particles herein described in several embodiments when formulated with 1 µg RNA replicon demonstrated comparable transfection ability to 30 µg unformulated replicon through in vivo gene expression in mouse model.

In some embodiments, the RNA or other polynucleotide molecules are formulated at molar ratios ranging from 10 to 500 NLPs per RNA/polynucleotide molecule. In some embodiments, apoA1 NLPs are formulated with RNA/polynucleotide molecules (10,000-15,000 bases) at molar ratios ranging from 50 to 500 NLPs per RNA/polynucleotide molecules. In some preferred embodiments, apoA1 NLPs are formulated with RNA/polynucleotide molecules (10,000-15,000 bases) at molar ratios ranging from 50 to 150 NLPs per RNA molecules. In some embodiments, apoE NLPs are formulated with RNA molecules (10,000-15,000 bases) at molar ratios ranging from 10 to 100 NLPs per RNA molecules. In some preferred embodiments, apoE NLPs are formulated with RNA/polynucleotide molecules (10,000-15,000 bases) at molar ratios ranging from 10 to 25 NLPs per RNA/polynucleotide molecules.

In embodiments herein described, cationic-NLPs can form stable cationic-NLP:RNA complexes comprised of different lipids, various percentages of cationic lipid, and a range of ratios of cationic-NLP added per RNA complex.

In some embodiments, cationic-NLPs herein described can comprise membrane forming lipid of Formula (XII). In those embodiments, exemplified by the representative example of DMPC, the cationic-NLPs can comprise various percentages and cationic lipid components with the lipid of Formula XV being predominant. In some cases, stability and/or homogeneity of the NLPs prepared can be controlled by selecting the membrane forming lipid and/or scaffold protein used. In particular, the ratios between membrane forming lipids and cationic lipids can be selected on the types of membrane forming lipids and cationic lipids selected for the NLP assembly. In general, DMPC is configured to have more ordered lipid-lipid interactions compared to DOPC, resulting in tighter packing of the lipids in the bilayer. Consequently, more lipids are contained in a single NLP. Therefore more cationic lipids can be subsequently packed into a DMPC-based NLPs compared to DOPC-based NLPs. As a consequence, for example, a 5% of cationic lipid incorporation can result in more positive charges in a DMPC-based NLPs than a DOPC-based NLPs as there is a greater number of lipids in the DMPC-based NLP than in the DOPC-based NLP.

In some embodiments, the specific type of cationic lipid can be selected to control the binding ability of the resulting cationic-NLP RNA complex.

In some embodiments, the cationic lipid can be a cationic lipid of Formula XVI or XVII, in those embodiments, the resulting cationic-NLPs provides tight RNA binding at low cationic lipid percentages as compared to other types of cationic-NLP RNA complexes including cationic lipids such as the one with formula (XVIII).

Figure 10:
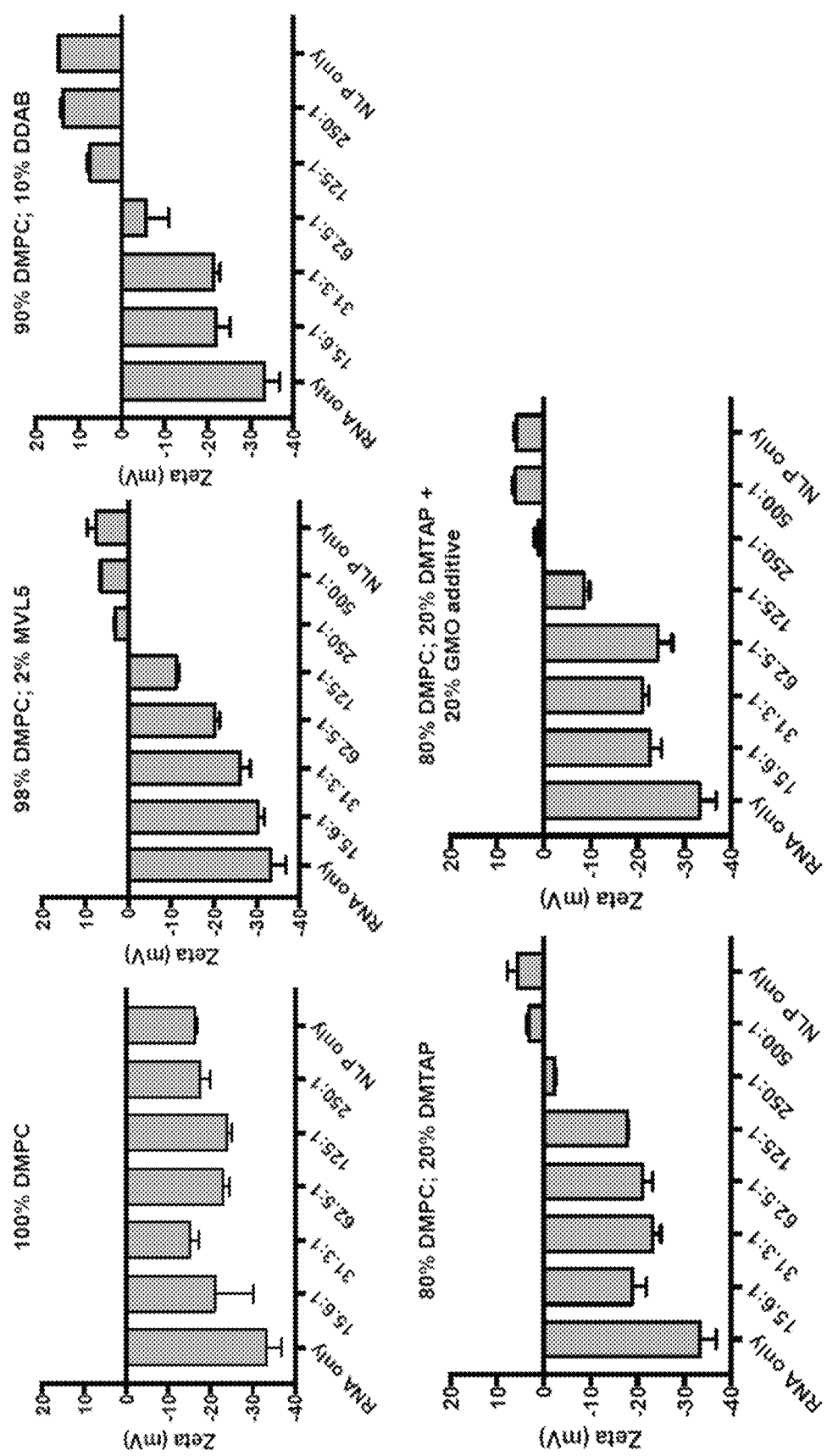
FIG. 10 shows graphs of Zeta Potential distributions (measured in millivolts, mV) in some embodiments. Zeta potential was characterized for various cationic-NLP:RNA formulations at the ratios of NLP:RNA indicated in the X-axes. Results for bulk lipid DMPC, or DMPC with 2% cationic lipid MVL5, DMPC with 10% cationic lipid DDAB, DMPC with 20% cationic lipid DMTAP, or DMPC with 20% cationic lipid DMTAP and 20% glyceryl monooleate (GMO) additive are shown. RNA alone is shown as a control. Scaffold protein ApoE4 was used for DMPC alone, DMPC with 2% cationic lipid MVL5, and DMPC with 10% cationic lipid DDAB. Scaffold protein ApoA1 was used for DMPC with 20% cationic lipid DMTAP and DMPC with 20% cationic lipid DMTAP and 20% GMO additive.

For example, cationic-NLPs made with 1%, 2%, or 5% MVL5 and 99, 98, or 95% DMPC, respectively, indicate tight RNA binding at these low cationic lipid percentages as compared to other types of cationic-NLP RNA complexes such as the ones of Formula (XVIII). For example, cationic-NLPs made with 5, 10, or 20% DDAB with 95, 90, 80% DMPC, respectively, bind to RNA at higher cationic lipid percentages than MVL5 containing cationic-NLPs (FIG. 10).

Figure 13:
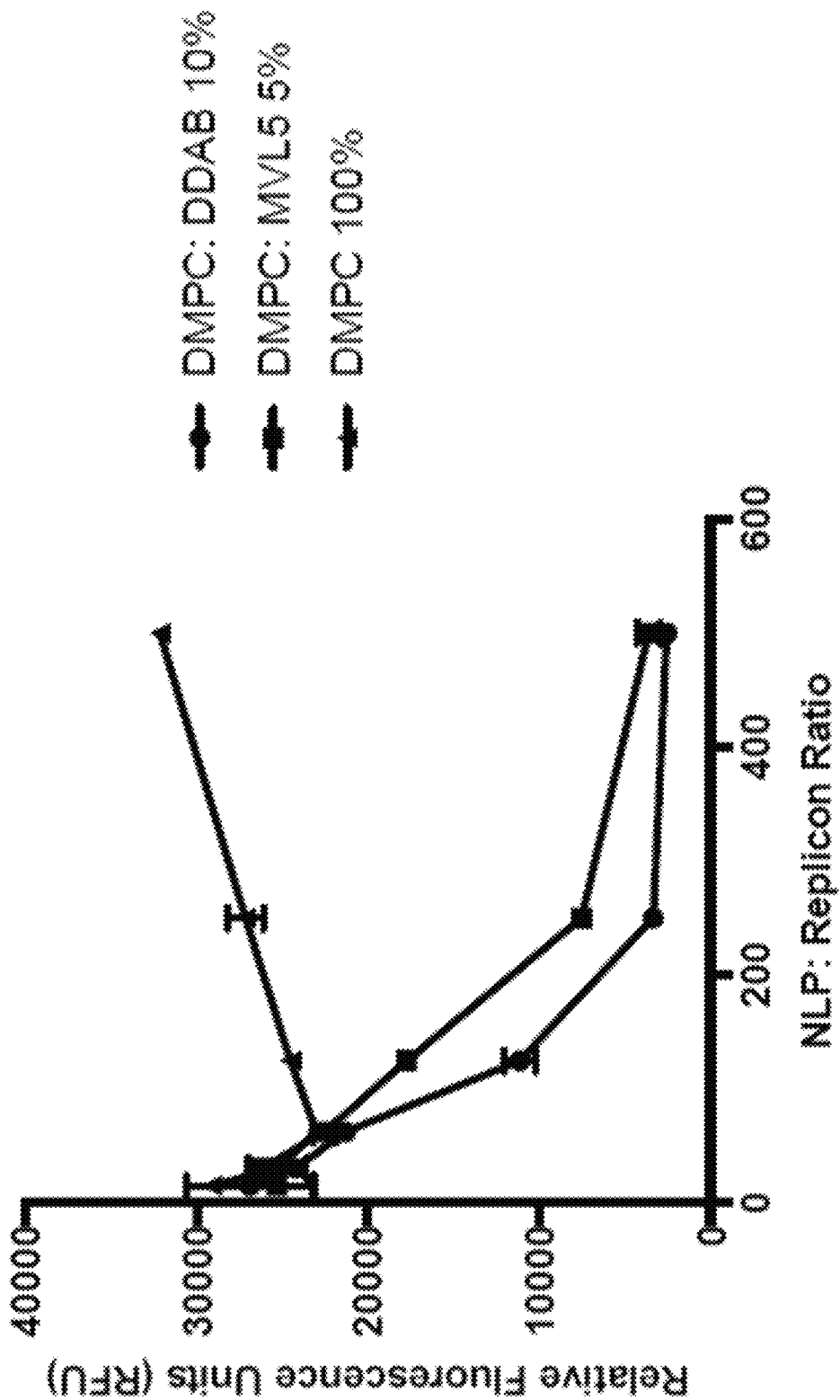
FIG. 13 shows a graph of results of Dye Exclusion analysis of NLP:Replicon ratio, measured in relative fluorescence units. Results are shown for NLP complexes comprising 100% DMPC (triangle), or NLP comprising DMPC with 10% DDAB (circle), or DMPC with 5% MVL5 (square). The ApoE4 scaffold protein was used for DMPC alone and with additional cationic lipids 5% MVL5, and 10% DDAB.

In some embodiments, the size of cationic-NLPs;RNA complex herein described can be controlled by appropriate selection of the scaffold protein of the cationic-NLPS. In particular, in the exemplary embodiment where the scaffold protein is ApoA1 the related cationic-NLPs tend to form cationic-NLP RNA complexes larger than 500 nm in diameter as the ratio of cationic-NLP to RNA increases beyond 250:1 ratio. In the exemplary embodiment where the scaffold protein is ApoE4 cationic-NLPs are not form as large of complexes as the ApoA1-cat NLP complexed with RNA (FIG. 13). In some embodiments, cationic NLPs formed with ApoA1 complexes can have a size below 100 nm. In some embodiments, cationic NLPs formed with ApoA1 can have a size larger than 100 nm and smaller than 1000 nm. In addition to the size difference, the specific ratios of cationic-NLP:RNA associated with a selection of a specific is expected to affect stability.

In some embodiments selection of the concentration of the cationic lipid in the NLPs is performed to control the overall charge of the cationic-NLPs to control the stability of the cationic-NLP RNA complex. In particular, such selection can be performed in view of the type and amount of membrane forming lipid and cationic lipids as will be understood by a skilled person upon reading of the present disclosure.

The cationic NLPs:RNA complex described herein increase endocytosis and trigger enhanced cellular uptake when in contact with the cells. Once inside the cell, the scaffold proteins can help the RNA molecule escape from endosomal digestion through a "recycling mechanism" [31] (Takahashi and Smith, PNAS, 1999; Hassan et al., JBC, 2007). Naturally, after HDL particles are taken up by endocytosis, some of the apolipoproteins are redirected to an alternative pathway to avoid being degraded in lysosomes. The spared apolipoproteins are subsequently transported back toward the cell surface to be "recycled". This provides a possible reason to account for the enhanced in vivo transfection. In addition, the cationic NLPs also provide a good leaving group that may release the RNA quickly upon rerouting back toward the plasma membrane, allowing the RNA to refold quickly and translate with greater efficiency.

In some embodiments, the cationic NLPs herein described further comprise additives including membrane associated proteins, amphiphilic polymers, and immunogenic adjuvants such as monophosphoryl lipid A (MPLA) or CpG oligodeoxynucleotides (CpG). These additives can be added during the assembly of the NLP herein describe also comprising one or more cationic lipids. The addition of additives display a great potential for NLP use a drug delivery vehicle [30, 33, 34]. Additional exemplary additives also include cholesterol, CpG-cholesterol, lyso lipids, monolein (GMO), Tween 20 and Z3-14, as shown in Table 1. In particular, a variety of lipid or non-lipid additives can be added to the cationic NLP assembly at different percentages, including small molecule surfactants, single chain lipids, amphiphilic polymers and immunogenic adjuvant molecules. In general, the additive is a hydrophobic or amphipathic molecule that can incorporate fully or partially into the lipid bilayer.

In some embodiments, the cationic NLPs comprise membrane forming lipids, cationic lipids and additives, whereby the additives are present at a mol % ranging from 1 to 60, relative to total lipid (membrane forming and cationic lipids). In some embodiments, the GMO is used as the additive, and the molar ratio of the GMO with respect to the total lipid component comprising the membrane forming lipids and cationic lipids is 1:99 to 60:40. In some particular embodiments, the cationic NLPs-RNA complexes comprise DMPC as membrane forming lipids, DMTAP as cationic lipids, GMO as additives and RNA replicon at a molar ratio from 2,400:800:800:1 to 12,000:4,000:4,000:1, preferably at 2,400:800:800:1. In some embodiments, poly-arginine containing a lipidic tail is used as the additive, and the molar ratio of the poly-arginine with respect to the total lipid component comprising the membrane forming lipid and the cationic lipid is 1:99 to 1:9. In some particular embodiments, the cationic NLPs-RNA complexes comprise DMPC as membrane forming lipids, DMTAP as cationic lipids, GMO as additives and RNA replicon at a molar ratio from 3,120:800:80:1 to 15680:4,000:320:1.

In some embodiments, the addition of additive molecules allows fine-tuning the NLP to RNA replicon binding as well as replicon in vivo transfection efficiency, such as to enhance the NLP-based RNA delivery and release, as shown in Example 8 of the current disclosure. In particular, the introduction of GMO into the cationic NLPs is able to reduce the total amount of lipids used in the NLPs from a NLP:RNA ratio of 250:1 to 50:1 while still retaining comparable in vivo transfection efficiency.

In some embodiments, functionalized lipid additives can also reinforce/stabilize the cationic-NLP. Several functionalized lipids, including DSPE PEG 2000 Azide, 16:0 Azido Cap PE, and poly-arginine containing a lipidic tail can successfully be incorporated into the cationic-NLP (LLNL slide deck-30 and 36). Other additives, including cholesterol, CpG-Cholesterol, lyso lipid, monoolein (GMO), Tween 20, and Z3-14 can all be incorporated into the cationic-NLP and form stable particles.

In some embodiments, the cationic NLPs herein described further comprise one or more telodendrimers to form telocationic-NLPs. The term "telodendrimer" refers to a dendrimer containing a hydrophilic PEG segment and one or more chemical moieties covalently bonded to one or more end groups of the dendrimer. These moieties can include hydrophobic groups, hydrophilic groups, amphiphilic compounds, and drugs. Different moieties may be selectively installed at desired end groups using orthogonal protecting group strategies.

The terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendritic polymer can be attached to other segments of the telodendrimers, and the end groups may be further functionalized with additional chemical moieties.

The terms "monomer" and "monomer unit" refer to repeating units that make up the dendrons of the dendritic polymers disclosed herein. The monomers can be AB2-type monomers, where A and B are two different functional groups capable of reacting together such that the resulting polymer chain has a branch point where an A-B bond is formed. Exemplary monomers include a diamino carboxylic acid, a dihydroxy carboxylic acid and a hydroxyl amino carboxylic acid. Examples of diamino carboxylic acid groups include 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid and 5-amino-2-(3-aminopropyl)pentanoic acid. Examples of dihydroxy carboxylic acid groups include glyceric acid, 2,4-dihydroxybutyric acid, and 2,2-bis(hydroxymethyl)propionic acid. Examples of hydroxyl amino carboxylic acids include serine and homoserine. One of skill in the art will appreciate other monomer units useful in the current disclosure.

In embodiments herein described, telo-cationic-NLPs can be prepared using similar procedures previously described for the assembly of cationic-NLPs. In particular, the cationic lipids, membrane forming lipids, telodendrimers and scaffold protein component can be mixed to form an admixture for a time and under conditions allowing assembling of the telo-cationic-NLPs according to the methods above described.

For example, in some embodiments, telo-cationic NLPs herein described can be prepared by adding the telodendrimers to the assembly mixture containing the solubilized lipids and scaffold proteins prior to surfactant removal and allowing the incorporation of the telodendrimers into NLPs, followed by detergent removal as described for example in in [2-4].

In general, assembly of telo-cationic NLPs can be accomplished with a wide range of ratios of total membrane forming lipids to scaffold proteins as previously described. Telodendrimer can be incorporated in amounts ranging from 0.1 to 10% of the lipid component, with a preferred amount between 0.1 and 2%.

In some embodiments, the telodendrimers comprise 5KCA8 or cys-5KCA8 in amounts from 0.1% to about 1% (±0.01%). In some particular embodiments, the telodendrimers such as 5KCA8 or cys-5KCA8 can be incorporated into cationic NLPs comprising scaffold protein apoA1, 80% membrane forming lipids DMPC and 20% cationic lipid DMTAP (see Example 9). In these embodiments, the cationic NLPs can further comprise 20% GMO as additives in addition to the total lipid component. In some other embodiments, the telodendrimers such as 5KCA8 or cys-5KCA8 can be incorporated into cationic NLPs comprising scaffold protein apoA1, 90% membrane forming protein DMPC and 10% cationic lipid DDAB, cationic NLPs comprising scaffold protein apoE4, 70% membrane forming lipid DMPC and 30% cationic lipid DODAP, cationic NLPs comprising scaffold protein apoE4, 98% membrane forming lipid DMPC and 2% cationic lipid MVL5, cationic NLPs comprising scaffold protein apoE4, 95% membrane forming lipid DMPC and 5% cationic lipid MVL5, cationic NLPs comprising scaffold protein apoA1, 60% membrane forming lipid DMPC and 40% cationic lipid DMEPC, and cationic NLPs comprising scaffold protein apoA1, 60% membrane forming lipid DMPC, 20% cationic lipid DOPE and 20% cationic lipid DODAP.

Benefits of further incorporating telodendrimer into the cationic NLPs include reducing NLP-NLP aggregation, providing a way to fine-tune the size of the NLPs, and providing a chemical moiety that is amenable to conjugation or modification. In addition, PEgylation of nanoparticle or nanoparticle:RNA complex can confer stealth and provide increased stability and less susceptibility in vivo.

In some embodiments, the cationic-NLPs and/or cationic-NLPs polynucleotide complexes can be comprised in a composition together with a suitable vehicle. The term "vehicle" as used herein indicates any of various media acting usually as solvents, carriers, binders or diluents for the cationic-NLPs and/or cationic-NLPs polynucleotide complexes are comprised in the composition as an active ingredient. In particular, the composition including the multi-cationic-NLPs and/or cationic-NLPs polynucleotide complexes can be used in one of the methods or systems herein described.

In some embodiments, an NLP can be included in pharmaceutical compositions (e.g. a vaccine) together with an excipient or diluent. In particular, in some embodiments, pharmaceutical compositions are disclosed which contain NLP, in combination with one or more compatible and pharmaceutically acceptable vehicle, and in particular with pharmaceutically acceptable diluents or excipients. By "pharmaceutically acceptable" it is meant the carrier, diluent or excipient must be compatible with the other ingredients of the formulation and not deleterious to the recipient thereof.

The term "excipient" as used herein indicates an inactive substance used as a carrier for the active ingredients of a medication. Suitable excipients for the pharmaceutical compositions herein disclosed include any substance that enhances the ability of the body of an individual to absorb the NLP. Suitable excipients also include any substance that can be used to bulk up formulations with NLP to allow for convenient and accurate dosage. In addition to their use in the single-dosage quantity, excipients can be used in the manufacturing process to aid in the handling of NLP. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

In certain embodiments, compositions and, in particular, pharmaceutical compositions can be formulated for systemic administration, which includes parenteral administration and more particularly intravenous, intradermic, and intramuscular administration. In some embodiments, compositions and, in particular, pharmaceutical compositions can be formulated for non-parenteral administration and more particularly intranasal, intratracheal, vaginal, oral, and sublingual administration.

The terms "administration of" and or "administering" should be understood to mean providing a pharmaceutical composition in a therapeutically effective amount to the subject in need of treatment. The terms "therapeutically effective amount" refer to the amount of the subject compound that will elicit the biological or medical response of a tissue, system, animal or human.

The term "subject" as used herein refers to any individual or patient to which the subject methods are performed. Generally the subject is human, although as will be appreciated by those in the art, the subject may be an animal. Thus other animals, including vertebrate such as rodents (including mice, rats, hamsters and guinea pigs), cats, dogs, rabbits, farm animals including cows, horses, goats, sheep, pigs, chickens, etc., and primates (including monkeys, chimpanzees, orangutans and gorillas) are included within the definition of subject.

Exemplary compositions for parenteral administration include but are not limited to sterile aqueous solutions, injectable solutions or suspensions including NLP. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

The term "lyophilization" (also known as freeze-drying or cryodesiccation) indicates a dehydration process typically used to preserve a perishable material or make the material more convenient for transport. Freeze-drying works by freezing the material and then reducing the surrounding pressure and adding enough heat to allow the frozen water in the material to sublime directly from the solid phase to gas.

If a freeze-dried substance is sealed to prevent the reabsorption of moisture, the substance may be stored at room temperature without refrigeration, and be protected against spoilage for many years. Preservation is possible because the greatly reduced water content inhibits the action of microorganisms and enzymes that would normally spoil or degrade the substance.

Lyophilization can also cause less damage to the substance than other dehydration methods using higher temperatures. Freeze-drying does not usually cause shrinkage or toughening of the material being dried. In addition, flavours and smells generally remain unchanged, making the process popular for preserving food. However, water is not the only chemical capable of sublimation, and the loss of other volatile compounds such as acetic acid (vinegar) and alcohols can yield undesirable results.

Freeze-dried products can be rehydrated (reconstituted) much more quickly and easily because the process leaves microscopic pores. The pores are created by the ice crystals that sublimate, leaving gaps or pores in their place. This is especially important when it comes to pharmaceutical uses. Lyophilization can also be used to increase the shelf life of some pharmaceuticals for many years.

In pharmaceutical applications freeze-drying is often used to increase the shelf life of products, such as vaccines and other injectables. By removing the water from the material and sealing the material in a vial, the material can be easily stored, shipped, and later reconstituted to its original form for injection In some embodiments, cationic-NLPs herein described can be used to deliver one or more polynucleotide molecules to target environment is described. The method comprises contacting the target environment with one or more cationic-NLPs-polynucleotide complexes herein described comprising the one or more polynucleotide molecules.

In some embodiments, cationic-NLPs herein described methods and systems for delivery of polynucleotides to facilitate gene expression of therapeutic proteins (non-vaccine applications).

In some embodiments, cationic-NLPs herein described can be used to in methods and systems to perform an assay on polynucleotides loaded in the cationic-NLP-nucleotide complexes of the present disclosure According to additional aspects, cationic-NLPs and related complexes can be used in methods and systems, comprising forming and using the cationic nanolipoprotein particles herein described are also provided in the present disclosure.

In some embodiments, cationic NLPs herein described and related components can be provided as a part of systems in accordance to various embodiments herein described.

In some embodiments, the systems herein described can be provided in the form of kits of parts. In a kit of parts, membrane forming lipid and cationic lipids can be provided in various combinations with one or more functionalized amphipathic compounds, one or more membrane protein, one or more additives, one or more telo-dendrimers, and/or scaffold proteins or fragments thereof. In the kits of parts, the components can be comprised in the kit independently possibly included in a composition together with suitable vehicle carrier or auxiliary agents.

Additional components can also be included and comprise, reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the methods herein described, can also be included in the kit. The kit can also contain, depending on the particular method used, other packaged reagents and materials (i.e. wash buffers and the like).

In some embodiments, a method of delivering a polynucleotide to a target environment comprising contacting the target environment with a cationic-nanolipoprotein (NLPs)-polynucleotide complex is provided. In specific embodiments, the target environment in a cell or a tissue. In other embodiments, a method of delivering a polynucleotide to a subject comprising administering to the subject a cationic nanolipoprotein (NLPs)-polynucleotide complex is provided. A method of inducing expression of a protein in a subject comprising administering to the subject a cationic nanolipoprotein (NLPs)-polynucleotide complex, is also provided. Further, a method of stimulating a humoral and a cellular immune response in a subject comprising administering to the subject a cationic nanolipoprotein (NLPs)-polynucleotide complex is provided. In specific embodiments, the cationic NLPs polynucleotide complex comprises one or more cationic lipids and a membrane forming lipid arranged in a discoidal membrane lipid bilayer stabilized by a scaffold protein attached to a polynucleotide, the polynucleotide is an RNA replicon, and the cationic NLPs polynucleotide complex further comprises an adjuvant, a functional polymer, a membrane-associated protein for targeted delivery, or a combination thereof. In specific embodiments, the subject is human.

In some embodiments, a pharmaceutical composition comprising a nanolipoprotein or a cationic-nanolipoprotein-polynucleotide complex and a pharmaceutically acceptable vehicle is provided.

Further details concerning the identification of the suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting. In particular, cationic NLPs comprising various membrane forming lipids, cationic lipids, additives, telo-dendrimers alone or together with RNA replicon to form NLP-RNA complex were prepared and characterized in vitro and in vivo. A skilled person will be able to use other membrane forming lipids, cationic lipids, additives, telo-dendrimers, scaffold proteins and RNA molecules herein described. The following materials and methods were used Protein expression and purification: The expression clone for the 22 kDa N-terminal fragment of human apolipoprotein E4 (apoE422k, kindly provided by Dr. Karl Weisgraber) featuring a cleavable His-tag [61] was expressed and purified as previously described. [5, 62]. ApoA1 featured an N-terminal His-tag and was expressed and purified as described for apoE4 above. However, since the apoA1 expression product was not a fusion protein, thrombin-based cleavage or subsequent gel purification were not required.

Cationic NLP synthesis NLPs were synthesized according to a previously described in vitro assembly method [1] with slight modifications. Briefly, bulk lipid and cationic lipid(s) of choice dissolved in chloroform were formulated at various molar percentages. Chloroform was then removed using a continuous stream of $N_2$ gas and further dried via vacuum. Lipids were re-dissolved in PBS buffer containing 30 mM cholate and incubated at 20-25° C. for 1 hour, shaking at 1400 rpm. Scaffold proteins ApoA1 (80:1), ApoE3 (170:1) and ApoE4 (170:1) scaffold protein:lipid molar ratios were then added to the lipid/cholate mixture and incubated, shaking, for another hour. Subsequently, bio beads (Bio-Rad) were added and left shaking overnight 20-25° C. at 1100 rpm to remove the cholate. Biobeads were then filtered and NLP filtrate was run on SEC to analyze NLP formation.

Preparation of Replicon RNA Replicon RNA was acquired from SGVI and was synthesized using previously published methods (B. Bosworth, M. M. Erdman, D. L. Stine, I. Harris, C. Irwin, M. Jens, et al. Replicon particle vaccine protects swine against influenza. *Comp Immunol Microbiol Infect Dis*, 33 (6) (2010))

Preparation of RNA/NLP formulation Replicon was formulated with NLP at various NLP:Replicon (N/R) molar ratios. Replicon was prepared at 20 μg/ml in PBS for most formulations, but varied from 2 μg/ml to 600 μg/ml. To make formulations, the order of addition was PBS, replicon, and NLP. The formulations were incubated at room temperature for at least 5 minutes, then were subsequently used for further characterization or mouse injection.

RNase protection assay Naked RNA and NLP:Replicon complex were exposed to 3.8 mAU of RNase A (Life Technologies) per μg RNA for 1 minute at room temperature. RNase was then inactivated with the addition of 2 AU of Anti-RNase (Life Technologies) per 1 ng RNase at room temperature for 30 minutes. Afterwards, 1% Triton was added to each sample to disrupt NLP and release RNA. A 1% agarose TAE gel was prepared and loaded. 0.1 μg RNA was loaded per lane, and the gel was run at 90V for 30 minutes. Gel was then stained with SYBR Gold (Invitrogen; 1:1000 dilution in water) for 1 hour while shaking. Gel was imaged with Kodak Gel Logic 200 with Trans UV.

Dye exclusion analysis NLP: Replicon complexes were formulated at various molar ratios. In short, PBS, RNA, then NLP were mixed together and allowed to incubate at room temperature for at least 5 minutes. 0.1 μg RNA was added to each vial. Dye intercalation was visualized via Quant-iT Ribogreen RNA Reagent and Kit (Invitrogen) according to manufacturer's instructions.

RT-PCR quantitation Naked RNA and NLP:Replicon complexes were prepared as described in "RNase protection assay" for RNase and Anti-RNAse treatment. QuantiTect Probe RT-PCR kit (Qiagen) was used to run samples, adding 1% Triton to the Master Mix. 5 ng RNA was loaded per PCR well. PCR was run at 30° C. for 30 minutes, 95° C. for 15 minutes, then [95° C. for 15 seconds, 60° C. for 30 seconds]×30 cycles] (7900 HT Fast Real-Time PCR Machine; Applied Biosystems/Life Technologies). Crossing threshold (Ct) analysis was performed on the resulting amplification curves.

Zeta potential analysis The Zeta potential and particle size of the NLP and NLP-Replicon complex were measured using a Zetasizer Nano ZS 90 (Malvern Instruments, Orsay, France). NLP or NLP-Replicon samples were diluted in 1 ml water solution containing 4% PBS. Zeta potential and size distribution were analyzed at 25° C. according to the manufacturer's instructions. Particle sizes are reported as Number Mean (d.nm) with the polydispersity index (pdi).

In vivo transfection and evaluation All the mice were obtained from Envigo and housed at Lawrence Livermore National Laboratory Animal Care Facility. The experiments were approved and conducted according to the IACUC. All mice were female BALB/c, aged 6-10 weeks and weighing between 15 and 25 g. Mice were bilaterally injected with unformulated RNA or NLP formulated RNA complexes in quadriceps. After 4 to 5 days, mice were imaged at UC Davis Center for Molecular and Genomic Imaging (CMGI). Five minutes before imaging, mice were injected intraperitoneally with 150 mg/kg of luciferin solution (Caliper Lifesciences). Mice were then anesthetized [2% (vol/vol) isoflurane in oxygen] and transferred to the IVIS Spectrum instrument (Perkin Elmer). All images were quantified based on the total flux (photons per second) and all parameters were kept constant across experiments.

Example 1: High Throughput Synthesis of Cationic-NLPS

Truncated versions of mouse apolipoproteins, apoA1-Δ49 and apoE4-22k as candidate scaffold proteins were used for the cationic-NLP synthesis (respectively referred to apoA1 and ApoE4). For the NLP zwitterionic bulk lipids, DOPC, POPC and DMPC were used; all of which have shown stable NLP formation [2] [3] [4]. Also, a wide range of cationic lipids and additives at different percentages were tested to verify the compatibility with the scaffold protein and bulk lipid of interest (Table 1). Table 1 lists various scaffold proteins, bulk lipids, cationic lipids, and other additives tested for high throughput cationic-NLP synthesis.

TABLE 1

High Throughput cationic-NLP Synthesis.

| Scaffold Proteins | Zwitterion Bulk Lipids | Cationic Lipids | Other Additives |
|---|---|---|---|
| ApoA1 | DMPC | DC-Cholesterol | Cholesterol |
| ApoE4 | DOPC | DDAB | CpG-Cholesterol |
|  | POPC | DMEPC | Lyso Lipid |
|  |  | DMTAP | Monoolein |
|  |  | DODAP | (GMO) |
|  |  | DOEPC | Tween 20 |
|  |  | DOPE | Z3-14 |
|  |  | DOTAP |  |
|  |  | DOTMA |  |
|  |  | MVL5 |  |

Figure 2:
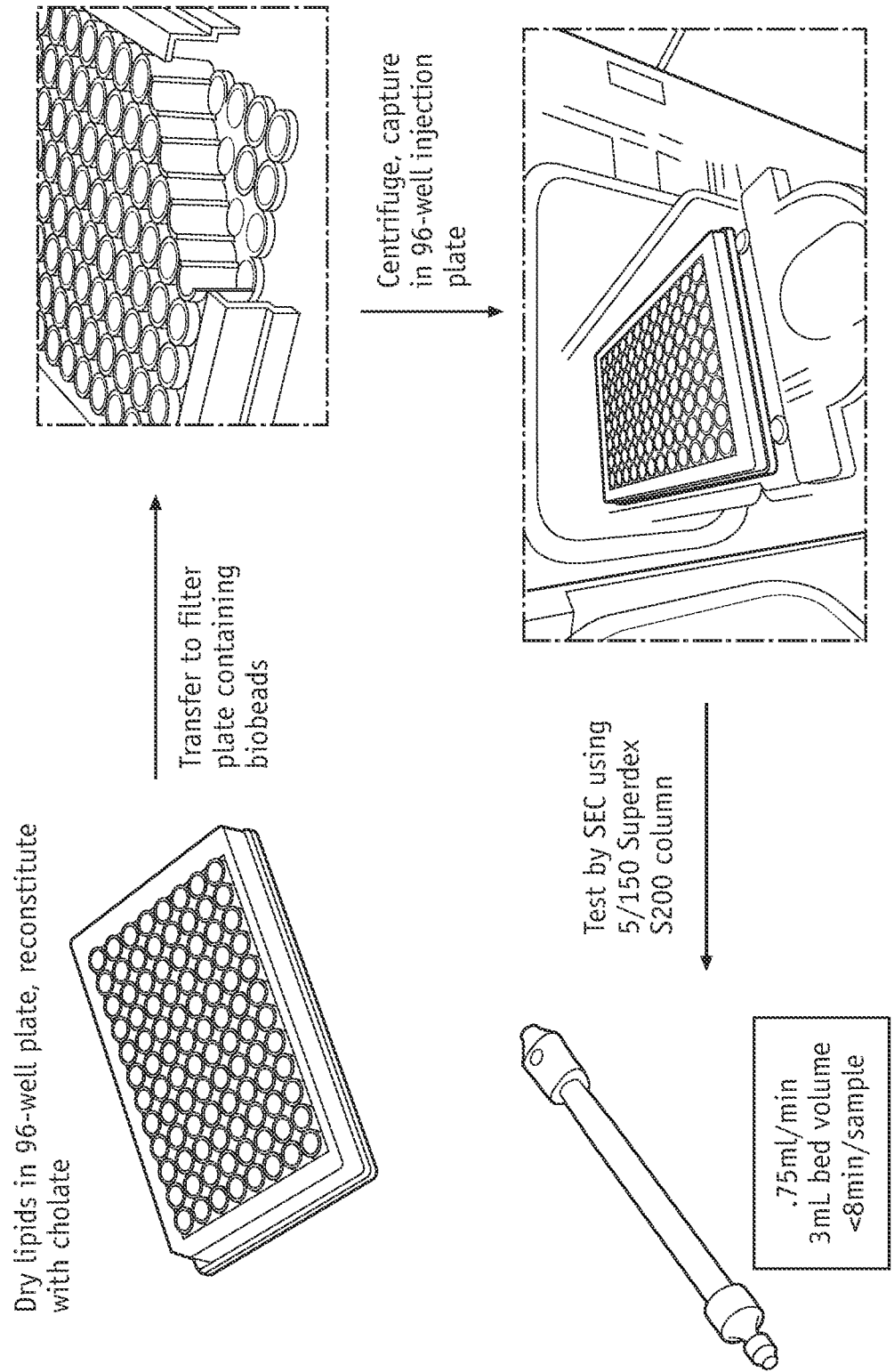
FIG. 2 shows an exemplary High Throughput Screen (HTS) approach that can be used to screen cationic-NLP formation in which different steps are schematically indicated by arrows.

For high throughput screening, the cationic-NLPs were synthesized on a 96 well plate as shown schematically in FIG. 1 and FIG. 2 and were directly injected onto size exclusion chromatography (SEC) to access for proper NLP formation.

Example 2: Determination of Formation of Cationic-NLPS by Analytical Size Exclusion Chromatography (SEC)

The assembly of cationic-NLPs synthesized according to the procedure described in Example 1 was evaluated using a High Throughput Screening (HTS) approach illustrated in FIG. 2.

NLPs were synthesized according to a previously described in vitro assembly method with slight modifications (Fischer, N. O. et al. Evaluation of nanolipoprotein particles (NLPs) as an in vivo delivery platform. *PLoS One* 9 (2014)). Briefly, bulk lipid and cationic lipid(s) of choice dissolved in chloroform were formulated at various molar percentages in a round bottom polypropylene 96 well plate. Chloroform was then removed using a continuous stream of N2 gas and further dried via vacuum. Lipids were redissolved in PBS buffer containing 30 mM cholate and incubated at 20-25° C. for 1 hour, shaking at 1000 rpm. Scaffold proteins ApoA1 (80:1) and ApoE (170:1) scaffold protein:lipid molar ratios were then added to the lipid/cholate mixture and incubated, shaking at 1000 rpm for another hour. Subsequently, lipid protein mixture was transferred to a 96 well Durapore membrane filter plate (Millipore). Bio beads (Bio-Rad) were added to wells and left at 20-25° C. for 1 hour, shaking at 800 rpm to remove the cholate. Biobeads were then filtered by centrifuging the plate at 1,000 rpm for 1 minute. NLP filtrate was collected in a Shimadzu conical bottom shallow 96 well plate. Plate was then covered with Shimadzu Teflon/silicone mat. NLP filtrate was run on SEC to analyze NLP formation.

The SEC traces from the high throughput NLP synthesis were numerically scored 0 to 2 based on the peak height and size of NLP formed, homogeneity of the NLP population, as well as the percentage of large aggregates and remaining free proteins.

Figure 3:
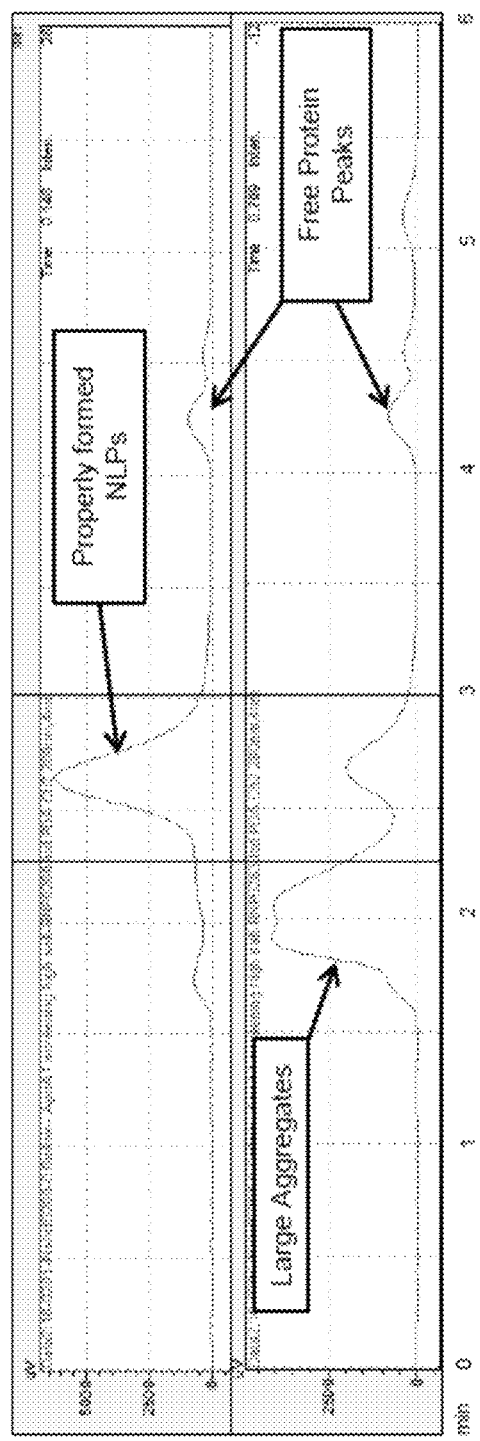
FIG. 3 shows exemplary results of High Throughput SEC screening of NLPs. In the illustration of FIG. 3, the X-axis is SEC retention time (in minutes), the y-axis is absorbance intensity (in microvolts). NLPs were scored based on homogeneity of the NLP peak, the intensity of the free protein peak, as well as the amount of large aggregate species. The top SEC trace is an example of successful NLP formation, with scaffold protein apoA1, 80% DMPC bulk lipid, and 20% DMTAP cationic lipid. It received a score of 2. The bottom SEC trace shows poor NLP formation with scaffold protein apoA1, 80% DMPC bulk lipid, and 20% DOEPC cationic lipid. It received a score of 0.

FIG. 3 shows exemplary SEC results of successful formation of cationic NLP, that received a score of 2 (upper panel), and poor NLP formation, that received a score of 0 (lower panel). The top SEC trace is an example of successful cationic NLP formation, with scaffold protein apoA1, 80% DMPC bulk lipid, and 20% DMTAP cationic lipid. It received a score of 2. The bottom SEC trace shows poor NLP formation with scaffold protein apoA1, 80% DMPC bulk lipid, and 20% DOEPC cationic lipid. It received a score of 0.

Stable cationic NLP formation is dependent on the type of scaffold protein, lipid identity, and molar ratios of all assembly constituents. The type of cationic lipid has profound impact on NLP formation. Various combinations of scaffold proteins, membrane forming lipids (bulk lipids), and cationic lipids at different ratios were tested. The results are shown in FIGS. 5-6.

Figure 6:
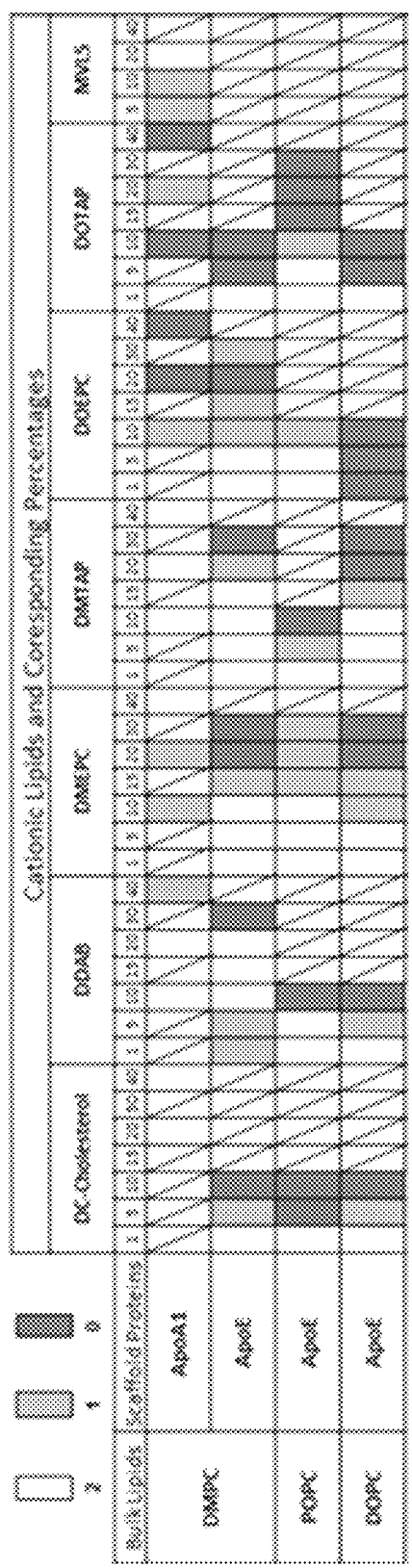
FIG. 6 shows a diagram illustrating a score chart of results of High Throughput testing of exemplary cationic-NLPs using SEC analysis. Several bulk lipids (DMPC, POPC, or DOPC), scaffold proteins (ApoA1 or ApoE4) and cationic lipids were tested and assessed for proper cationic-NLP formation. Cationic-NLPs comprising cationic lipids DC-cholesterol (3β-[N-(N',N'-dimethylaminoethane)-carbamoyl]cholesterol hydrochloride), DDAB (dimethyldioctadecylammonium (Bromide Salt)), DMEPC (1,2-dimyristoleoyl-sn-glycero-3-ethylphosphocholine), DMTAP (1,2-dimyristoyl-3-trimethylammonium-propane), DOEPC (1,2-dioleoyl-sn-glycero-3-ethylphosphocholine), DOTAP (1,2-dioleoyl-3-trimethylammonium-propane), or MVL5 (N1-[2-((1S)-1-[(3-aminopropyl)amino]-4-[di(3-amino-propyl)amino]butylcarboxamido)ethyl ]-3,4-di[oleyloxy]-benzamide), at percentages of 1%, 5%, 10%, 15%, 20%, 30% or 40% were tested. The detected assembly for each sample is shown in a score chart wherein full cationic-NLP assembly was given a score of 2 (white bar), cationic-NLPs assembly with margin loss in overall yield or homogeneity was given a score of 1 (light gray bar), and marginal cationic-NLP assembly with significant loss in yield or homogeneity was given a score of 0 (dark gray bar), which are separately indicated. If the combination was not tested, it is left blank (diagonal line). This is a representative depiction of the cationic-NLPs tested.

FIG. 6 shows a diagram illustrating a score chart of results of High Throughput testing of exemplary cationic-NLPs using SEC analysis. Several bulk lipids (DMPC, POPC, or DOPC), scaffold proteins (ApoA1 or ApoE4) and cationic lipids were tested and assessed for proper cationic-NLP formation. Cationic-NLPs comprising cationic lipids DC-cholesterol, DDAB, DMEPC, DMTAP, DOEPC, DOTAP, or MVL5, at percentages of 1%, 5%, 10%, 15%, 20%, 30% or 40% were tested. The detected assembly for each sample is shown in a score chart wherein full cationic-NLP assembly was given a score of 2 (dark gray bar), cationic-NLPs assembly with margin loss in overall yield or homogeneity was given a score of 1 (light gray bar), and marginal cationic-NLP assembly with significant loss in yield or homogeneity was given a score of 0 (black bar), which are separately indicated. If the combination was not tested, it is left blank. This is a representative depiction of the cationic-NLPs tested.

Figure 5:
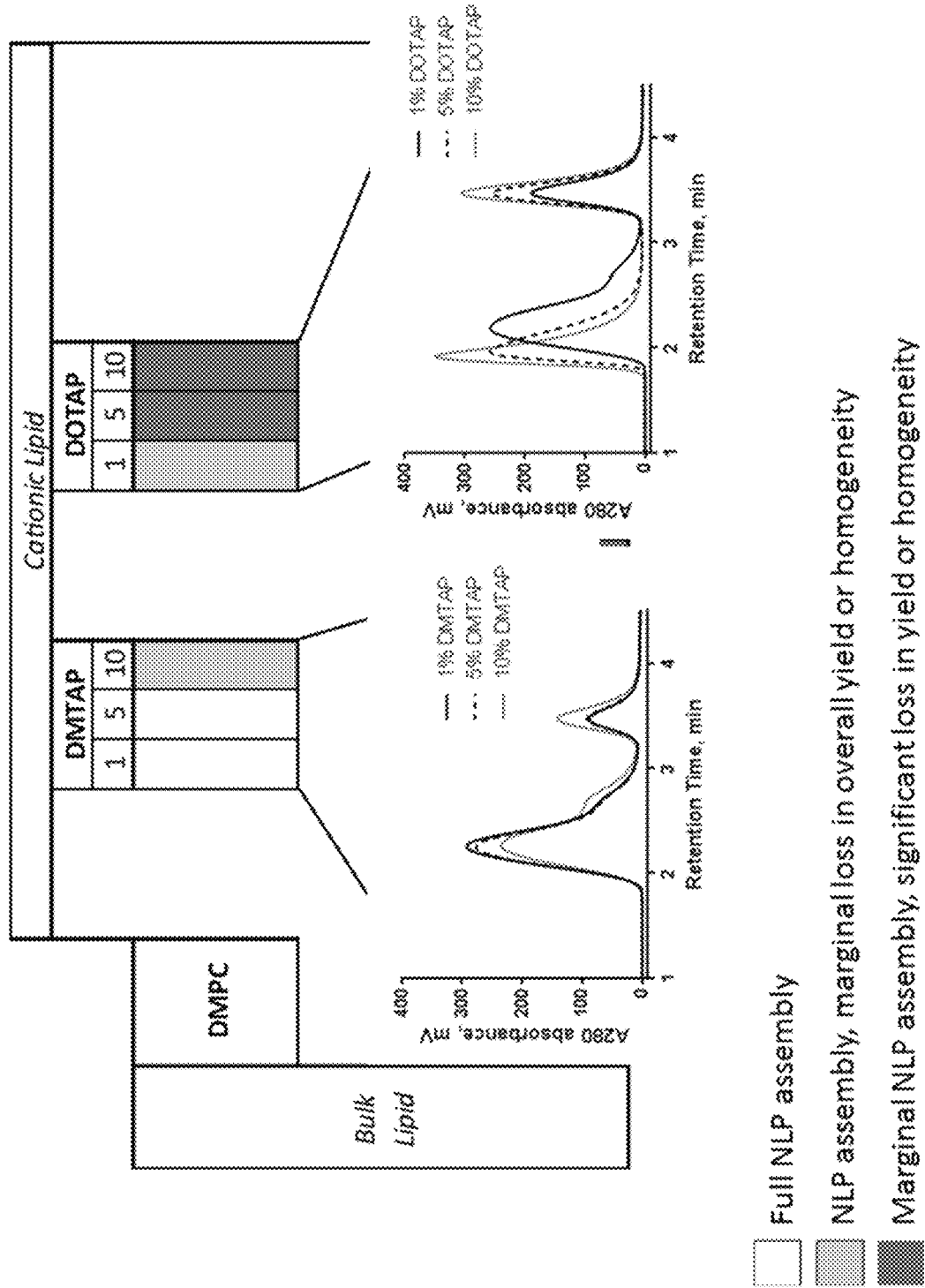
FIG. 5 shows diagrams illustrating exemplary results of size exclusion chromatography (SEC) performed on DMPC-containing cationic-NLPs comprising 1% DMTAP (black), 5% DMTAP (dashed), and 10% DMTAP (gray) (left panel) and on cationic-NLPs comprising 1% DOTAP (black), 5% DOTAP (dashed), and 10% DOTAP (gray) (right panel); in the illustration the detected assembly for each sample is shown in a score chart wherein full cationic-NLP assembly (white bar), cationic-NLPs assembly with margin loss in overall yield or homogeneity (light gray bar) and marginal cationic-NLP assembly with significant loss in yield or homogeneity (dark gray bar) are separately indicated.

FIG. 5 demonstrates how the quality of cationic-NLPs is assessed by size exclusion chromatography. The two chromatograms illustrate exemplary results of SEC performed on cationic-NLPs prepared with apoE comprising 1% DMTAP (black), 5% DMTAP (red), and 10% DMTAP (blue) (left panel) and on cationic-NLPs comprising 1% DOTAP (black), 5% DOTAP (red), and 10% DOTAP (blue) (right panel). Large non-NLP structures exhibit retention times less than 2 minutes. NLPs exhibit retention times between 2 and 2.7 minutes. Unincorporated scaffold protein exhibits retention times between 3.2 and 3.8 minutes. In the illustration the detected assembly for each sample is shown in a score chart wherein full cationic-NLP assembly (green bar), cationic-NLPs assembly with margin loss in overall yield or homogeneity (yellow) and marginal cationic-NLP assembly with significant loss in yield or homogeneity (red bar) are separately indicated.

The results shown in FIGS. 5-6 indicate that both apoA1 and apoE4 can form cationic NLP. Among the three membrane forming lipids tested, DMPC tolerated higher percentages of cationic lipid than POPC or DOPC. When DMPC is the bulk lipid, DMEPC, DODAP and DMTAP are among the most tolerated cationic lipids, and can comprise up to 40% of the total lipid. Other cationic lipids such as DDAB and MVL5 are well tolerated at up to 20%. It was also demonstrated that a variety of lipid or non-lipid additives can be added to the cationic NLP assembly, including small molecule surfactants, single chain lipids, amphiphilic polymers and immunogenic adjuvant molecules. Other factors like lipid to protein ratio and total lipid concentration in the assembly may also impact cationic NLP formation.

Figure 4:
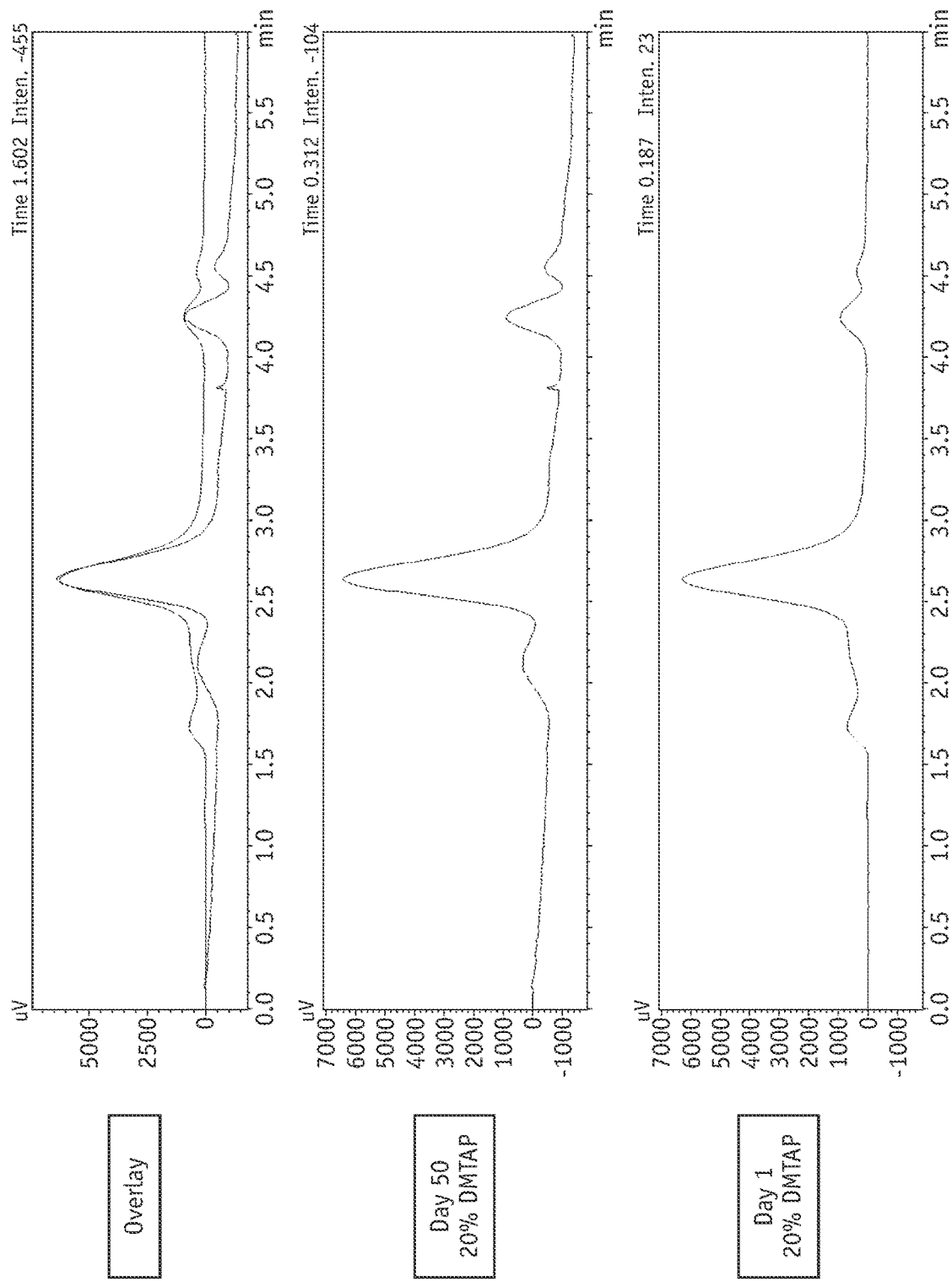
FIG. 4 shows examples of SEC results illustrating NLP Stability. In the illustration of FIG. 4, the X-axis is SEC retention time (in minutes), the y-axis is absorbance intensity (in microvolts). 80:20 DMPC:DMTAP NLPs were injected onto SEC on day 1 to assess for proper NLP formation (results shown in bottom panel). After 50 days, the same sample was injected onto SEC after being stored at 4° C. (results shown in middle panel). An overlay of both results is shown in the top panel. NLPs shown are formed with apoA1 scaffold protein.

SEC analysis was also used to assess cationic NLP stability. In FIG. 4, 80:20 DMPC:DMTAP NLPs were injected onto SEC on day 1 to assess for proper NLP formation (results shown in bottom panel). After 50 days, the same sample was injected onto SEC after being stored at 4° C. (results shown in middle panel). An overlay of both results is shown in the top panel. NLPs shown are formed with apoA1 scaffold protein. The results show that the cationic NLPs display the same size distribution as neutral NLPs and are stable when stored at 4° C. for 50 days.

Example 3: Gel Migration/retardation In Vitro Assessment of Cationic-NLP:Replicon Complexes The cationic NLPs with high scores were selected and further characterized for the ability to bind to replicon. These cationic NLPs were synthesized in a scaled-up reaction and purified by SEC. After purification, the cationic NLPs were mixed with replicon at various molar ratios. Subsequently, the cationic NLP-replicon association was assessed by the migration of replicon on agarose gel. The results are shown in the gel electrophoresis images in FIGS. 8 and 9, in which relative migration of RNA based on varying NLP:RNA molar ratios are shown.

Figure 8:
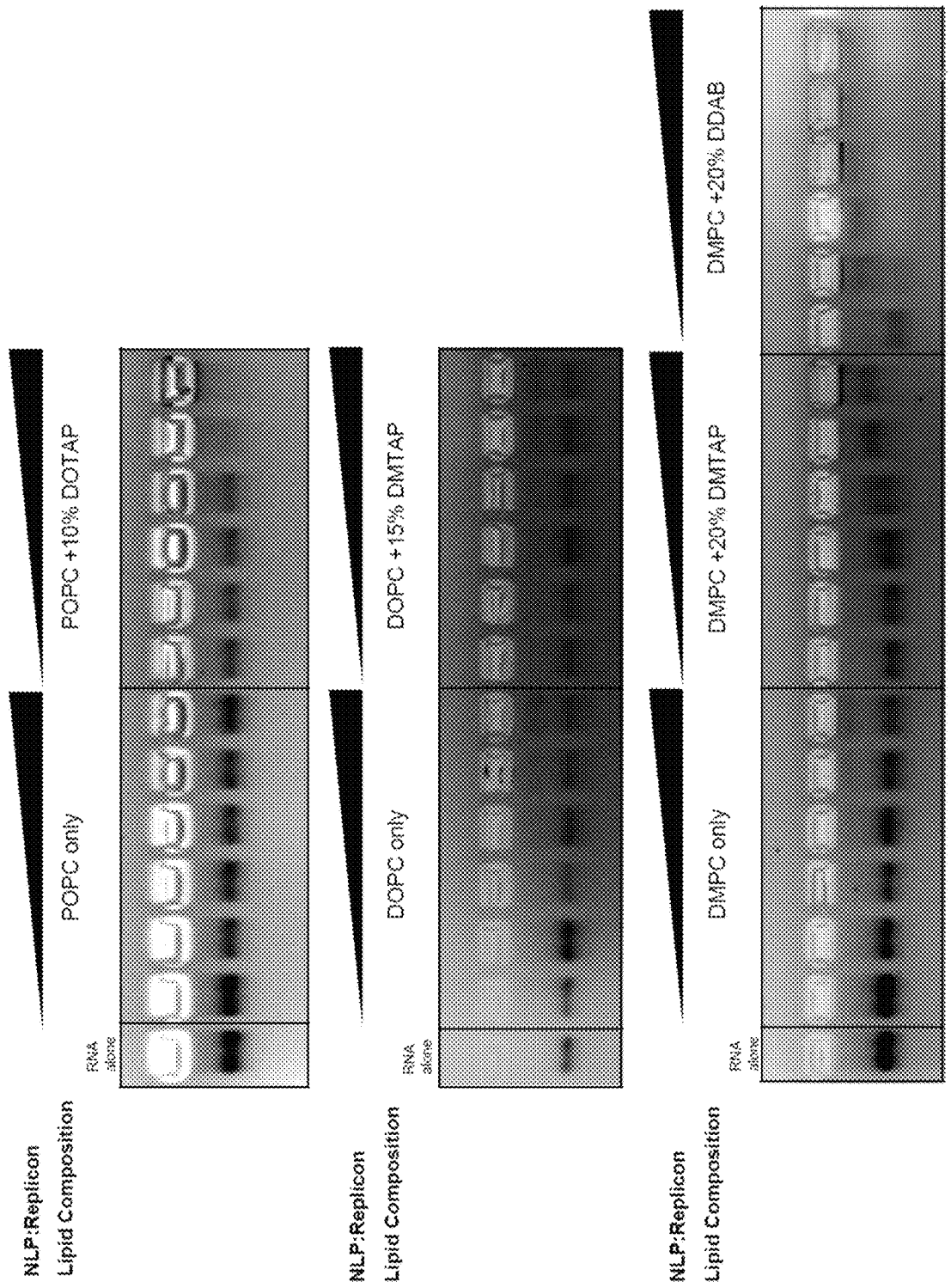
FIG. 8 shows images of gel electrophoresis results, in which relative migration of RNA based on varying NLP: RNA molar ratios are shown. Various bulk lipids (POPC, DOPC, or DMPC) are shown with several types of cationic lipids (DOTAP, DMTAP, or DDAB) at the percentages indicated. Each group shows increasing NLP:RNA molar ratios. NLP:RNA ratios are 15:1, 31:1, 62.5:1, 125:1, 250:1, and 500:1, respectively. All NLPs shown were formed with apoE4 scaffold protein. 0.1 µg RNA loaded in each well. RNA alone is shown as a control.

In FIG. 8, various bulk lipids (POPC, DOPC, or DMPC) are shown with several types of cationic lipids (DOTAP, DMTAP, or DDAB) at the percentages indicated. Each group shows increasing NLP:RNA molar ratios. NLP:RNA ratios are 15:1, 31:1, 62.5:1, 125:1, 250:1, and 500:1, respectively. All NLPs shown were formed with apoE4 scaffold protein. 0.1 µg RNA loaded in each well. RNA alone is shown as a control.

Figure 9:
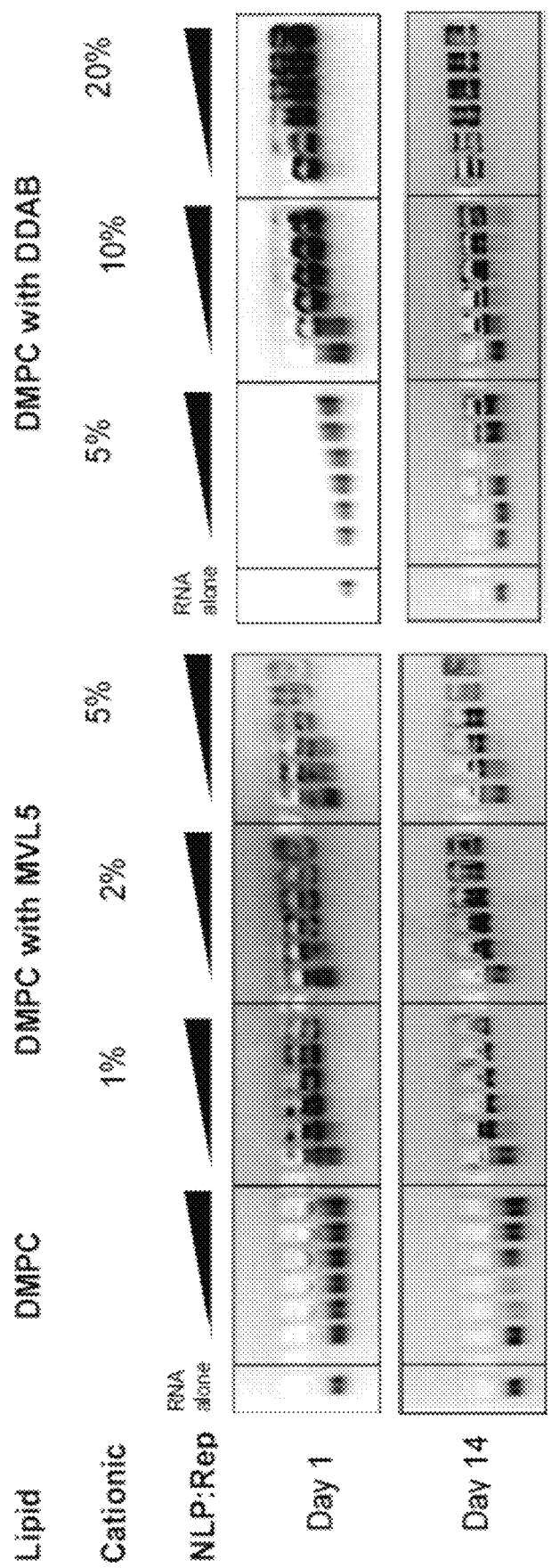
FIG. 9 shows images of gel electrophoresis results, in which relative migration of RNA with different cationic lipid percentages incorporated into NLPs are shown. Results for bulk lipid DMPC, or DMPC with cationic lipid MVL5 (1, 2, or 5%), or DMPC with cationic lipid DDAB (5, 10, or 20%) are shown. Each group shows increasing NLP:RNA molar ratios. NLP:RNA ratios are 15:1, 31:1, 62.5:1, 125:1, 250:1, and 500:1, respectively. Results are shown for NLP:RNA complexes either on day 1 or after 14 days stored at 4° C. All NLPs shown were formed with apoE4 scaffold protein. 0.1 µg RNA loaded per well. RNA alone is shown as a control.

In FIG. 9, results for bulk lipid DMPC, or DMPC with cationic lipid MVL5 (1, 2, or 5%), or DMPC with cationic lipid DDAB (5, 10, or 20%) are shown. Each group shows increasing NLP:RNA molar ratios. NLP:RNA ratios are 15:1, 31:1, 62.5:1, 125:1, 250:1, and 500:1, respectively. Results are shown for NLP:RNA complexes either on day 1 or after 14 days stored at 4° C. All NLPs shown were formed with apoE4 scaffold protein. 0.1 µg RNA loaded per well. RNA alone is shown as a control.

The results indicate that RNA migration on the agarose gel was measurably retarded upon its binding with the cationic NLPs, but not with neutrally charged NLPs. The relative migration also correlated with the percentage of cationic lipid in the NLP, as well as the ratio of cationic NLP to replicon. In short, the increased amount of cationic charged NLPs and higher NLP to replicon ratio slows down RNA migration. In some cases, the RNA failed to migrate out of the well, indicating either full charge attenuation or the formation of significantly large structures.

Experiments were also performed to demonstrate that these NLP:Replicon complexes are stable when stored at 4° C. over a span of two weeks (data not shown).

Example 4: Zeta Potential In Vitro Assessment of Cationic-NLP:Replicon Complexes Based on the ability to bind to RNA replicon, a selection of cationic-NLPs were further characterized to determine the zeta potential change of RNA replicon upon cationic-NLP binding at different molar ratios. It is noted that unformulated RNA has a zeta potential of 30 mV, whereas the cationic-NLPs exhibit a zeta potential of +10 mV, although this is highly dependent on the ratio of cationic-NLP to replicon.

Cationic NLPs were formulated with RNA replicon at molar ratios ranging from 15:1 to 500:1 (NLP:RNA) ratios. As shown in FIG. 10, at increasing cationic NLP to RNA ratios, the zeta potential of the complex became more positive. Cationic NLP:RNA complexes trend toward increasingly positive zeta potential with higher NLP:RNA ratios. Non-cationic charged NLPs, such as 100% DMPC, do not alter the intrinsically negative zeta potential of the RNA replicon. Depending on the type of NLP, the transition point from negative to positive zeta potential occurred a molar ratios between 62.5:1 and 250:1 (NLP:RNA). The zeta potential distribution shown in FIG. 10 illustrates that the cationic NLP:RNA complex forms a single complex that increases in overall positive charge with increasing cationic NLP:RNA ratios.

Figure 11:
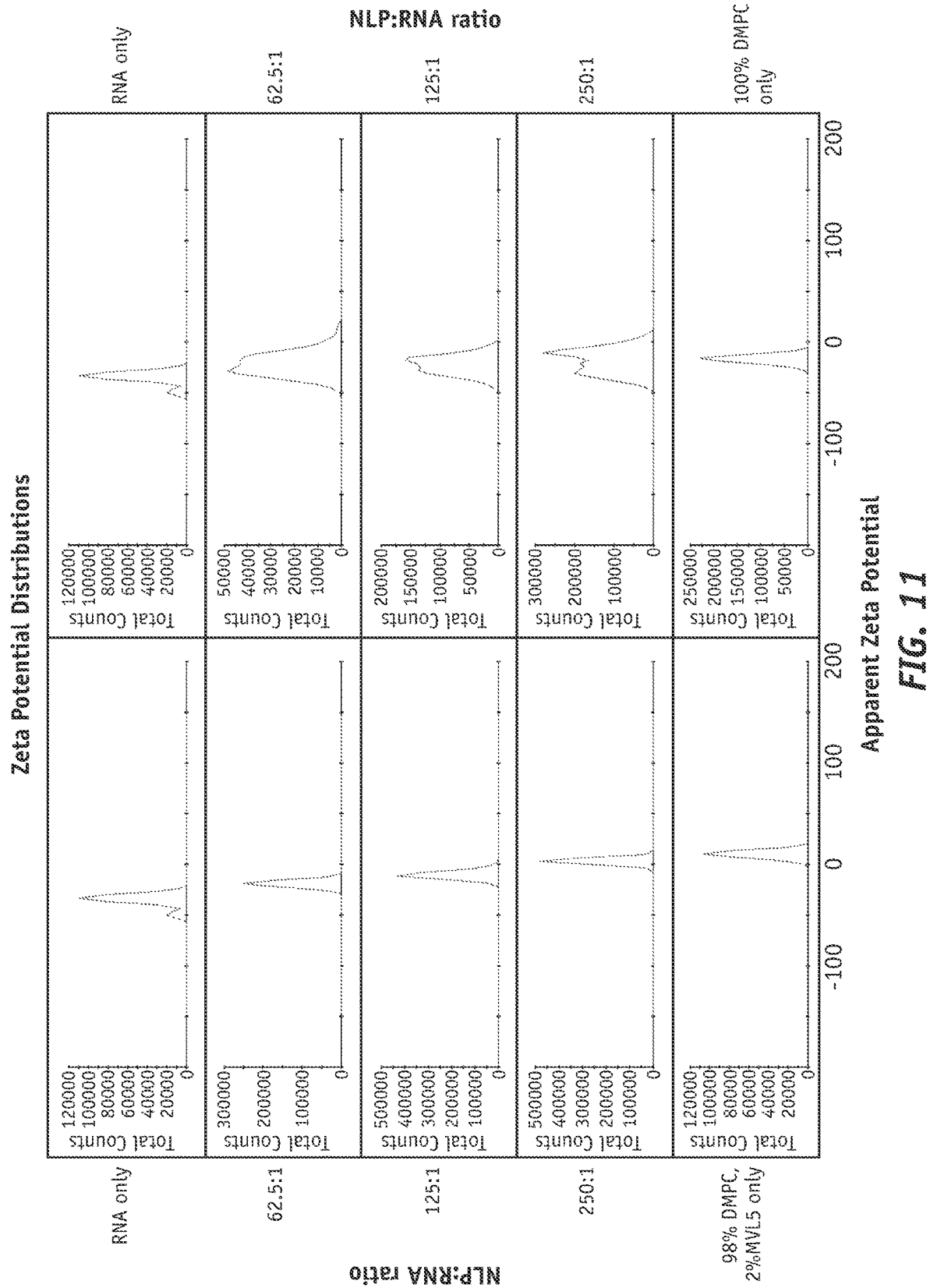
FIG. 11 shows an exemplary zeta potential distribution for a cationic NLP:Replicon complex (98:2 DMPC:MVL5, left panels) and a non-cationic NLP:Replicon mixture (100% DMPC, right panels) at the ratios of NLP:RNA indicated. RNA alone is shown as a control. Scaffold protein ApoE4 was used for both the 100% DMPC example and the 98:2 DMPC:MVL5 example.

FIG. 11 shows a zeta potential distribution for a cationic NLP:Replicon complex (98:2 DMPC:MVL5, left panels) and a non-cationic NLP:Replicon mixture (100% DMPC, right panels) at the ratios of NLP:RNA indicated on the y-axis. RNA alone is shown as a control.

In the case of the non-cationic NLP:Replicon mixture (right panels), the 100% DMPC non-cationic NLPs form two distinct structures when complexed with RNA at increasing NLP:RNA ratios. The leftmost peak corresponds to the free replicon, whereas the rightmost peak is the free DMPC NLP. However, with cationic NLP:Replicon complexes, a single peak distribution was visualized throughout all the ratios tested. This phenomenon validates that cationic NLPs form stable units with RNA replicon that could not be reproduced with non-cationic charged NLPs.

Example 5: Dynamic Light Scattering In Vitro Assessment of Cationic-NLP:Replicon Complexes The particle size of the complex was measured using dynamic light scattering (DLS). The cationic-NLP has a size of about 13-15 nm (±1 nm, and the replicon alone has a size of about 50 nm (±10 nm. As shown in FIG. 12, the cationic-NLP:Replicon complex size varied between 90 nm and 558 nm depending on the type of cationic NLP used. When complexed with RNA, cationic NLPs form much larger structures than NLP alone. In contrast, the 100% DMPC NLP does not display a dramatic size increase when mixed with RNA.

Example 6: Dye Exclusion In Vitro Assessment Of Formation of Cationic-NLP:Replicon Complexes An dye exclusion analysis was performed to access whether the cationic-NLP:replicon complexes protect the RNA replicon from small dye molecules. The cationic-NLP:Replicon association was assessed by measuring the level of fluorescence of cationic-NLP:Replicon after incubation with a fluorescent RNA-binding dye.

FIG. 13 shows a graph of results of dye exclusion analysis of NLP:Replicon ratio, measured in relative fluorescence units. Results are shown for NLP complexes comprising 100% DMPC (triangle), or NLP comprising DMPC with 10% DDAB (circle), or DMPC with 5% MVL5 (square).

Small dye molecules exhibit enhanced fluorescence once they intercalate between adjacent bases in the nucleic acid molecule. When associated with cationic-NLP, the RNA replicon becomes less accessible to small dye molecules, resulting in lower fluorescence. Less fluorescence was observed at higher NLP to replicon ratios. Specifically, NLPs formulated with 90:10 (DMPC:DDAB) or 95:5 (DMPC:MVL5) cationic lipids blocked most dye molecules from binding to RNA between a 250:1 and 500:1 cationic NLP:Replicon ratio. In contrast, non-cationic 100% DMPC lipids intercalated dye molecules at a relatively consistent rate despite NLP:Replicon ratio. The results suggest that cationic NLPs formulated with RNA replicon decrease dye intercalation at higher NLP:RNA ratios, whereas non-cationic NLPs, such as those comprising DMPC alone, are not affected by the NLP:RNA ratio.

Example 7: Rnase Protection In Vitro Assessment of Cationic-NLP:Replicon Complexes The effect of cationic-NLP association on stabilization of the RNA and protection from RNase degradation was assessed in this example. RNA molecules are formulated with increasing amounts of NLP and incubated with RNase. The amount of degradation or protection can be assessed using agarose gel electrophoresis or PCR.

Figure 14:
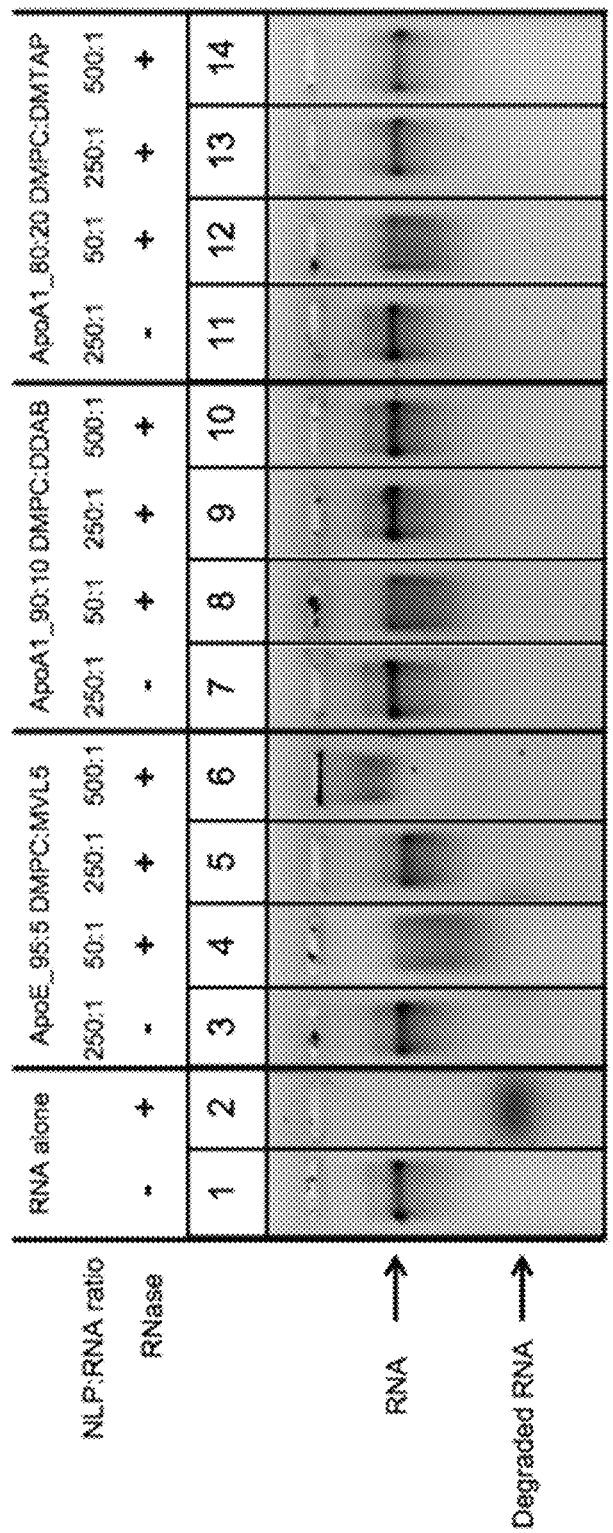
FIG. 14 shows images of gel electrophoresis results of migration patterns of RNA formulated with cationic-NLP, with (+) or without (−) RNase treatment. Each sample contains 1% triton X100 to disintegrate the NLPs and release replicon. In lane 6, the RNA migration may be affected by the highly charged cationic lipid, MVL5, which slowed RNA migration out of the well at a 500:1 ratio. DMPC with 5% MVL5 was made with ApoE4 scaffold protein. Cationic-NLPs comprised of DMPC with 10% DDAB, and DMPC with 20% DMTAP are made with ApoA1 scaffold protein. 0.1 µg RNA is loaded per lane. RNA alone is shown as a control.

FIG. 14 shows images of gel electrophoresis results of migration patterns of RNA formulated with cationic-NLP, with (+) or without (−) RNase treatment. Each sample contains 1% triton X100 to disintegrate the NLPs and release replicon. In lane 6, the RNA migration may be affected by the highly charged cationic lipid, MVL5, which slowed RNA migration out of the well at a 500:1 ratio. 0.1 µg RNA is loaded per lane. RNA alone is shown as a control.

Figure 15:
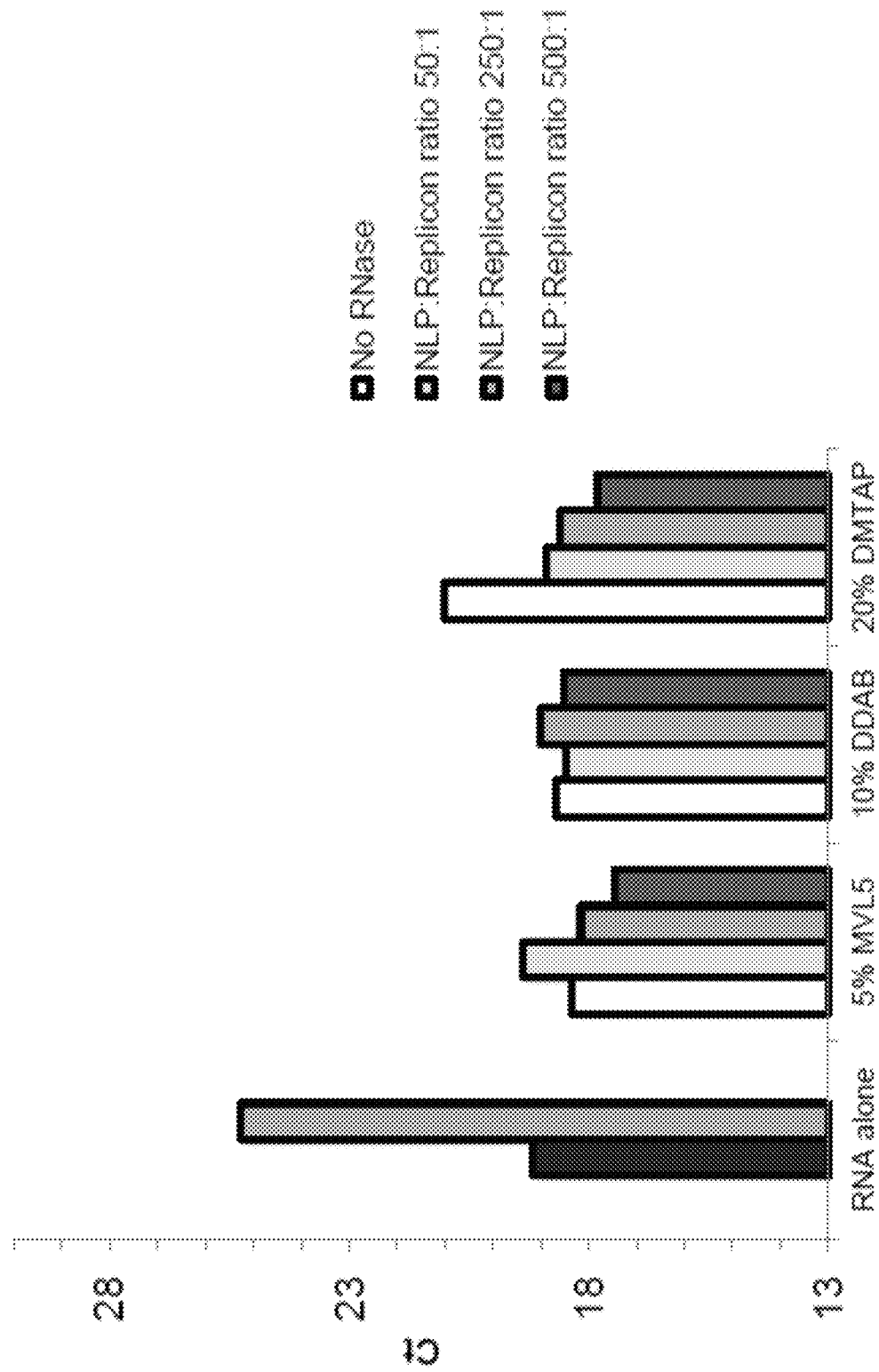
FIG. 15 shows a graph of RT-PCR cycle threshold (Ct) results for exemplary NLPs formulated with RNA replicon at varying NLP:Replicon molar ratios. As a control, RNA alone (unformulated with NLP) was treated with RNase (gray bar) or without RNase (black bar). Each sample contains 5 ng of RNA. DMPC with 5% MVL5 was formulated with ApoE4 scaffold protein. DMPC with 10% DDAB, and DMPC with 20% DMTAP were formulated with ApoA1 scaffold protein.

FIG. 15 shows a graph of RT-PCR cycle threshold (Ct) results for NLPs formulated with RNA replicon at varying NLP:Replicon molar ratios. As a control, RNA alone (unformulated with NLP) was treated with RNase (gray bar) or without RNase (black bar). Each sample contains 5 ng of RNA.

The results shown in FIG. 14 and FIG. 15 indicate that upon RNase treatment, the naked RNA is completely degraded. However, when RNA is complexed with cationic charged NLPs, the degradation of RNA was diminished. It is also noted that with more NLP complexed to replicon, the RNA received better protection from RNase.

Example 8: Luciferase Activity In Vivo Assessment of Cationic-NLP:Replicon Complexes To study the in vivo transfection efficiency of the cationic NLP:replicon complexes, a replicon with a firefly luciferase reporter gene was used. If delivered into the cytosol of a cell, this RNA molecule produces many copies of the luciferase protein. Upon injection of the luciferase substrate (luciferin), the relative expression levels of the protein in mice can be imaged in vivo using a bioluminescence imager. The amount of bioluminescence signal can be used as a surrogate for expression levels and the efficiency of the RNA delivery.

Figure 16:
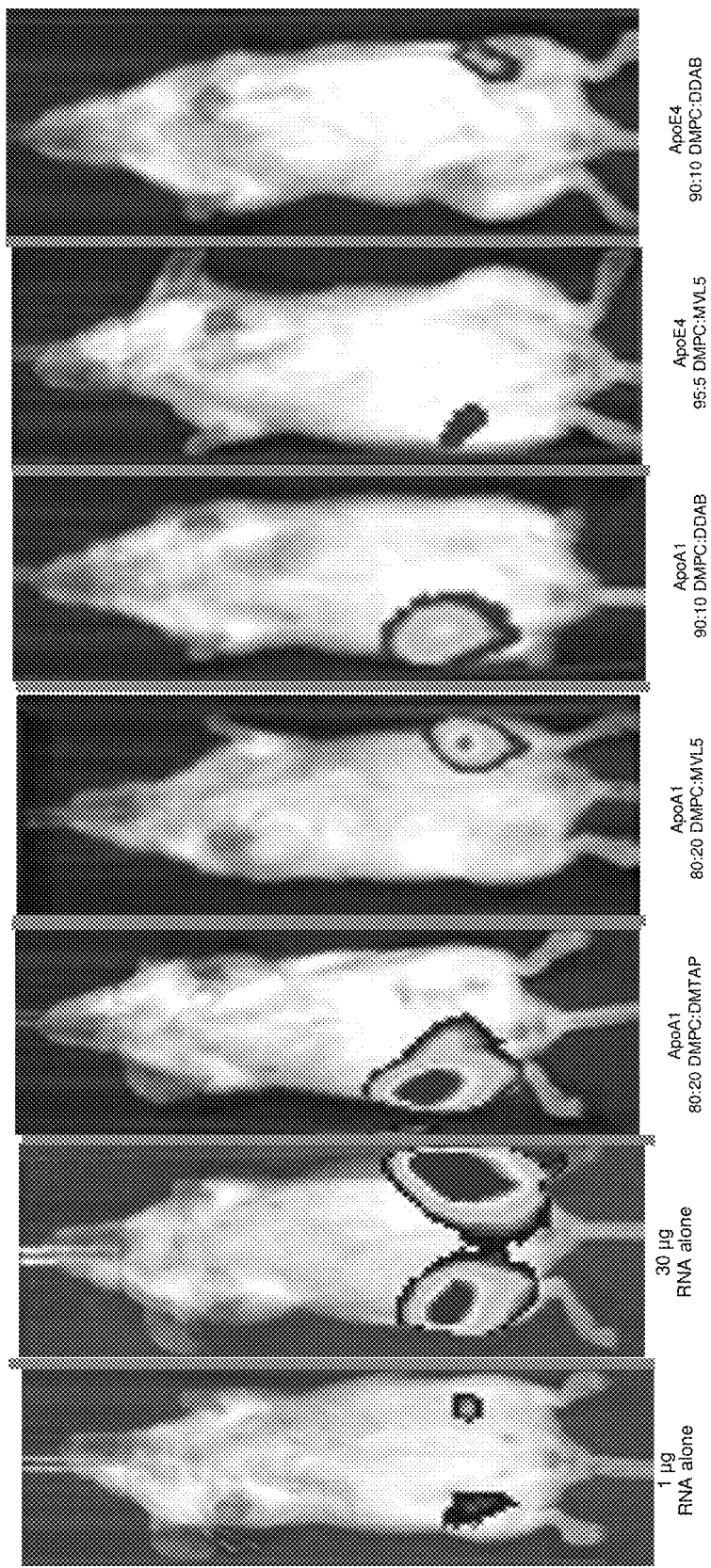
FIG. 16 shows exemplary images of bioluminescence levels 4 to 5 days after mice were injected intramuscularly with cationic-NLP:Replicon expressing luciferase, or unformulated replicon RNA expressing luciferase (without cationic-NLP). Images are shown of mice that received either unformulated RNA replicon (1 µg or 30 µg), or cationic-NLP:Replicon comprising 80:20 DMPC:DMTAP, 80:20 DMPC:DMTAP plus 20% GMO, 80:20 DMPC:MVL5, 90:10 DMPC:DDAB, or 95:5 DMPC:MVL5. All cationic NLP formulations were injected with 1 µg RNA replicon. 1 µg RNA alone and 30 µg RNA alone are used as controls. The scaffold proteins ApoA1 or ApoE4 have been used as indicated on the figure.
Figure 17:
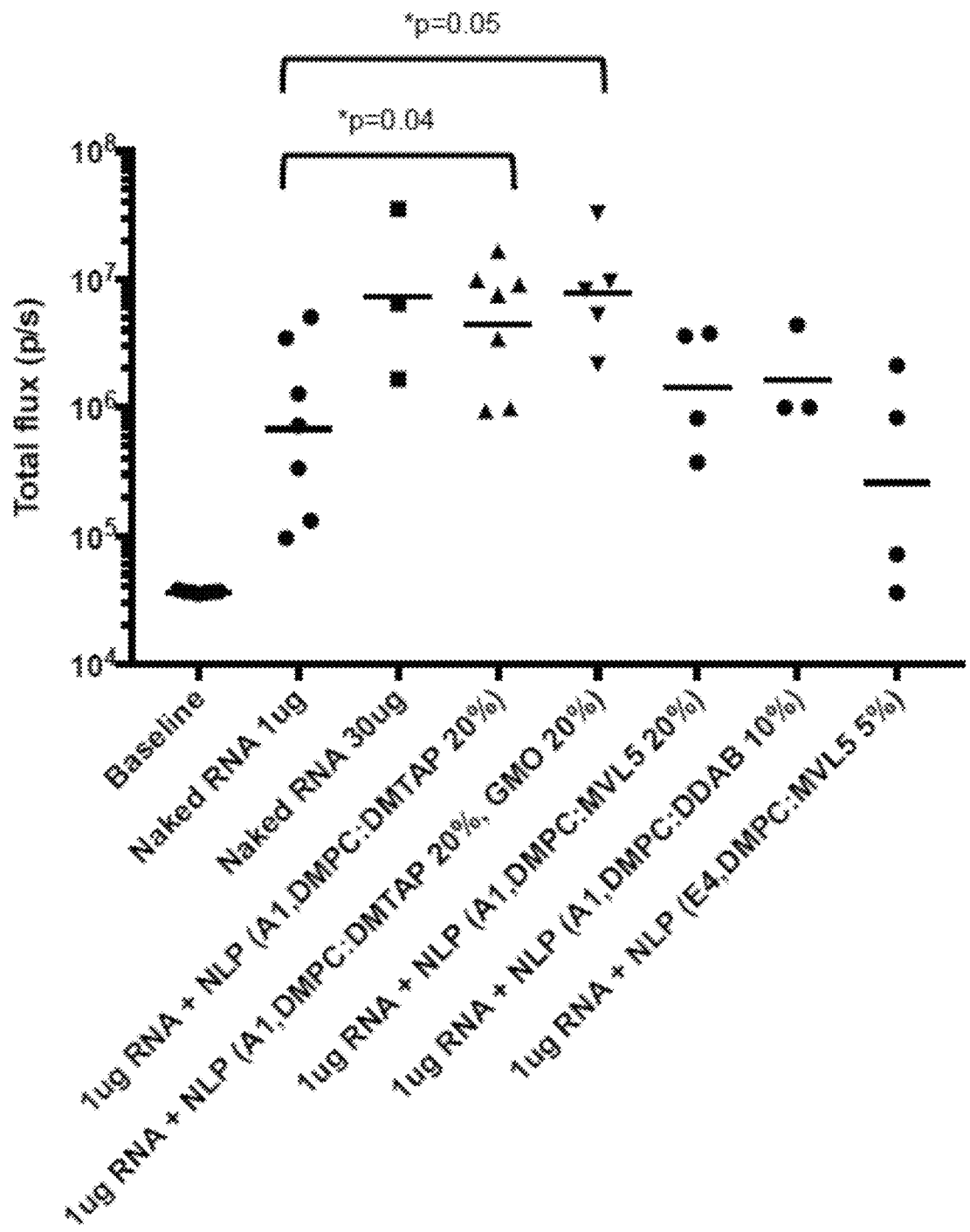
FIG. 17 shows an exemplary graph of in vivo luciferase activity, assessed by bioluminescence (maximum total flux in photons per second, p/s) in groups of female BALB/c mice injected intramuscularly with either unformulated replicon RNA expressing luciferase (without cationic-NLP) at doses of 1 µg or 30 µg, or 1 µg RNA formulated with various cationic NLPs. A baseline control depicts mice that did not show any bioluminescent signal. The top cationic NLPs formulated with 1 µg RNA showed comparable bioluminescence to 30 µg naked RNA control. All NLP:Replicon formulations are at a 250:1 (NLP:RNA) molar ratio, except (A1, DMPC, DMTAP 20%, GMO 20%) which was formulated at a 50:1 (NLP:RNA) molar ratio. Each dot represents one mouse. P-values indicate significant differences between the groups indicated. A1 and E4 indicate ApoA1 and ApoE4 protein scaffolds, respectively. Naked RNA indicates RNA alone, unformulated with NLPs.

The bioluminescence was measured 4-5 days after a single bilateral i.m. injection containing a dose of 1µg RNA replicon complexed with various NLP formulations. A bilateral i.m. injection of 1µg and 30 µg naked RNA (unformulated with NLP) was carried out as a control. Different cationic lipid NLP formulations displayed large differences in bioluminescence intensity. Some formulations that resulted in the highest bioluminescence are shown in FIG. 16 and FIG. 17.

Mice that were injected with RNA formulated with NLPs composed of 80% DMPC bulk lipid, 20% DMTAP cationic lipid at a 250:1 (NLP:RNA) molar ratio displayed a high bioluminescence signal. In another top candidate formulation, the NLPs were formulated with 80% DMPC bulk lipid, 20% DMTAP cationic lipid, and 20% monoolein (GMO) additive at a 50:1 (NLP:RNA) molar ratio. Both of the top formulations were made with apoA1 scaffold protein. Using 1 µg of RNA, the top two NLP formulations display comparable bioluminescence to 30 µg naked RNA control. DMTAP formulations showed the strongest formulated NLP signal in vivo.

Other cationic lipid formulations also displayed relatively high bioluminescence, but luciferase signal was considerably less than the DMTAP formulations. Interestingly, NLPs formulated with 80:20 (DMPC:MVL5) and 90:10 (DMPC:DDAB) formed clean, homogeneous NLP peaks by SEC, similar to what was seen with the top DMTAP formulations. However, MVL5 and DDAB formulations did not perform as well in vivo as shown in FIG. 17.

Example 9: Luciferase Activity In Vivo Assessment of Formation of Telo-Cationic-NLP:Replicon Complexes Telo-cationic-NLPs can be synthesized in a similar way as the cationic-NLPs, with the exception that telodendrimer is present during the assembly process. The formulation of Telo-cationic-NLPs is similar to cationic-NLP as described in Example 1, whereby the telodendrimer is added to the assembly mixture (with the solubilized lipids and scaffold protein) prior to surfactant removal.

The effect of telodendrimer on the in vivo transfection efficiency of the cationic NLP:replicon complexes was investigated using the bioluminescence assay described in Example 8.

In particular, teledendrimer were first added to two of the top-performing cationic-NLPs formulation (apoA1 DMPC:DMTAP 20% and apoA1 DMPC:DMTAP 20% GMO 20%). Two different telodendrimers were explored: 5KCA8 and cys-5KCA8 (at 0.1% and 1%, respectively). Four resulting formulations were tested for the in vivo luciferase intensity, as follows:

apoA1, DMPC:20% DMTAP+0.1% 5KCA8 telodendrimer
apoA1, DMPC:20% DMTAP, 20% GMO+1% cys-5KCA8 telodendrimer
apoA1, DMPC:20% DMTAP
apoA1, DMPC:20% DMTAP, 20% GMO The above study was duplicated to provide additional data points to increase the statistical significant of the analysis.

Figure 18:
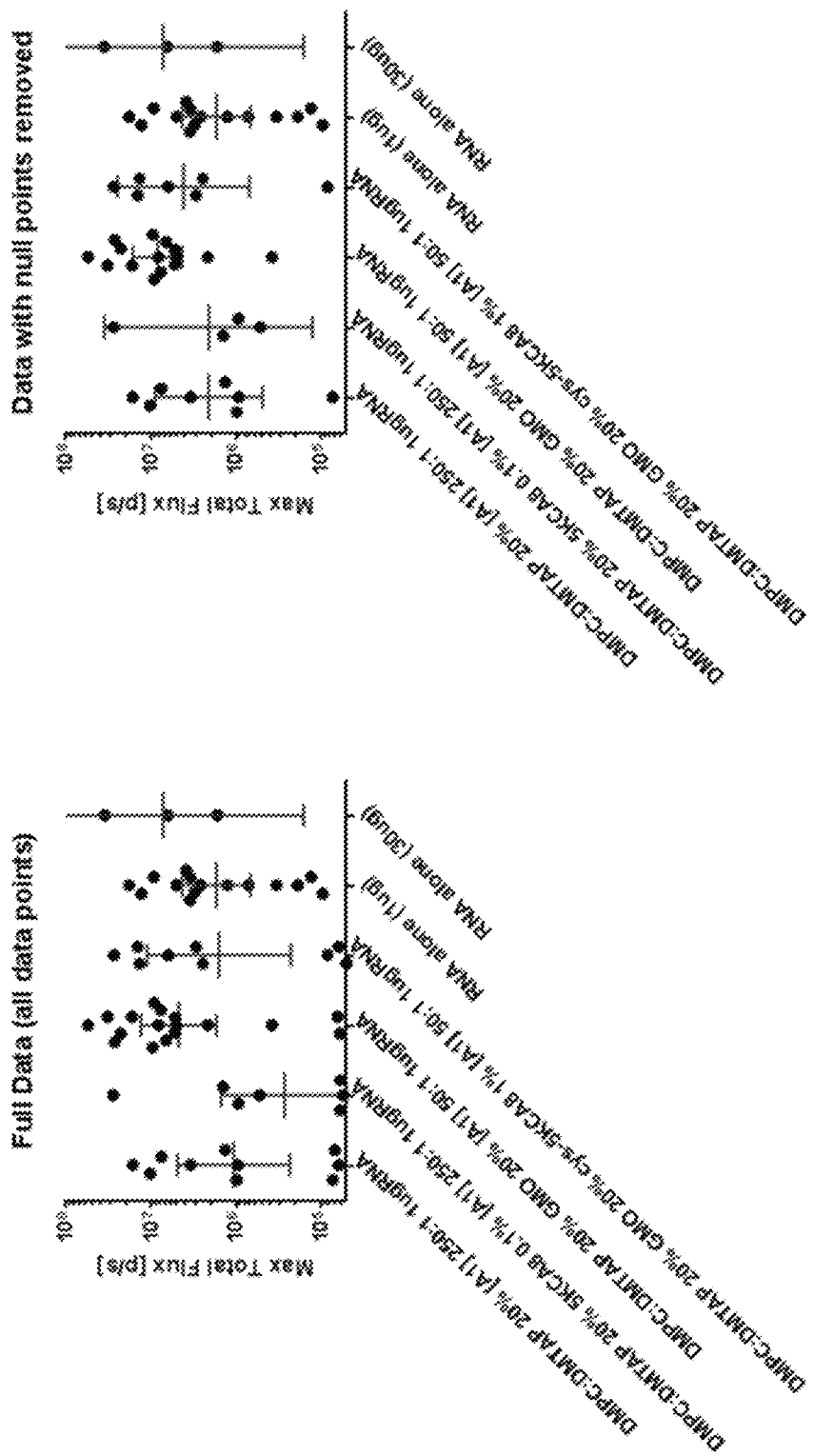
FIG. 18 shows exemplary graphs of in vivo luciferase intensity of RNA replicons formulated with cationic NLPs, cationic telo-NLPs, and RNA alone. Each data point represents maximal total flux from a single animal. Full data sets (left graph) contains all data points, even when no signal is detected (presumably from variability in administration). Removing null data points (right graph) illustrates effect of formulation if successfully administered. Bars indicated geometric mean with 95% confidence intervals.

FIGS. 18A and B summarize the in vivo luciferase intensity of RNA replicons formulated with cationic NLPs, cationic telo-NLPs, and RNA alone. Each data point represents maximal total flux from a single animal. Full data sets (left graph) contains all data points, even when no signal is detected (presumably from variability in administration). Removing null data points (right graph) illustrates effect of formulation if successfully administered. Bars indicated geometric mean with 95% confidence intervals. After initial screens, limited enhancement was observed using the telodendrimer in the two top performing cationic-NLPs, as shown in FIG. 18.

While no dramatic enhancement was observed through the addition of telodendrimer to the above NLPs formulations, it was investigated next whether adding telodendrimer to less effective cationic-NLP formulations would show greater enhancement.

Six NLP formulations from previous screens with different efficacy varying from low efficacy to high efficacy are chosen. These six NLP formulations are binned into three categories, based on their in vivo efficacy, as follows:

High efficacy group: apoA1, DMPC, DDAB (10%)
    apoE4, DMPC, DODAP (30%)
Medium efficacy group: apoE4, DMPC, MVL5 (2%)
    apoE4, DMPC, MVL5 (5%)
Low efficacy group: apoA1, DMPC, DMEPC (40%)
    apoA1, DMPC, DOPE (20%) DODAP (20%)

Figure 20A:
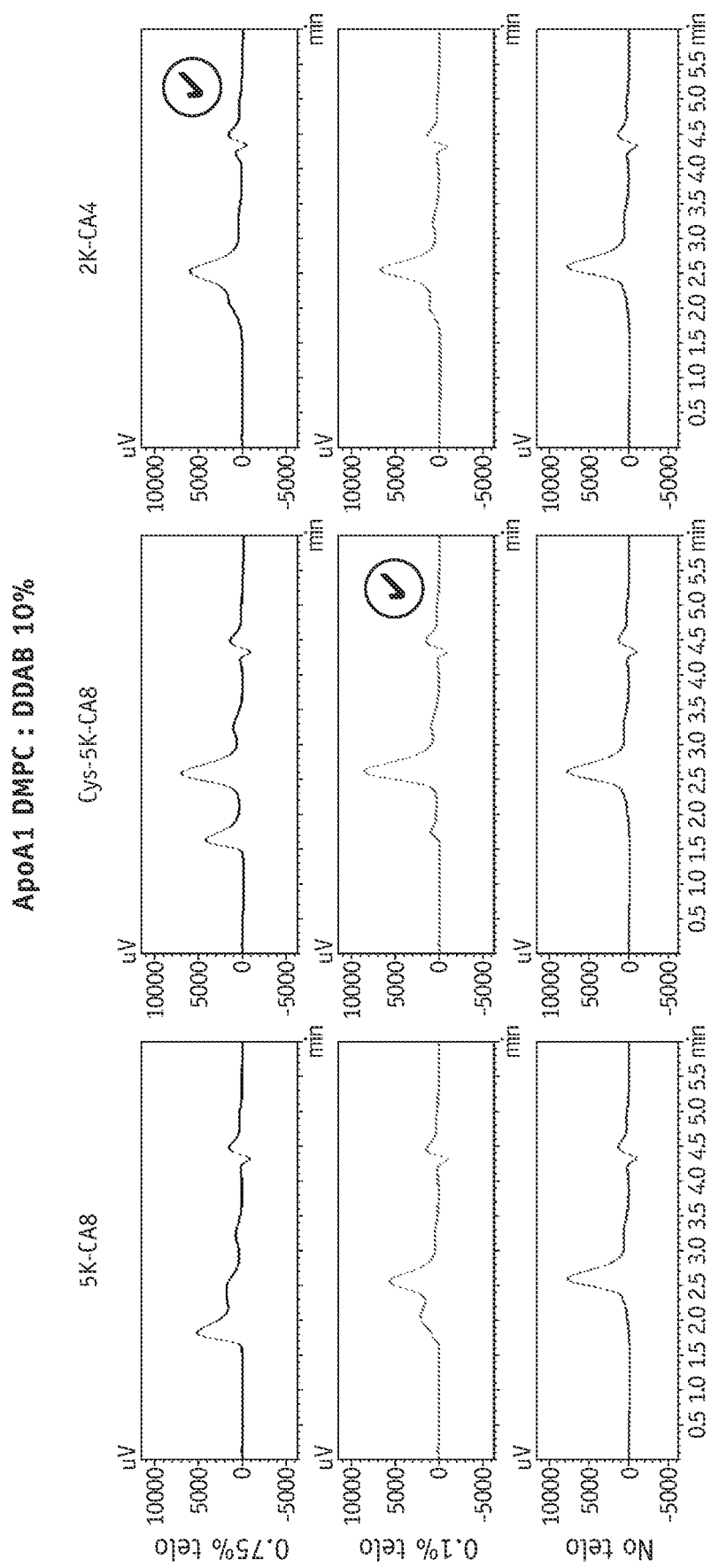
FIGS. 20A-20C shows exemplary results of a SEC screen of NLP formation upon additional of increasing ratios of three different telodendrimers.
Figure 20B:
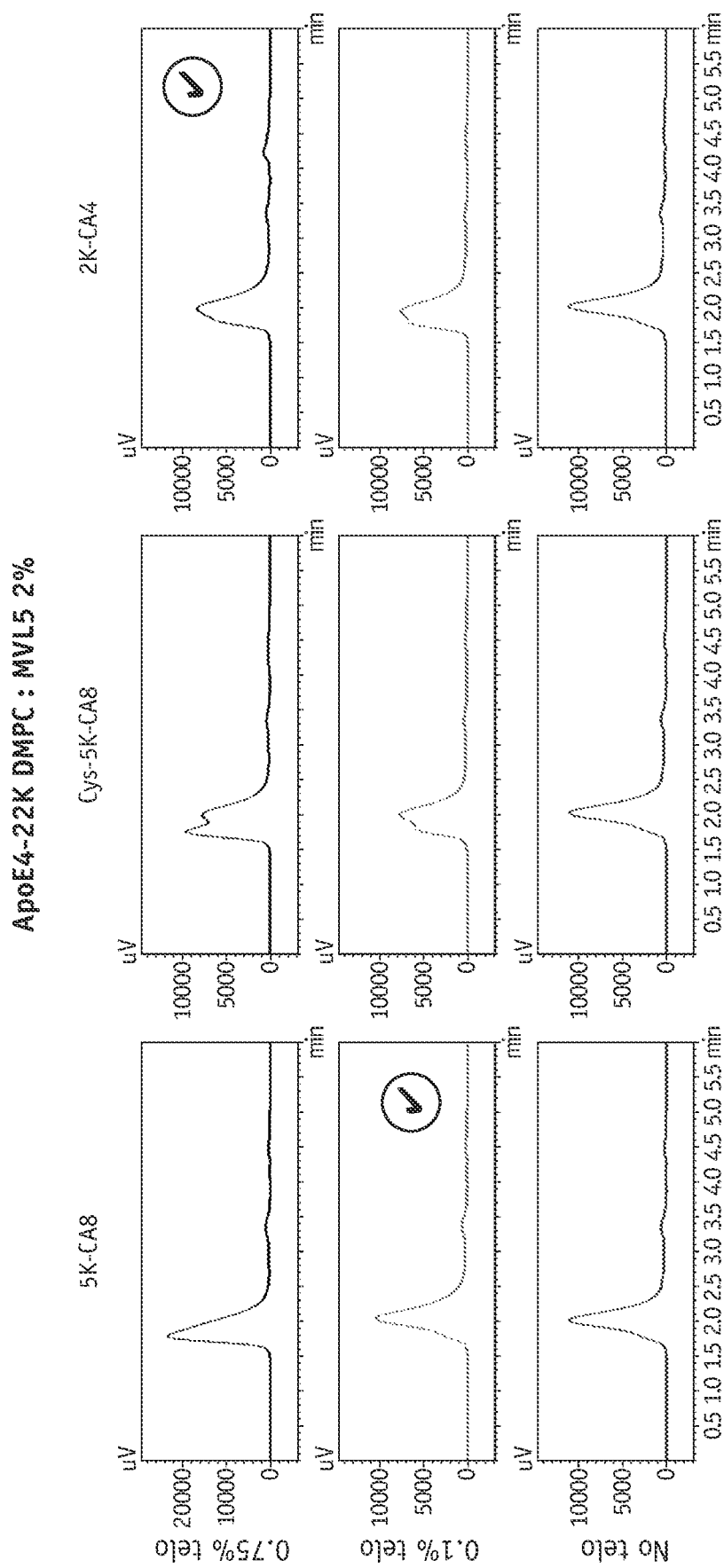
Figure 20C:
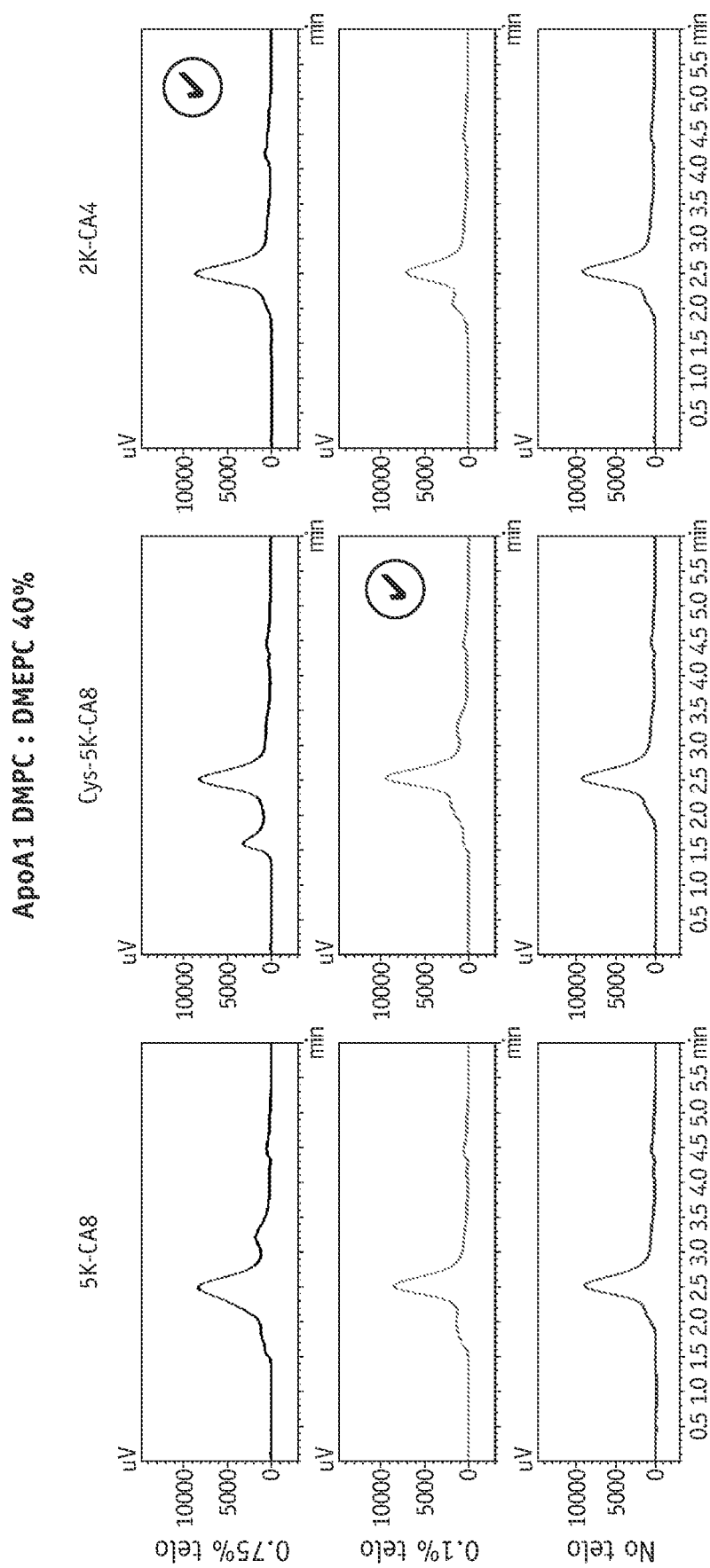

These NLPs were then formulated with the following telodendrimers at the indicated ratios:
    0%, 0.1%, 0.75% 5KCA8 telodendrimer
    0%, 0.1%, 0.75% 2KCA8 telodendrimer
    0%, 0.1%, 0.75% cys-5KCA8 telodendrimer FIGS. 20A-C show the screen of NLP formation by SEC upon additional of increasing ratios of three different telodendrimers. These telodendrimers were tested with cationic NLPs binned into high efficacy (A), medium efficacy (B), or low efficacy (C), based on previous in vivo assessments of luciferase intensity. SEC traces (plotting absorbance intensity as a function of retention time) were used to identify those formulations that formed the most homogeneous species of NLPs, based on the presence of a single SEC peak. Formulations chosen for subsequent in vivo testing are marked with red check.

Figure 19:
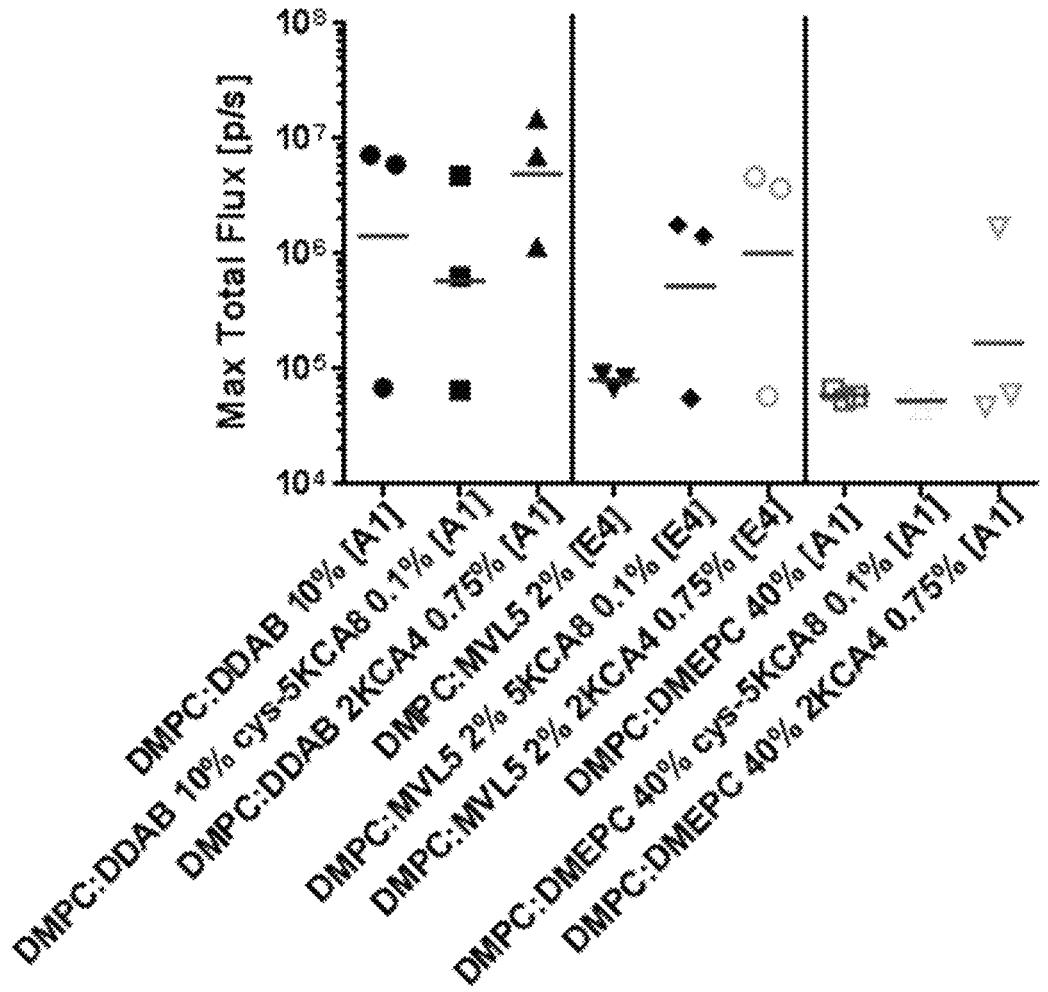
FIG. 19 shows an exemplary graph of in vivo luciferase intensity of RNA replicons formulated with NLPs categorized in low, medium, and high efficacy classes. Each data point represents maximal total flux from a single animal. Bars indicated geometric mean.

FIG. 19 summarizes in vivo luciferase intensity of RNA replicons formulated with NLPs categorized in high, medium, and low efficacy classes. No enhanced luciferase activity was observed by including telodendrimers to high efficacy NLPs (DMPC:DDAB 10% [A1]). Some enhanced luciferase activity is observed in the medium efficacy class (DMPC:MVL5 2% [E4]) upon the addition of either 5KCA8 (0.1%) or 2KCA4 (0.75%) telodendrimer. No significant enhancement in luciferase activity is observed in the low efficacy class (DMPC:DMEPC 40% [E4]) upon the addition of telodendrimer. Each data point represents maximal total flux from a single animal. Bars indicated geometric mean.

The results suggest that addition of telodendrimer appears to enhance luciferase signal compared to non-telo formulations. The overall effect is telo- and NLP-dependent. The greatest improvement was with the medium efficacy group, where only telodendrimer-based formulations elicited significant luciferase activity.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified NLPs and related uses to additional NLPs formed by other cationic lipids, membrane forming lipids, scaffold proteins, additives, and possibly functionalized amphipathic compounds and membrane proteins according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

Although the invention has been described with reference to the above examples, it will be understood that modifications and variations are encompassed within the spirit and scope of the invention. Accordingly, the invention is limited only by the following claims.

REFERENCES

1. Fischer, N. O., et al., *Evaluation of Nanolipoprotein Particles (NLPs) as an In Vivo Delivery Platform.* PLoS ONE, 2014. 9(3): p. e93342.
2. Blanchette, C. D., et al., *Kinetic Analysis of His-Tagged Protein Binding to Nickel-Chelating Nanolipoprotein Particles.* Bioconjugate Chemistry, 2010. 21(7): p. 1321-1330.
3. Fischer, N. O., et al., *Colocalized Delivery of Adjuvant and Antigen Using Nanolipoprotein Particles Enhances the Immune Response to Recombinant Antigens.* Journal of the American Chemical Society, 2013. 135(6): p. 2044-2047.
4. Shih, A. Y., et al., *Disassembly of nanodiscs with cholate.* Nano Letters, 2007. 7(6): p. 1692-1696.
5. Chromy, B. A., et al., *Different apolipoproteins impact nanolipoprotein particle formation.* Journal of the American Chemical Society, 2007. 129(46): p. 14348-14354.
6. Blanchette, C. D., et al., *Characterization and Purification of Polydisperse Reconstituted Lipoproteins and Nanolipoprotein Particles.* International Journal of Molecular Sciences, 2009. 10(7): p. 2958-2971.
7. CHROMY, B. A., NANOLIPOPROTEIN PARTICLES AND RELATED METHODS AND SYSTEMS FOR PROTEIN CAPTURE, SOLUBILIZATION, AND/OR PURIFICATION in US 2009-0192299 A1 2009: US.
8. Cappuccio, J. A., et al., *Cell-free Co-expression of Functional Membrane Proteins and Apolipoprotein, Forming Soluble Nanolipoprotein Particles.* Molecular & Cellular Proteomics, 2008. 7(11): p. 2246-2253.

9. Gao, T. J., et al., *Characterizing diffusion dynamics of a membrane protein associated with nanolipoprotein using fluorescence correlation spectroscopy.* Protein Science, 2011. 20(2): p. 437-447.
10. Katzen, F., et al., *Insertion of membrane proteins into discoidal membranes using a cell-free protein expression approach.* Journal of Proteome Research, 2008. 7(8): p. 3535-3542.
11. Coleman, M. A., METHODS AND SYSTEMS FOR PRODUCING NANOLIPOPROTEIN PARTICLES, in US 2011-0059549 A1 2008: US.
12. Georger, J. H., et al., *Helical and Tubular Microstructures Formed by Polymerizable Phosphatidylcholines.* J Am Chem Soc, 1987. 109(20): p. 6169-6175.
13. Morigaki, K., et al., *Surface Functionalization of a Polymeric Lipid Bilayer for Coupling a Model Biological Membrane with Molecules, Cells, and Microstructures.* Langmuir, 2013. 29(8): p. 2722-2730.
14. Regen, S. L., et al., *Polymerized Phosphatidyl Choline Vesicles—Stabilized and Controllable Time-Release Carriers.* Biochemical and Biophysical Research Communications, 1981. 101(1): p. 131-136.
15. Bolikal, D. and S. L. Regen, *Degree of Polymerization of a Vesicle Membrane.* Macromolecules, 1984. 17(6): p. 1287-1289.
16. Lei, J. T. and D. F. Obrien, *2-Dimensional Polymerization of Lipid Bilayers—Rate of Polymerization of Acryloyl and Methacryloyl Lipids.* Macromolecules, 1994. 27(6): p. 1381-1388.
17. Sells, T. D. and D. F. Obrien, *2-Dimensional Polymerization of Lipid Bilayers—Degree of Polymerization of Acryloyl Lipids.* Macromolecules, 1994. 27(1): p. 226-233.
18. Lamparski, H. and D. F. Obrien, *2-Dimensional Polymerization of Lipid Bilayers—Degree of Polymerization of Sorbyl Lipids.* Macromolecules, 1995. 28(6): p. 1786-1794.
19. Tsuchida, E., et al., *Polymerization of Unsaturated Phospholipids as Large Unilamellar Liposomes at Low-Temperature.* Macromolecules, 1992. 25(1): p. 207-212.
20. Ohno, H., Y. Ogata, and E. Tsuchida, *Polymerization of Liposomes Composed of Diene-Containing Lipids by Uv and Radical Initiators—Evidence for the Different Chemical Environment of Diene Groups on 1-Acyl and 2-Acyl Chains.* Macromolecules, 1987. 20(5): p. 929-933.
21. Serrano, J., et al., *Polymerized Surfactant Vesicles— Determinations of Rates and Degrees of Polymerization in Vesicles Prepared from Styrene-Containing Surfactants.* Macromolecules, 1985. 18(10): p. 1999-2005.
22. Lieser, G., B. Tieke, and G. Wegner, *Structure, Phase-Transitions and Polymerizability of Multilayers of Some Diacetylene Monocarboxylic Acids.* Thin Solid Films, 1980. 68(1): p. 77-90.
23. Johnston, D. S., et al., *Phospholipid polymers—synthesis and spectral characteristics.* Biochim Biophys Acta, 1980. 602(1): p. 57-69.
24. Kim, J. M., et al., *Immobilized polydiacetylene vesicles on solid substrates for use as chemosensors.* Advanced Materials, 2003. 15(13): p. 1118-1121.
25. Hayward, J. A. and D. Chapman, *Biomembrane surfaces as models for polymer design: the potential for haemocompatibility.* Biomaterials, 1984. 5(3): p. 135-42.
26. Regen, S. L., et al., *Polymerized phosphatidyl choline vesicles. Stabilized and controllable time-release carriers.* Biochem Biophys Res Commun, 1981. 101(1): p. 131-6.
27. Yavlovich, A., et al., *A novel class of photo-triggerable liposomes containing DPPC:DC8,9PC as vehicles for delivery of doxorubcin to cells.* Biochimica Et Biophysica Acta-Biomembranes, 2011. 1808(1): p. 117-126.
28. Tieke, B., G. Lieser, and G. Wegner, *Polymerization of diacetylenes in multilayers.* Journal of Polymer Science: Polymer Chemistry Edition, 1979. 17(6): p. 1631-1644.
29. Baughman, R. H., *Solid-state polymerization of diacetylenes.* Journal of Applied Physics, 1972. 43(11): p. 4362-4370.
30. Weilhammer, D. R., et al., *The use of nanolipoprotein particles to enhance the immunostimulatory properties of innate immune agonists against lethal influenza challenge.* Biomaterials, 2013. 34(38): p. 10305-18.
31. Wang, S., D. Q. Peng, and Y. Yi, *The unsolved mystery of apoA-I recycling in adipocyte.* Lipids Health Dis, 2016. 15: p. 35.
32. Vickers, K. C., et al., *MicroRNAs are transported in plasma and delivered to recipient cells by high-density lipoproteins.* Nat Cell Biol, 2011. 13(4): p. 423-33.
33. Coleman, M. A., et al., *Expression and Association of the Yersinia pestis Translocon Proteins, YopB and YopD, Are Facilitated by Nanolipoprotein Particles.* PLoS One, 2016. 11(3): p. e0150166.
34. He, W., et al., *Cell-free expression of functional receptor tyrosine kinases.* Sci Rep, 2015. 5: p. 12896.
35. Tufteland, M., G. Ren, and R. Ryan, *Nanodisks derived from amphotericin B lipid complex.* Journal of Pharmaceutical Sciences, 2008. 97(10): p. 4425-4432.
36. Yuan, Y., et al., *Delivery of hydrophilic drug doxorubicin hydrochloride-targeted liver using apoA1 as carrier.* J Drug Target, 2013. 21(4): p. 367-374.
37. Ding, Y., et al., *A biomimetic nanovector-mediated targeted cholesterol-conjugated siRNA delivery for tumor gene therapy.* Biomaterials, 2012. 33(34): p. 8893-8905.
38. Frias, J. C., et al., *Properties of a versatile nanoparticle platform contrast agent to image and characterize atherosclerotic plaques by magnetic resonance imaging.* Nano Lett, 2006. 6(10): p. 2220-2224.
39. Fischer, N. O., et al., *Conjugation to nickel-chelating nanolipoprotein particles increases the potency and efficacy of subunit vaccines to prevent West Nile encephalitis.* Bioconjug Chem, 2010. 21(6): p. 1018-22.
40. Fischer, N. O., et al., *Colocalized delivery of adjuvant and antigen using nanolipoprotein particles enhances the immune response to recombinant antigens.* J Am Chem Soc, 2013. 135(6): p. 2044-7.
41. Bhattacharya, P., et al., *Nanodisc-Incorporated Hemagglutinin Provides Protective Immunity against Influenza Virus Infection.* Journal of Virology, 2010. 84(1): p. 361-371.
42. Allen, T. M. and P. R. Cullis, *Drug delivery systems: entering the mainstream.* Science, 2004. 303(5665): p. 1818-22.
43. Sparreboom, A., et al., *Comparative preclinical and clinical pharmacokinetics of a cremophor-free, nanoparticle albumin-bound paclitaxel (ABI-007) and paclitaxel formulated in Cremophor (Taxol).* Clin Cancer Res, 2005. 11(11): p. 4136-43.

44. Cho, K., et al., *Therapeutic nanoparticles for drug delivery in cancer.* Clinical cancer research, 2008. 14(5): p. 1310-1316.
45. al., A.G.C.e., *Emerging implications of nanotechnology on cancer diagnostics and therapeutics.* Cancer, 2006. 107: p. 8.
46. al., S.M.e., *A concise review of carbon nanotube's toxicology.* Nano Rev. , 2013. 4.
47. Miyazaki, M., et al., *Effect of phospholipid composition on discoidal HDL formation.* Biochimica et Biophysica Acta (BBA)-Biomembranes, 2013. 1828(5): p. 1340-1346.
48. Weilhammer, D. R., et al., *The use of nanolipoprotein particles to enhance the immunostimulatory properties of innate immune agonists against lethal influenza challenge.* Biomaterials, 2013. 34(38): p. 10305-10318.
49. Cappuccio, J. A., et al., *Cell-free co-expression of functional membrane proteins and apolipoprotein, forming soluble nanolipoprotein particles.* Molecular & Cellular Proteomics, 2008. 7(11): p. 2246-2253.
50. Cappuccio, J. A., et al., *Cell-free expression for nanolipoprotein particles: building a high-throughput membrane protein solubility platform, in High throughput protein expression and purification.* 2009, Springer. p. 273-295.
51. Blanchette, C. D., et al., *Atomic force microscopy differentiates discrete size distributions between membrane protein containing and empty nanolipoprotein particles.* Biochimica et Biophysica Acta (BBA)-Biomembranes, 2009. 1788(3): p. 724-731.
52. Wadsater, M., et al., *Monitoring shifts in the conformation equilibrium of the membrane protein cytochrome P450 reductase (POR) in nanodiscs.* Journal of Biological Chemistry, 2012. 287(41): p. 34596-34603.
53. Justesen, B. H., et al., *Isolation of monodisperse nanodisc-reconstituted membrane proteins using free flow electrophoresis.* Analytical chemistry, 2013. 85(7): p. 3497-3500.
54. Baylon, J. L., et al., *Characterizing the membrane-bound state of cytochrome P450 3A4: structure, depth of insertion, and orientation.* Journal of the American Chemical Society, 2013. 135(23): p. 8542-8551.
55. Gao, T., et al., *Characterization of De Novo Synthesized GPCRs Supported in Nanolipoprotein Discs.* PLoS ONE, 2012. 7(9): p. e44911.
56. Akkaladevi, N., et al., *Assembly of anthrax toxin pore: Lethal-factor complexes into lipid nanodiscs.* Protein Science, 2013. 22(4): p. 492-501.
57. Tufteland, M., et al., *Peptide stabilized amphotericin B nanodisks.* Peptides, 2007. 28(4): p. 741-746.
58. Jia, J., et al., *Preparation, characterizations, and in vitro metabolic processes of paclitaxel-loaded discoidal recombinant high-density lipoproteins.* Journal of Pharmaceutical Sciences, 2012. 101(8): p. 2900-2908.
59. Wang, J., et al., *Tumor targeting effects of a novel modified paclitaxel-loaded discoidal mimic high density lipoproteins.* Drug delivery, 2013. 20(8): p. 356-363.
60. Fischer, N. O., et al., *Conjugation to Nickel-Chelating Nanolipoprotein Particles Increases the Potency and Efficacy of Subunit Vaccines to Prevent West Nile Encephalitis.* Bioconjugate Chemistry, 2010. 21(6): p. 1018-1022.
61. Rensen, P. C. N., et al., *Recombinant lipoproteins: lipoprotein-like lipid particles for drug targeting.* Advanced Drug Delivery Reviews, 2001. 47(2-3): p. 251-276.
62. Blanchette, C. D., et al., *Quantifying size distributions of nanolipoprotein particles with single-particle analysis and molecular dynamic simulations.* Journal of Lipid Research, 2008. 49(7): p. 1420-1430.

What is claimed is:

1. A method of producing a nanolipoprotein (NLPs)-polynucleotide complex, the method comprising:
   contacting a polynucleotide having at least 200 bases with a plurality of cationic nanolipoprotein particles, each cationic nanolipoprotein particle comprising one or more cationic lipids and a membrane forming lipid arranged in a discoidal membrane lipid bilayer stabilized by a scaffold protein, the discoidal membrane lipid bilayer having a diameter from 5 to 25 nm,
   the contacting performed to allow binding bewteen the polynucleotide and the nanolipoprotein particles thus providing nanolipoprotein particles loaded with the polynucleotide,
   wherein the polynucleotide having at least 200 bases is, an RNA, or an analog or a fragment thereof.

2. The method of claim 1, further comprising before contacting the polynucleotide with the plurality of nanoparticles,
   contacting one or more membrane forming lipids and one or more cationic lipids with one or more scaffold proteins to provide the plurality of nanolipoprotein particles in which the one or more cationic lipids are comprised within a membrane forming lipid bilayer stabilized by the one or more scaffold proteins.

3. The method of claim 2, wherein the one or more cationic lipids are in a molar concentration of about 1 to about 60 mol %.

4. The method of claim 2, wherein the one or more cationic lipids are in molar concentration of about 5 to about 40 mol %.

5. The method of claim 2, wherein a molar percent ratio between a total lipid comprising the one or more membrane forming lipids and the one or more cationic lipid and the scaffold protein ranges from 20:1 to 240:1.

6. The method of claim 2, wherein the membrane forming lipid is in amount from 99 to 40% and the cationic lipid is in an amount from 1 to 60% with respect to a total lipid concentration.

7. The method of claim 1, wherein the polynucleotide has a number of bases of at least 5,000 bases.

8. The method of claim 1, wherein the polynucleotide has a number of bases from about 10,000 bases to about 15,000 bases.

9. The method of claim 1, wherein the polynucleotide has a number of bases larger than 15,000.

10. The method of claim 1, wherein the polynucleotide is a RNA replicon.

11. A cationic-nanolipoprotein (NLPs)-polynucleotide complex, comprising
    a polynucleotide molecule having at least 200 bases attached to one or more cationic NLPs,
    wherein each cationic NLP comprises one or more cationic lipids and a membrane forming lipid arranged in a discoidal membrane lipid bilayer stabilized by a scaffold protein, the discoidal membrane lipid bilayer having a diameter from 5 to 25 nm, and
    wherein the polynucleotide is, an RNA, or an analog or a fragment thereof.

12. The cationic NLPs polynucleotide complex of claim 11, wherein the cationic NLP is a plurality of cationic NLPs.

13. The cationic NLPs polynucleotide complex of claim 11, wherein the polynucleotide has a number of bases of at least 5,000 bases.

14. The cationic-NLPspolynucleotide-complex of claim 11 wherein the polynucleotide has a number of bases from about 10,000 bases to about 15,000 bases.

15. The cationic-NLPs-polynucleotide-complex of claim 11, wherein the polynucleotide has a number of bases larger than 15,000.

16. The cationic-NLPs-polynucleotide-complex of claim 11, wherein the polynucleotide is an RNA replicon.

17. The cationic-NLPs-polynucleotide-complex of claim 11, further comprising an adjuvant, a functional polymer, a membrane-associated protein for targeted delivery, one or more additive, one or more telodendrimers, or a combination thereof.

18. A method of delivering a polynucleotide to a target environment, the comprising
contacting the target environment with the cationic-nanolipoprotein (NLPs)-polynucleotide complex of claim 11.

19. The method of claim 18, wherein the target environment in a cell or a tissue.

20. A method of delivering a polynucleotide to a subject, the method comprising
administering to the subject the cationic nanolipoprotein (NLPs)-polynucleotide complex of claim 11, to deliver the polynucleotide to the subject, wherein the polynucleotide is a RNA replicon.

21. A method of inducing expression of a protein in a subject, the method comprising
administering to the subject the cationic nanolipoprotein (NLPs)-polynucleotide complex of claim 11 comprising a polynucleotide encoding for the protein to induce expression of the protein in the subject, wherein the polynucleotide is a RNA replicon.

22. A method of stimulating a humoral and a cellular immune response in a subject, the method comprising
administering to the subject the cationic nanolipoprotein (NLPs)-polynucleotide complex of claim 11 comprising a polynucleotide encoding a recombinant antigen stimulating both the humoral and the cellular branch of the immune system of the subject,
wherein the polynucleotide is a RNA replicon.

23. A pharmaceutical composition comprising the cationic-nanolipoprotein-polynucleotide complex of claim 11 and a pharmaceutically acceptable vehicle.

24. A composition comprising the cationic-nanolipoprotein-polynucleotide complex of claim 11 and an acceptable vehicle.

25. The cationic-NLPspolynucleotide-complex of claim 11, wherein the polynucleotide has a number of bases from 200 to 5,000 bases.

26. The cationic-NLPspolynucleotide-complex of claim 11, wherein the polynucleotide has a number of bases from 200 to 10,000 bases.

27. The cationic-NLPspolynucleotide-complex of claim 11, wherein the polynucleotide has a number of bases from 200 to 15,000 bases.

28. The cationic-NLPspolynucleotide-complex of claim 11, wherein the polynucleotide has a number of bases from 5,000 to 10,000 bases.

29. The cationic-NLPspolynucleotide-complex of claim 11, wherein the NLPs are at molar ratios ranging from 10 to 500 NLPs per polynucleotide molecule.

30. The cationoc-NLPspolynucleotide-complex of claim 11, wherein the polynucleotide has a number of bases from 10,000 to 15,000 bases and wherein the polynucleotide and the NLP are at molar ratios ranging from 50 500 NLPs per polynucleotide molecules.

31. The cationic-NLPspolynucleotide-complex of claim 11, wherein the polynucleotide has a number of bases from 10,000 to 15,000 bases and wherein the polynucleotide and the NLP are molar ratios ranging from 50 to 150 NLPs per RNA molecules.

32. The cationic-NLPspolynucleotide-complex of claim 11, wherein the polynucleotide has a number of bases from 10,000 to 15,000 bases and wherein the polynucleotide and the NLPs are molar ratios ranging from 10 to 100 NLPs per RNA molecules.

33. The cationic-NLPspolynucleotide-complex of claim 11, wherein the polynucleotide has a number of bases form 10,000 to 15,000 bases and wherein the polynucleotide and the NLPs are molar ratios ranging from 10 to 25 NLPs per RNA molecules.

34. The cationic-NLPspolynucleotide-complex of claim 11, wherein the polynucleotide is an RNA encoding a recombinant antigen stimulating both the humoral and the cellular branch of the immune system of the subject.

35. The cationic-NLPspolynucleotide-complex of claim 11, wherein the cationic lipid is in molar concentration of about 5 to about 40 mol %.

36. The cationic-NLPspolynucleotide-complex of claim 11, wherein the total lipid to scaffold protein molar percent ratio ranges from 20:1 to 240:1.

37. The cationic-NLPspolynucleotide-complex of claim 35, wherein the total lipid to scaffold protein molar percent ratio is 80:1.

38. The cationic-NLPspolynucleotide-complex of claim 11, wherein the cationic lipid comprises at least one cationic lipid selected form the group consisting of dimethyldioctadecylammonium (DDAB), 1,2-dimyristoleoyl-sn-glycero-3-ethylphosphocholine (DMEPC), 1,2-dimyristoyl-3-trimethylammonium-propane (DMTAP), 1,2-dioleoyl-sn-dimethylammonium-propane (DODAP), 1,2-dioleoyl-sn-glycero-3-ethylphosphocholine (DOEPC), dioleoylphosphoethanolamine (DOPE), 1,2-dioleoyl-3-trimethylammonium-propane (DOTAP), 1,2-di-O-octadecenyl-3-trimethylammonium propane (DOTMA) and N1-[2-((1S)-1-[(3-aminopropyl)amino]-4-[di(3-amino-propyl)amino]butylcarboxamido)ethyl]-3,4-di[oleyloxy]-benzamide (MVL5).

39. The cationic-NLPspolynucleotide-complex of claim 11, wherein the cationic lipid comprise lipids of Formula (I)

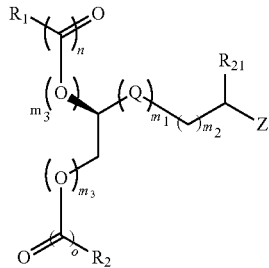

(Formula I)

wherein
R1 and R2 are independently selected from H and a C7-C29 branched or straight, substituted or unsubstituted aliphatic carbon chain;

$R_{21}$ is H, OH, or a carboxy group;
Q is selected from:

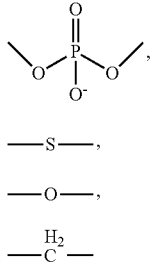

(Formula V)

—S—, (Formula VI)

—O—, (Formula VII)

—CH$_2$— (Formula VIII)

$m_1$=0-1; $m_2$=0-3; $m_3$=0-1 and
n and o are independently 0 and 1;
Z is a moiety of formula (II) or Formula (III) or Formula (IV), wherein
the moiety of Formula (II) is

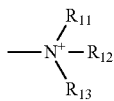

(Formula II)

in which $R_{11}$, $R_{12}$, and $R_{13}$ are independently H or a C1-C4 branched or straight aliphatic carbon chain;
the moiety of Formula (III) is

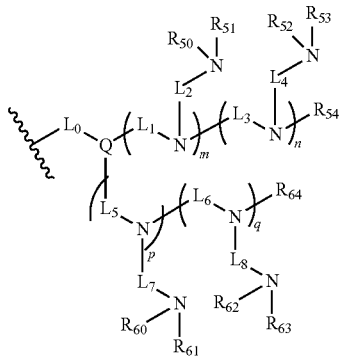

(Formula III)

wherein
Q is N or CH;
m, n, p and q are independently 0-3 and m+n+p+q is equal or greater than 1;
$L_0$-$L_8$ are independently a divalent group selected from $C_{1-6}$ alkylidenyl, $C_{1-6}$ heteroalkylidenyl, $C_{3-6}$ cycloalkylidenyl, and $C_{3-6}$ heterocycloalkylidenyl, wherein each of the alkylidenyl, heteroalkylidenyl, cycloalkylidenyl, and heterocycloalkylidenyl is optionally substituted with one or more substituents independently selected from $C_{1-4}$ alkyl, haloalkyl, $C_{1-4}$ alkoxy, amino, alkylamino, dialkylamino, oxo groups;
$R_{50}$-$R_{54}$, $R_{60}$-$R_{64}$ are independently a monovalent group selected from H, $C_{1-6}$ alkyl, $C_{1-6}$ heteroalkyl, $C_{3-6}$ cycloalkyl, and $C_{3-6}$ heterocycloalkyl, wherein each of the alkyl, heteroalkyl, cycloalkyl, and heterocycloalkyl is optionally substituted with one or more substituents independently selected from $C_{1-4}$ alkyl, haloalkyl, $C_{1-4}$ alkoxy, amino, $C_{1-4}$ alkylamino, $C_{1-4}$ dialkylamino, or a oxo group; and
the moiety of Formula (IV) is

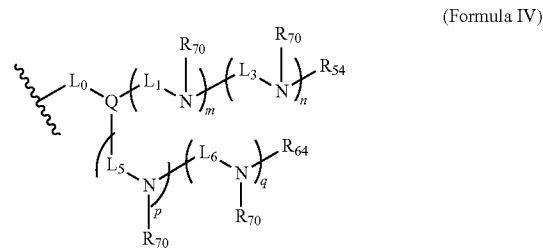

(Formula IV)

in which Q is N or CH;
m, n, p and q are independently 0-3 and m+n+p+q is equal or greater than 1;
$L_0$-$L_1$; $L_3$; and $L_5$-$L_6$ are independently a divalent group selected from $C_{1-6}$ alkylidenyl, $C_{1-6}$ heteroalkylidenyl, $C_{3-6}$ cycloalkylidentyl, and $C_{3-6}$ heterocycloalkylidenyl, wherein each of the alkylidenyl, heteroalkylidenyl, cycloalkylidenyl, and heterocycloalkylidenyl is optionally substituted with one or more substituents independently selected from $C_{1-4}$ alkyl, haloalkyl, $C_{1-4}$ alkoxy, amino, alkylamino, dialkylamino, oxo groups;
$R_{54}$, $R_{64}$ and $R_{70}$ are independently a monovalent group selected from H, $C_{1-6}$ alkyl, $C_{1-6}$ heteroalkyl, $C_{3-6}$ cycloalkyl, and $C_{3-6}$ heterocycloalkyl, wherein each of the alkyl, heteroalkyl, cycloalkyl, and heterocycloalkyl is optionally substituted with one or more substituents independently selected from $C_{1-4}$ alkyl, haloalkyl, $C_{1-4}$ alkoxy, amino, $C_{1-4}$ alkylamino, $C_{1-4}$ dialkylamino, or a oxo group.

40. The cationic-NLPspolynucleotide-complex of claim 11, wherein the membrane forming lipid, cationic lipid and the scaffold protein are at a ratio from 19:1:1 to 96:144:1.

41. The ciationic-NLPspolynucleotide-complex of claim 11, wherein the membrane forming lipid comprises dimyristoylphosphatidycholine (DMPC) and the cationic lipid comprises DMTAP.

42. The cationic-NLPspolynucleotide-complex of claim 11, wherein the DMPC and DMTAP is a ration about 8:2.

43. The cationic-NLPspolynucleotide-complex of claim 11, wherein the scaffold protein is selected from the group comprising apolipoproteins A (apo A-I, apo A-II, apo A-IV, and apo A-V), apolipoproteins B (apo B48 and apo B100), apolipoproteins C-I, apo C-II, apo C-III, and apo C-IV), apolipoproteins D, apolipoproteins E, apolipoproteins H, apolipoprotein E4 (22 Kd fragment), liopophorin III, apolipoprotein A-1 and any derivative or a fragment thereof.

44. The cationic-NLPspolynucleotide-complex of claim 11, wherein the scaffold protein is apoA1, the membrane forming lipid is DMPC and the cationic lipid is DDAB, the DMPC and DDAB at a ratioin about 9:1.

45. The cationic-NLPspolynucleotide-complex of claim 11, wherein the scaffold protein is apoA1, the membrane forming lipid is DMPC and the cationic lipid is DDAB, the DMPC and DDAP, at a ration about 7:3.

46. The ationic-NLPspolynucleotide-complex of claim 11, wherein the scaffold protein is apoE4, the membrane forming lipid is DMPC and the cationic lipid is DODAP, the DMPC and DODAP, at a ratio abouty 7:3.

47. The cationic-NLPspolynucleotide-complex of claim 11, wherein the scaffold protein is apoE4, the membrane forming lipid is DMPC and the cationis lipid is MVL5.

48. The cationic-NLPspolynucleotide-complex of claim 11, further comprising one or more additives selected from the group consisting of cholesterol, Cpg-cholesterol, lyso lipids, monoolein (GMO), Tween 20 and Z3-14.

49. The cationic-NLPspolynucleotide-complex of claim 48, wherein the molar ratio of one or more additives to total lipid content is about 1:99 to 3:2.

50. The catioinic-NLPspolynucleotide-complex of claim 48, wherein the membrane forming lipid ius DMPC, the catioinic lipid is DMTAP, and the one or more additives is GMO, at a ratio of about 8:2:2.

51. The cationis-NLPspolynucleotide-complex of claim 11, further comprising one or more telodendrimers.

52. The cationis-NLPspolynucleotide-complex of claim 51, wherein the telodendrimers are at a ratio of about 0.1% to 10% of a total lipid component of the membrane forming lipid and the cationic lipid.

* * * * *